(12) United States Patent
Kim et al.

(10) Patent No.: US 9,724,420 B2
(45) Date of Patent: Aug. 8, 2017

(54) LIQUID FORMULATION OF PROTEIN CONJUGATE COMPRISING AN OXYNTOMODULIN DERIVATIVE COVALENTLY LINKED TO A NON-PEPTIDYL POLYMER TO AN IMMUNOGLOBULIN FC REGION

(71) Applicant: HANMI PHARM. CO., LTD., Hwaseong-si, Gyeonggi-do (KR)

(72) Inventors: Hyun Uk Kim, Hwaseong-si (KR); Hyung Kyu Lim, Hwaseong-si (KR); Myung Hyun Jang, Seoul (KR); Sang Yun Kim, Gimpo-si (KR); Sung Min Bae, Seongnam-si (KR); Se Chang Kwon, Seoul (KR)

(73) Assignee: Hanmi Pharm. Co., Ltd., Hwaseong-Si, Gyeonggi-Do (KR)

( * ) Notice: Subject to any disclaimer, the term of this patent is extended or adjusted under 35 U.S.C. 154(b) by 0 days.

(21) Appl. No.: 14/440,422

(22) PCT Filed: Nov. 6, 2013

(86) PCT No.: PCT/KR2013/009986
§ 371 (c)(1),
(2) Date: May 4, 2015

(87) PCT Pub. No.: WO2014/073842
PCT Pub. Date: May 15, 2014

(65) Prior Publication Data
US 2015/0290324 A1      Oct. 15, 2015

(30) Foreign Application Priority Data

Nov. 6, 2012 (KR) .................. 10-2012-0124725

(51) Int. Cl.
| | |
|---|---|
| *A61K 9/08* | (2006.01) |
| *A61K 38/26* | (2006.01) |
| *A61K 47/48* | (2006.01) |
| *C07K 14/605* | (2006.01) |
| *A61K 47/26* | (2006.01) |
| *A61K 9/00* | (2006.01) |
| *A61K 47/10* | (2017.01) |
| *A61K 47/02* | (2006.01) |
| *A61K 47/12* | (2006.01) |
| *A61K 47/20* | (2006.01) |
| *A61K 47/22* | (2006.01) |

(52) U.S. Cl.
CPC ............ *A61K 47/26* (2013.01); *A61K 9/0019* (2013.01); *A61K 9/08* (2013.01); *A61K 38/26* (2013.01); *A61K 47/02* (2013.01); *A61K 47/10* (2013.01); *A61K 47/12* (2013.01); *A61K 47/20* (2013.01); *A61K 47/22* (2013.01); *A61K 47/48369* (2013.01); *A61K 47/48415* (2013.01); *C07K 14/605* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,217,845 B2 | 5/2007 | Rosen et al. | |
| 7,521,424 B2 | 4/2009 | Rosen et al. | |
| 7,737,260 B2 | 6/2010 | Kim et al. | |
| 7,928,058 B2 | 4/2011 | Roy et al. | |
| 8,263,084 B2 | 9/2012 | Song et al. | |
| 8,729,017 B2 * | 5/2014 | DiMarchi ............ | C07K 14/605 514/11.7 |
| 8,778,872 B2 | 7/2014 | DiMarchi et al. | |
| 2004/0087778 A1 | 5/2004 | Feige et al. | |
| 2009/0238838 A1 | 9/2009 | Kim et al. | |
| 2009/0298757 A1 | 12/2009 | Bloom et al. | |
| 2010/0190701 A1 | 7/2010 | Day et al. | |
| 2010/0196405 A1 | 8/2010 | Ng | |

(Continued)

FOREIGN PATENT DOCUMENTS

| | | |
|---|---|---|
| CN | 101213209 A | 7/2008 |
| CN | 101389648 A | 3/2009 |

(Continued)

OTHER PUBLICATIONS

US 8,729,011, 05/2014, DiMarchi et al. (withdrawn)
International Searching Authority, International Search Report of PCT/KR2013/009986 dated Jan. 29, 2014 [PCT/ISA/210].
International Searching Authority, Written Opinion of PCT/KR2013/009986 dated Jan. 29, 2014 [PCT/ISA/237].
"Obesity Causes,", Obesity Prevention Source, http://www.hsph.harvard.edu/obesity-prevention-source/obesity-causes/, accessed Oct. 6, 2014, 1-3.
"Obesity", Merck Manual, http://www.merckmanuals.com/professoinal/nutritional_disorders/obesity_and_the_metab., accessed Oct. 6, 2014, 1-9.

(Continued)

*Primary Examiner* — Elly-Gerald Stoica
(74) *Attorney, Agent, or Firm* — Baker & Hostetler LLP

(57) ABSTRACT

Disclosed are an albumin-free liquid formulation including a long-lasting oxyntomodulin conjugate in which an oxyntomodulin peptide comprising a derivative, variant, precursor or fragment of oxyntomodulin is linked to an immunoglobulin Fc region, which can increase the duration of physiological activity of the long-lasting oxyntomodulin conjugate and maintain the in vivo stability thereof for an extended period of time, as compared to native oxyntomodulin, and a method for preparing the liquid formulation. The liquid formulation contains a buffer, a sugar alcohol and a nonionic surfactant and does not contain a human serum albumin and factors that are potentially harmful to the human body, and thus is not susceptible to viral infection. The oxyntomodulin conjugate contains oxyntomodulin linked to an immunoglobulin Fc region, and thus has a large molecular weight, prolonged physiological activity, and excellent storage stability, compared to native oxyntomodulin.

27 Claims, 24 Drawing Sheets

(56) References Cited

U.S. PATENT DOCUMENTS

| | | |
|---|---|---|
| 2010/0330108 A1 | 12/2010 | Song et al. |
| 2011/0034374 A1 | 2/2011 | Bloom et al. |
| 2011/0065633 A1 | 3/2011 | DiMarchi et al. |
| 2011/0152182 A1 | 6/2011 | Alsina-Fernandez et al. |
| 2012/0003712 A1 | 1/2012 | Song et al. |
| 2012/0165503 A1 | 6/2012 | Carrington et al. |
| 2012/0329707 A1 | 12/2012 | DiMarchi et al. |
| 2013/0035285 A1 | 2/2013 | Lau et al. |

FOREIGN PATENT DOCUMENTS

| | | |
|---|---|---|
| CN | 101578107 A | 11/2009 |
| CN | 102010473 A | 4/2011 |
| CN | 102369209 A | 3/2012 |
| CN | 101974077 A | 5/2012 |
| CN | 103732618 A | 10/2013 |
| CN | 103732616 A | 4/2014 |
| EP | 1891105 B1 | 2/2008 |
| EP | 2300037 | 3/2011 |
| EP | 2330124 | 6/2011 |
| JP | 2003-531632 A | 10/2003 |
| JP | 2008-543816 A | 12/2008 |
| JP | 2009-527558 A | 9/2009 |
| JP | 2009-203235 A | 12/2009 |
| JP | 2011-511753 A | 8/2010 |
| JP | 2013-537525 A | 2/2011 |
| KR | 10-0389726 B1 | 6/2003 |
| KR | 10-2005-0026685 A | 3/2005 |
| KR | 10-2006-0106486 A | 10/2006 |
| KR | 10-2008-0039375 A | 5/2008 |
| KR | 10-2009-0098843 A | 9/2009 |
| KR | 10-0925017 B1 | 11/2009 |
| KR | 10-2010-0105494 A | 9/2010 |
| KR | 10-2011-0039230 A | 4/2011 |
| KR | 10-2009-0096498 A | 5/2012 |
| KR | 10-2012-0043208 A * | 5/2012 ............ A61K 47/48 |
| KR | 10-2012-0043208 A | 5/2012 |
| KR | 10-2012-0052973 A | 5/2012 |
| KR | 10-2012-0139579 A | 12/2012 |
| KR | 10-2014-0018462 | 2/2014 |
| WO | WO 03/022304 | 3/2003 |
| WO | WO 2005/035761 A1 | 10/2003 |
| WO | WO 2004/062685 A2 | 7/2004 |
| WO | WO 2005/087797 A1 | 9/2005 |
| WO | WO 2006/059106 A2 | 6/2006 |
| WO | WO 2006/134340 A2 | 12/2006 |
| WO | WO 2007/022123 A2 | 2/2007 |
| WO | WO 2007/100535 A2 | 9/2007 |
| WO | WO 2007/146038 A2 | 12/2007 |
| WO | WO 2008/071972 A1 | 6/2008 |
| WO | WO 2008/082274 A1 | 7/2008 |
| WO | WO 2008/101017 A2 | 8/2008 |
| WO | WO 2009/033756 A2 | 3/2009 |
| WO | WO 2009/058734 A1 | 5/2009 |
| WO | WO 2009/069983 A2 | 6/2009 |
| WO | WO 2009/099763 A1 | 8/2009 |
| WO | WO 2009/155257 A1 | 12/2009 |
| WO | WO 2009/155258 A1 | 12/2009 |
| WO | WO 2010/013012 A2 | 2/2010 |
| WO | WO 2010/033207 A1 | 3/2010 |
| WO | WO 2010/033220 A2 | 3/2010 |
| WO | WO 2010/070253 A1 | 6/2010 |
| WO | WO 2010/071807 A1 | 6/2010 |
| WO | WO 2010/096052 A1 | 8/2010 |
| WO | WO 2010/096142 A1 | 8/2010 |
| WO | WO 2010/107256 A2 | 9/2010 |
| WO | WO 2010/108153 A2 | 9/2010 |
| WO | WO2010108153 * | 9/2010 ........... A61K 39/395 |
| WO | WO 2010/148089 A1 | 12/2010 |
| WO | WO 2011/006497 A1 | 1/2011 |
| WO | WO 2011/056713 | 5/2011 |
| WO | WO 2011/071957 A1 | 6/2011 |
| WO | WO 2011/075393 A2 | 6/2011 |
| WO | WO 2011/087671 | 7/2011 |
| WO | WO 2011/087672 | 7/2011 |
| WO | WO 2011/143208 | 11/2011 |
| WO | 2012/011752 A2 | 1/2012 |
| WO | WO 2012/057525 A2 | 5/2012 |
| WO | WO 2012/088379 A2 | 6/2012 |
| WO | WO 2012/169798 A2 | 12/2012 |
| WO | WO 2012/173422 A1 | 12/2012 |
| WO | WO 2013/157002 A1 | 10/2013 |
| WO | WO 2014/017843 | 1/2014 |
| WO | WO 2014/073842 | 5/2014 |

OTHER PUBLICATIONS

"Prescription Medications for the Treatment of Obesity", U.S. Department of Health and Human Services, Apr. 2013, 1-8.

"Water", http/://222.biology-online.org/dictionary/Water, accessed Apr. 24, 2014, 1-3.

"What Causes Overweight and Obesity?", National Heart, Lung, and Blood Institute, http://www.nhibi.nih.gov/health/health-topics/topics/obe/causes.html, accessed Oct. 6, 2014, 1-5.

"Definition of Prophylactic", Merriam Webster Dictionary, accessed Feb. 8, 2015, http://www.merriam-webster.com/dictionary/prophylactic, 1 page.

"Exendin-4", Sigma-Aldrich, 2004, http://www.simgaaldrich.com/catalog/product/sigma/e7144lang=en®ion=US, accessed Dec. 28, 2015, 1 page.

"Vitamins & Supplements Search", http/://222.webmd.com/vitamins-supplements/condition-1275-Hyperlipidemia.aspx, accessed Dec. 29, 2015, 1-3.

Berendsen, "A Glimpse of the Holy Grail?", Science, 1998, 282, 642-643.

Bradley et al., Limits of Cooperativity in a Structurally Modular Protein: Response of the Notch Ankyrin Domain to Analogous Alanine Substitutions in Each Repeat, 2002, 373-386.

Collie et al., "Purification and sequence of rat oxyntomodulin", Proc. Natl. Acad. Sci., Sep. 1994, vol. 91, 9362-9366.

Day et al., "A new glucagon and GLP-1 co-agonist eliminates obesity in rodents", Nature Chemical Biology, 2009, 6, 749-757.

Day et al., "Optimization of Co-Agonism at GLP-1 and Glucagon Receptors to Safely Maximize Weight Reduction in DIO-Rodents", Peptide Science, Apr. 2012, 98, 443-450.

Ding et al., "Exendin-4, a Glucagon-Like Protein-1 (GLP-1) Receptor Agonist, Reverses Hepatic Steatosis in ob/ob Mice", Hepatology, 2006, 43, 173-181.

Drucker, "Glucagon-Like Peptides", Diabetes, Feb. 1998, vol. 47, 159-169.

European Patent Office, "Supplementary European Search Report", dated Dec. 3, 2014, issued in counterpart Application No. 12797363.4, 5 pages.

European Patent Office, "Supplementary European Search Report", dated Oct. 13, 2014, issued in counterpart Application No. 12801247.3, 7 pages.

European Patent Office, "Supplementary Partial European Search Report", dated Feb. 25, 2016, issued in counterpart Application No. 13823727.6, 7 pages.

Federal Institute of Industrial Property, "Office Action", dated Dec. 4, 2015, issued in corresponding Russian Application No. 2013153198/10, 15 pages.

Federal Institute of Industrial Property, "Office Action", dated Dec. 4, 2015, issued in corresponding Russian Application No. 2013154066/10, 14 pages.

Frankel et al., "Characterization of diphtheria fusion proteins targeted to the human interleukin-3 receptor," Protein Engineering, 2000, vol. 13, No. 8, 575-581.

Goldberg, "Dyslipidemia", http://www.merckmanuals.com/professional/endocrine-and-metabolic-diorders/lipid-dis. . . , accessed Dec. 29, 2015, 1-11.

Hepatitis Health Center, "Fatty Liver Disease", http://www.webmd.com/hepatitis/fatty-liver-diseasepage=2&print=true, accessed Dec. 19, 2015, 1-4.

International Patent Application No. PCT/KR2012/004722: International Search Report and Written Opinion dated Nov. 14, 2012, 6 pages.

International Patent Application No. PCT/KR2013/006668: International Search Report dated Oct. 21, 2013, 10 pages.

(56) References Cited

OTHER PUBLICATIONS

International Patent Application No. PCT/KR2013/009986: International Search Report dated Jan. 29, 2014, 11 pages.
International Patent Application No. PCT/KR2013/009990: International Search Report and Written Opinion dated Jan. 20, 2014, 12 pages.
Japan Patent Office, "Grounds for Rejection", dated Dec. 15, 2015, issued in corresponding Japanese Application 2014/515759, 12 pages.
Japan Patent Office, "Grounds for Rejection", dated Nov. 24, 2015, issued in corresponding Japanese Application No. 2014-514799, 9 pages.
Korean Intellectual Property Office, "Decision to Grant a Patent", dated Feb. 26, 2015, issued in corresponding Korean Application No. 10-2012-0061166, 5 pages.
Korean Intellectual Property Office, "Notice of Final Rejection", dated Aug. 28, 2014, issued in corresponding Korean Application No. 10-2012-0061166, 6 pages.
Korean Intellectual Property Office, "Notice of Preliminary Rejection", dated Sep. 30, 2013, issued in corresponding Korean Application No. 10-2012-0061166, 9 pages.
Korean Intellectual Property Office, "Notice of Preliminary Rejection", dated Nov. 20, 2014, issued in corresponding Korean Application No. 10-2012-0061166, 7 pages.
Lam, "Atherosclerosis", http://www.merkmanuals.com/professional/cardiovascular-disorder/arteriosclerosis/atherosclerosis, accessed Dec. 29, 2015, 1-14.
Lam, "Definition of Arteriosclerosis", http://www.merkmanuals.com/professional/cardiovascular-disorders/arteriosclerosis/defi . . . , accessed Dec. 29, 2015, 1 page.
Lam, "Nonatheromatous Arteriosclerosis", http://222.merckmanuals.com/profession/cardiovasculardisorders/arteriosclerosis/non. . . , accessed Dec. 29, 2015, 1-2.
Machine Translation of Korean Publication: 1020100105494 A, dated Sep. 29, 2010, Hanmi Holdings Co. Ltd., 48 pages.
New Zealand Intellectual Property Office, "First Examination Report", dated Oct. 7, 2014, issued in corresponding application No. 618810, 3 pages.
New Zealand Intellectual Property Office, "Further Examination Report", dated Oct. 30, 2015, issued in corresponding application No. 618810, 4 pages.
Ngo et al., "Computational Complexity, Protein Structure Protection, and the Levinthal Paradox", The Protein Folding Problem and Tertiary Structure Prediction, 1994, 491-494.
Pocai et al., "Glucagon-like peptide 1/glucagon receptor dual agonism reverses obesity in mice", Diabetes, 2009, vol. 58, No. 10, 2253-2266.
Rudinger, "Characteristics of the amino acids as components of a peptide hormone sequence", Peptide Hormones , JA Parsons Ed., 1976, pp. 1-7.
Santoprete et al., "DPP-IV-resistant, long acting oxyntomodulin derivatives," Journal of Peptide Science, 2011, vol. 17, No. 4, 270-280.
Skosyrev et al., "The Dependence of Stability of the Green Fluorescent-Protein-Obelin Hybrids on the Nature of Their Constituent Modules and the Structure of the Amino Acid Linker," Russian Journal of Bioorganic Chemistry, 2001, vol. 27, No. 5, 323-329.
State Intellectual Property Office of PRC, "English translation of Notification of First Office Action", dated Mar. 6, 2015, issued in corresponding Chinese Application No. 201280038851.4, 7 pages.
State Intellectual Property Office of PRC, "Notification of First Office Action", dated Jan. 7, 2015 issued in corresponding Chinese Application No. 201280039781.4, 21 pages.
State Intellectual Property Office of PRC, "Notification of Second Office Action", dated Sep. 24, 2015, issued in corresponding Chinese Application No. 201280039781.4, 11 pages.
State Intellectual Property Office of PRC, "Notification of Second Office Action", dated Sep. 15, 2015, issued in corresponding Chinese Application No. 201280038851.4, 15 pages.
Taiwanese Intellectual Property Office, "Examination Report", dated Dec. 23, 2013 issued in corresponding application No. 101121483, 15 pages.
Treetharnmathurot et al., "Effect of PEG molecular weight and linking chemistry on the biological activity and thermal stability of PEGylated trypsin," International Journal of Pharmaceutics, 2008, vol. 357, 252-259.
U.S. Appl. No. 14/124,969: Communication dated Jun. 25, 2014, 12 pages.
U.S. Appl. No. 14/124,969: Final Rejection, dated Apr. 14, 2015, 17 pages.
U.S. Appl. No. 14/124,969: Non-Final Rejection, dated Dec. 10, 2014, 40 pages.
U.S. Appl. No. 14/126,914: Communication, dated Sep. 18, 2014, 14 pages.
U.S. Appl. No. 14/126,914: Examiner Initialed Interview, dated Feb. 29, 2016, 29 pages.
U.S. Appl. No. 14/126,914: Non-Final Rejection, dated Mar. 5, 2015, 35 pages.
U.S. Appl. No. 14/415,200: Communication, dated Jan. 20, 2016, 39 pages.
U.S. Appl. No. 14/748,389: Non-Final Rejection, dated Jan. 13, 2016, 18 pages.
Voet et al., "Abnormal Hemoglobins", Biochemistry, John Wiley & Sons Inc., 1995, 235-241.
Vorobiev et al., "Chemical polysialylation: Design of conjugated human oxyntomodulin with a prolonged anorexic effect in vivo", Biochimie, 2013, vol. 95, 264-270.
Wynne et al., "Oxyntomodulin increases energy expediture in addition to decreasing energy intake in overweight and obese humans: a randomised controlled trial," International Journal of Obesity, 2006, 30, 1729-1736.
Wynne et al., "Subcutaneous Oxyntomodulin Reduces Body Weight in Overweight and Obese Subjects a Doube-Blind, Randomized, Controlled Trial," Diabetes, Aug. 2005, vol. 54, 2390-2395.
New Zealand Patent Application No. 718999: Further Examination Report dated Oct. 26, 2016, 3 pages.

* cited by examiner

Figure 5b

SE-HPLC

Percent retention of long-lasting oxyntomodulin conjugate (%)

- 0 week
- 4 week

RP-HPLC

■ 0 week  ■ 4 week

1: 100.00, 65.05
2: 100.00, 65.03
3: 100.00, 65.02
4: 100.00, 67.79

Percent retention of long-lasting oxyntomodulin conjugate (%)

Figure 7b

Bar chart: Percent retention of long-lasting oxyntomodulin conjugate (%) by SE-HPLC at 0 week and 4 week.

| Sample | 0 week | 4 week |
|---|---|---|
| #1 | 100.00 | 100.10 |
| #2 | 100.00 | 99.19 |
| #3 | 100.00 | 99.04 |
| #4 | 100.00 | 98.80 |
| #5 | 100.00 | 97.70 |

Figure 8c

RP-HPLC

■ 0 week  ■ 4 week

1: 100.00, 98.76
2: 100.00, 97.94
3: 100.00, 97.74
4: 100.00, 97.37

Percent retention of long-lasting oxyntomodulin conjugate (%)

SEQUENCE LISTING

<160> NUMBER OF SEQ ID NOS: 55

<210> SEQ ID NO 1
<211> LENGTH: 37
<212> TYPE: PRT
<213> ORGANISM: Homo sapiens
<220> FEATURE:
<221> NAME/KEY: MISC_FEATURE
<222> LOCATION: (1)..(37)
<223> OTHER INFORMATION: Oxyntomodulin

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 2

His Ser Gln Gly Thr Phe Thr Ser Asp Tyr Ser Lys Tyr Leu Asp Glu
1               5                   10                  15

Glu Ala Val Arg Leu Phe Ile Glu Trp Leu Met Asn Thr Lys Arg Asn
            20                  25                  30

Arg Asn Asn Ile Ala
        35

<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 3

His Ser Gln Gly Thr Phe Thr Ser Asp Tyr Ser Lys Tyr Leu Asp Glu
1               5                   10                  15

Arg Arg Ala Gln Asp Phe Val Ala Trp Leu Lys Asn Thr Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative

```
<220> FEATURE:
<221> NAME/KEY: MOD_RES
<222> LOCATION: (1)..(1)
<223> OTHER INFORMATION: 4-imidazoacetyl

<400> SEQUENCE: 4

His Gly Gln Gly Thr Phe Thr Ser Asp Tyr Ser Arg Tyr Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 5

His Gly Gln Gly Thr Phe Thr Ser Asp Tyr Ser Arg Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 6
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 6

His Gly Glu Gly Thr Phe Thr Ser Asp Leu Ser Arg Gln Met Glu Glu
1               5                   10                  15

Glu Ala Val Arg Leu Phe Ile Glu Trp Ala Ala His Ser Gln Gly Thr
            20                  25                  30

Phe Thr Ser Asp Tyr Ser Lys Tyr Leu Asp
        35                  40

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 7
```

His Ser Gln Gly Thr Phe Thr Ser Asp Tyr Ser Arg Tyr Leu Asp Glu
1               5                   10                  15

Glu Ala Val Arg Leu Phe Ile Glu Trp Leu Met Asn Thr Lys
            20                  25                  30

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 8

His Ser Gln Gly Thr Phe Thr Ser Asp Leu Ser Arg Gln Leu Glu Glu
1               5                   10                  15

Glu Ala Val Arg Leu Phe Ile Glu Trp Leu Met Asn Lys
            20                  25

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (20)..(20)
<223> OTHER INFORMATION: Alpha-methyl-glutamic acid

<400> SEQUENCE: 9

His Gly Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys Arg Asn
            20                  25                  30

Arg Asn Asn Ile Ala
        35

<210> SEQ ID NO 10
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 10

His Ser Gln Gly Thr Phe Thr Ser Asp Tyr Ser Arg Gln Met Glu Glu
1               5                   10                  15

Glu Ala Val Arg Leu Phe Ile Glu Trp Leu Met Asn Gly Gly Pro Ser
            20                  25                  30

Ser Gly Ala Pro Pro Pro Ser Lys
        35                  40

<210> SEQ ID NO 11
<211> LENGTH: 43
<212> TYPE: PRT
<213> ORGANISM: Artificial Sequence
<220> FEATURE:
<223> OTHER INFORMATION: Description of Artificial Sequence: Synthetic
    polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 11

His Gly Glu Gly Thr Phe Thr Ser Asp Leu Ser Arg Gln Met Glu Glu
1               5                   10                  15

Glu Ala Val Arg Leu Phe Ile Glu Trp Ala Ala His Ser Gln Gly Thr
            20                  25                  30

Phe Thr Ser Asp Tyr Ser Arg Tyr Leu Asp Lys
        35                  40

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
    polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 12

His Ser Gln Gly Thr Phe Thr Ser Asp Tyr Ser Arg Tyr Leu Asp Gly
1               5                   10                  15

Gly Gly His Gly Glu Gly Thr Phe Thr Ser Asp Leu Ser Lys Gln Met
            20                  25                  30

Glu Glu Glu Ala Val Lys
        35

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic
    polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (16)..(16)
<223> OTHER INFORMATION: Alpha-methyl-glutamic acid
<220> FEATURE:
<221> NAME/KEY: MOD_RES
<222> LOCATION: (20)..(20)
<223> OTHER INFORMATION: Alpha-methyl-glutamic acid

<400> SEQUENCE: 13

His Ser Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys
            20                  25                  30

<210> SEQ ID NO 14

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (20)..(20)
<223> OTHER INFORMATION: Alpha-methyl-glutamic acid
<220> FEATURE:
<221> NAME/KEY: MOD_RES
<222> LOCATION: (24)..(24)
<223> OTHER INFORMATION: Alpha-methyl-glutamic acid

<400> SEQUENCE: 14

His Gly Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys Arg Asn
            20                  25                  30

Arg Asn Asn Ile Ala
        35

<210> SEQ ID NO 15
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (24)..(24)
<223> OTHER INFORMATION: Alpha-methyl-glutamic acid

<400> SEQUENCE: 15

His Gly Gln Gly Thr Phe Thr Ser Asp Tyr Ser Arg Tyr Leu Asp Glu
1               5                   10                  15

Glu Ala Val Arg Leu Phe Ile Glu Trp Leu Met Asn Thr Lys Arg Asn
            20                  25                  30

Arg Asn Asn Ile Ala
        35

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 16

His Ser Gln Gly Thr Phe Thr Ser Asp Leu Ser Arg Gln Leu Glu Gly
1               5                   10                  15

Gly Gly His Ser Gln Gly Thr Phe Thr Ser Asp Leu Ser Arg Gln Leu
            20                  25                  30
```

Glu Lys

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 17

His Ser Gln Gly Thr Phe Thr Ser Asp Tyr Ser Arg Tyr Leu Asp Glu
1               5                   10                  15

Glu Ala Val Arg Leu Phe Ile Glu Trp Ile Arg Asn Thr Lys Arg Asn
            20                  25                  30

Arg Asn Asn Ile Ala
        35

<210> SEQ ID NO 18
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 18

His Ser Gln Gly Thr Phe Thr Ser Asp Tyr Ser Arg Tyr Leu Asp Glu
1               5                   10                  15

Glu Ala Val Arg Leu Phe Ile Glu Trp Ile Arg Asn Gly Gly Pro Ser
            20                  25                  30

Ser Gly Ala Pro Pro Pro Ser Lys
        35                  40

<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MISC_FEATURE
<222> LOCATION: (16)..(20)
<223> OTHER INFORMATION: Ring formation between residues

<400> SEQUENCE: 19

His Ser Gln Gly Thr Phe Thr Ser Asp Tyr Ser Arg Tyr Leu Asp Glu
1               5                   10                  15

Glu Ala Val Lys Leu Phe Ile Glu Trp Ile Arg Asn Thr Lys Arg Asn
            20                  25                  30

Arg Asn Asn Ile Ala
        35

<210> SEQ ID NO 20
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MISC_FEATURE
<222> LOCATION: (16)..(20)
<223> OTHER INFORMATION: Ring formation between residues

<400> SEQUENCE: 20

His Ser Gln Gly Thr Phe Thr Ser Asp Tyr Ser Arg Tyr Leu Asp Glu
1               5                   10                  15

Glu Ala Val Lys Leu Phe Ile Glu Trp Ile Arg Asn Gly Gly Pro Ser
            20                  25                  30

Ser Gly Ala Pro Pro Ser Lys
        35                  40

<210> SEQ ID NO 21
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 21

His Ser Gln Gly Thr Phe Thr Ser Asp Tyr Ser Arg Gln Leu Glu Glu
1               5                   10                  15

Glu Ala Val Arg Leu Phe Ile Glu Trp Val Arg Asn Thr Lys Arg Asn
            20                  25                  30

Arg Asn Asn Ile Ala
        35

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: Desamino-histidyl
<220> FEATURE:
<221> NAME/KEY: MISC_FEATURE
<222> LOCATION: (16)..(20)
<223> OTHER INFORMATION: Ring formation between residues

<400> SEQUENCE: 22

His Ser Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Lys
            20                  25                  30

<210> SEQ ID NO 23
<211> LENGTH: 29

```
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (2)..(2)
<223> OTHER INFORMATION: Aib

<400> SEQUENCE: 23

His Xaa Gln Gly Thr Phe Thr Ser Asp Tyr Ser Lys Tyr Leu Asp Glu
1               5                   10                  15

Lys Arg Ala Lys Glu Phe Val Cys Trp Leu Met Asn Thr
            20                  25

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (2)..(2)
<223> OTHER INFORMATION: Aib

<400> SEQUENCE: 24

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 25

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (12)..(16)
```

```
<223> OTHER INFORMATION: Ring formation between residues

<400> SEQUENCE: 26

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 27
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 27

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (2)..(2)
<223> OTHER INFORMATION: Aib

<400> SEQUENCE: 28

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr
            20                  25

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (2)..(2)
<223> OTHER INFORMATION: D-Ser

<400> SEQUENCE: 29

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35
```

<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 30

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (2)..(2)
<223> OTHER INFORMATION: D-Ser

<400> SEQUENCE: 31

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 32

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 33

His Xaa Gln Gly Thr Phe Thr Ser Asp Tyr Ala Lys Tyr Leu Asp Glu
1               5                   10                  15
Lys Arg Ala Lys Glu Phe Val Gln Trp Leu Met Asn Thr Cys
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 34

Tyr Xaa Gln Gly Thr Phe Thr Ser Asp Tyr Ser Lys Tyr Leu Asp Glu
1               5                   10                  15
Lys Arg Ala Lys Glu Phe Val Gln Trp Leu Met Asn Thr Cys
            20                  25                  30

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 35

Lys Arg Asn Arg Asn Asn Ile Ala
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 36

Gly Pro Ser Ser Gly Ala Pro Pro Pro Ser

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 37

Gly Pro Ser Ser Gly Ala Pro Pro Pro Ser Lys
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 38

His Ser Gln Gly Thr Phe Thr Ser Asp Tyr Ser Lys Tyr Leu Asp
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 39

His Ser Gln Gly Thr Phe Thr Ser Asp Tyr Ser Arg Tyr Leu Asp Lys
1               5                   10                  15

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 40

His Gly Glu Gly Thr Phe Thr Ser Asp Leu Ser Lys Gln Met Glu Glu
1               5                   10                  15

Glu Ala Val Lys
            20

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 41

Ser Gln Gly Thr Phe Thr Ser Asp Tyr Ser Lys Tyr Leu Asp Ser Arg
1               5                   10                  15

Arg Ala Gln Asp Phe Val Gln Trp Leu Met Asn Thr
            20                  25

-continued

```
<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 42

Ser Gln Gly Thr Phe Thr Ser Asp Tyr Ser Lys Tyr Leu Asp Glu Glu
1               5                   10                  15

Ala Val Arg Leu Phe Ile Glu Trp Leu Met Asn Thr
            20                  25

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 43

Ser Gln Gly Thr Phe Thr Ser Asp Tyr Ser Lys Tyr Leu Asp Glu Arg
1               5                   10                  15

Arg Ala Gln Asp Phe Val Ala Trp Leu Lys Asn Thr
            20                  25

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 44

Gly Gln Gly Thr Phe Thr Ser Asp Tyr Ser Arg Tyr Leu Glu Glu Glu
1               5                   10                  15

Ala Val Arg Leu Phe Ile Glu Trp Leu Lys Asn Gly
            20                  25

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 45

Gly Gln Gly Thr Phe Thr Ser Asp Tyr Ser Arg Gln Met Glu Glu Glu
1               5                   10                  15

Ala Val Arg Leu Phe Ile Glu Trp Leu Lys Asn Gly
            20                  25

<210> SEQ ID NO 46
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 46

Gly Glu Gly Thr Phe Thr Ser Asp Leu Ser Arg Gln Met Glu Glu Glu
```

```
                1               5                   10                  15

Ala Val Arg Leu Phe Ile Glu Trp Ala Ala
            20                  25

<210> SEQ ID NO 47
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 47

Ser Gln Gly Thr Phe Thr Ser Asp Tyr Ser Arg Gln Met Glu Glu Glu
1               5                   10                  15

Ala Val Arg Leu Phe Ile Glu Trp Leu Met Asn Gly
            20                  25

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide construct of group B

<400> SEQUENCE: 48

Gly Glu Gly Thr Phe Thr Ser Asp Leu Ser Arg Gln Met Glu Glu Glu
1               5                   10                  15

Ala Val Arg Leu Phe Ile Glu Trp
            20

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide construct of group B

<400> SEQUENCE: 49

Ser Gln Gly Thr Phe Thr Ser Asp Tyr Ser Arg Tyr Leu Asp
1               5                   10

<210> SEQ ID NO 50
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MOD_RES
<222> LOCATION: (2)..(2)
<223> OTHER INFORMATION: Aib (aminosiobutyric acid), d-alanine, glycine,
      Sar (N-methylglycine), serine or d-serine
<220> FEATURE:
<221> NAME/KEY: MOD_RES
<222> LOCATION: (3)..(3)
<223> OTHER INFORMATION: Glutamic acid or glutamine
<220> FEATURE:
<221> NAME/KEY: MOD_RES
<222> LOCATION: (10)..(10)
```

```
<223> OTHER INFORMATION: Leucine or tyrosine
<220> FEATURE:
<221> NAME/KEY: MOD_RES
<222> LOCATION: (11)..(11)
<223> OTHER INFORMATION: Serine or alanine
<220> FEATURE:
<221> NAME/KEY: MOD_RES
<222> LOCATION: (12)..(12)
<223> OTHER INFORMATION: Lysine or arginine
<220> FEATURE:
<221> NAME/KEY: MOD_RES
<222> LOCATION: (13)..(13)
<223> OTHER INFORMATION: Glutamine or tyrosine
<220> FEATURE:
<221> NAME/KEY: MOD_RES
<222> LOCATION: (14)..(14)
<223> OTHER INFORMATION: Leucine or methionine
<220> FEATURE:
<221> NAME/KEY: MOD_RES
<222> LOCATION: (15)..(15)
<223> OTHER INFORMATION: Aspartic acid or glutamic acid
<220> FEATURE:
<221> NAME/KEY: MOD_RES
<222> LOCATION: (16)..(16)
<223> OTHER INFORMATION: Glutamic acid, serine, alpha-methyl-glutamic
     acid or not present
<220> FEATURE:
<221> NAME/KEY: MOD_RES
<222> LOCATION: (17)..(17)
<223> OTHER INFORMATION: Glutamine, glutamic acid, lysine, arginine,
     serine or not present
<220> FEATURE:
<221> NAME/KEY: MOD_RES
<222> LOCATION: (18)..(18)
<223> OTHER INFORMATION: Alanine, arginine, valine or not present
<220> FEATURE:
<221> NAME/KEY: MOD_RES
<222> LOCATION: (19)..(19)
<223> OTHER INFORMATION: Alanine, arginine, serine, valine or not
     present
<220> FEATURE:
<221> NAME/KEY: MOD_RES
<222> LOCATION: (20)..(20)
<223> OTHER INFORMATION: Lysine, glutamine, arginine, alpha-methyl-
     glutamic acid or not present
<220> FEATURE:
<221> NAME/KEY: MOD_RES
<222> LOCATION: (21)..(21)
<223> OTHER INFORMATION: Aspartic acid, glutamic acid, leucine or not
     present
<220> FEATURE:
<221> NAME/KEY: MISC_FEATURE
<222> LOCATION: (22)..(22)
<223> OTHER INFORMATION: May or may not be present
<220> FEATURE:
<221> NAME/KEY: MOD_RES
<222> LOCATION: (23)..(23)
<223> OTHER INFORMATION: Isoleucine, valine or not present
<220> FEATURE:
<221> NAME/KEY: MOD_RES
<222> LOCATION: (24)..(24)
<223> OTHER INFORMATION: Alanine, cysteine, glutamic acid, lysine,
     glutamine, alpha-methyl-glutamic acid or not present
<220> FEATURE:
<221> NAME/KEY: MISC_FEATURE
<222> LOCATION: (25)..(25)
<223> OTHER INFORMATION: May or may not be present
<220> FEATURE:
<221> NAME/KEY: MOD_RES
<222> LOCATION: (26)..(26)
<223> OTHER INFORMATION: Alanine, isoleucine, leucine, serine, valine
     or not present
<220> FEATURE:
<221> NAME/KEY: MOD_RES
<222> LOCATION: (27)..(27)
<223> OTHER INFORMATION: Alanine, lysine, methionine, glutamine,
     arginine or not present
<220> FEATURE:
<221> NAME/KEY: MISC_FEATURE
```

```
<222> LOCATION: (28)..(28)
<223> OTHER INFORMATION: May or may not be present
<220> FEATURE:
<221> NAME/KEY: MOD_RES
<222> LOCATION: (29)..(29)
<223> OTHER INFORMATION: Alanine, glycine, threonine or not present
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MOD_RES
<222> LOCATION: (31)..(40)
<223> OTHER INFORMATION: Alanine, glycine, serine or not present
<220> FEATURE:
<221> NAME/KEY: MISC_FEATURE
<222> LOCATION: (31)..(40)
<223> OTHER INFORMATION: This region may encompass 2 to 10 amino acids,
      wherein some positions may be absent
<220> FEATURE:
<221> NAME/KEY: MISC_FEATURE
<222> LOCATION: (41)..(60)
<223> OTHER INFORMATION: This region may encompass 8 to 20 amino acids
      including "KRNRNNIA" or "GPSSGAPPPS" or "GPSSGAPPPSK" or
      "HSQGTFTSDYSKYLD" or "HSQGTFTSDYSRYLDK" or "HGEGTFTSDLSKQMEEEAVK,
      "wherein some or all positions may be absent
<220> FEATURE:
<223> OTHER INFORMATION: See specification as filed for detailed
      description of substitutions and preferred embodiments

<400> SEQUENCE: 50

Xaa Xaa Xaa Gly Thr Phe Thr Ser Asp Xaa Xaa Xaa Xaa Xaa Xaa
1               5                   10                  15

Xaa Xaa Xaa Xaa Xaa Phe Xaa Xaa Trp Xaa Xaa Asn Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa
        50                  55                  60

<210> SEQ ID NO 51
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MISC_FEATURE
<222> LOCATION: (2)..(29)
<223> OTHER INFORMATION: This region may encompass 26 to 28 amino acids
      including "SQGTFTSDYSKYLDSRRAQDFVQWLMNT" or
      "SQGTFTSDYSKYLDEEAVRLFIEWLMNT" or "SQGTFTSDYSKYLDERRAQDFVAWLKNT"
      or "GQGTFTSDYSRYLEEEAVRLFIEWLKNG" or
      "GQGTFTSDYSRQMEEEAVRLFIEWLKNG"
<220> FEATURE:
<221> NAME/KEY: MISC_FEATURE
<222> LOCATION: (2)..(29)
<223> OTHER INFORMATION: Continued from above; or
      "GEGTFTSDLSRQMEEEAVRLFIEWAA" or "SQGTFTSDYSRQMEEEAVRLFIEWLMNG,"
      wherein some positions may be absent
<220> FEATURE:
<221> NAME/KEY: MISC_FEATURE
<222> LOCATION: (30)..(40)
<223> OTHER INFORMATION: This region may encompass 8 to 11 amino acids
      including "KRNRNNIA" or "GPSSGAPPPS" or "GPSSGAPPPSK," wherein
      some positions may be absent
<220> FEATURE:
```

<223> OTHER INFORMATION: See specification as filed for detailed
      description of substitutions and preferred embodiments

<400> SEQUENCE: 51

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa
        35                  40

<210> SEQ ID NO 52
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MISC_FEATURE
<222> LOCATION: (2)..(29)
<223> OTHER INFORMATION: This region may encompass 14 to 28 amino acids
      including "SQGTFTSDYSKYLDSRRAQDFVQWLMNT" or
      "SQGTFTSDYSKYLDEEAVRLFIEWLMNT" or "SQGTFTSDYSKYLDERRAQDFVAWLKNT"
      or "GQGTFTSDYSRYLEEEAVRLFIEWLKNG" or
      "GQGTFTSDYSRQMEEEAVRLFIEWLKNG"
<220> FEATURE:
<221> NAME/KEY: MISC_FEATURE
<222> LOCATION: (2)..(29)
<223> OTHER INFORMATION: Continued from above; or
      "GEGTFTSDLSRQMEEEAVRLFIEWAA" or "SQGTFTSDYSRQMEEEAVRLFIEWLMNG"
      or "GEGTFTSDLSRQMEEEAVRLFIEW" or "SQGTFTSDYSRYLD," wherein some
      positions may be absent
<220> FEATURE:
<221> NAME/KEY: MOD_RES
<222> LOCATION: (30)..(39)
<223> OTHER INFORMATION: Alanine, glycine, serine or not present
<220> FEATURE:
<221> NAME/KEY: MISC_FEATURE
<222> LOCATION: (30)..(39)
<223> OTHER INFORMATION: This region may encompass 2 to 10 amino acids,
      wherein some positions may be absent
<220> FEATURE:
<221> NAME/KEY: MISC_FEATURE
<222> LOCATION: (40)..(59)
<223> OTHER INFORMATION: This region may encompass 15 to 20 amino acids
      including "HSQGTFTSDYSKYLD" or "HSQGTFTSDYSRYLDK" or
      "HGEGTFTSDLSKQMEEEAVK," wherein some positions may be absent
<220> FEATURE:
<223> OTHER INFORMATION: See specification as filed for detailed
      description of substitutions and preferred embodiments

<400> SEQUENCE: 52

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa
    50                  55

<210> SEQ ID NO 53
<211> LENGTH: 40

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MOD_RES
<222> LOCATION: (16)..(16)
<223> OTHER INFORMATION: Serine, glutamic acid or arginine
<220> FEATURE:
<221> NAME/KEY: MOD_RES
<222> LOCATION: (17)..(17)
<223> OTHER INFORMATION: Arginine, glutamic acid or serine
<220> FEATURE:
<221> NAME/KEY: MOD_RES
<222> LOCATION: (18)..(18)
<223> OTHER INFORMATION: Arginine, alanine or valine
<220> FEATURE:
<221> NAME/KEY: MOD_RES
<222> LOCATION: (19)..(19)
<223> OTHER INFORMATION: Arginine, valine or serine
<220> FEATURE:
<221> NAME/KEY: MOD_RES
<222> LOCATION: (20)..(20)
<223> OTHER INFORMATION: Glutamine, arginine or lysine
<220> FEATURE:
<221> NAME/KEY: MOD_RES
<222> LOCATION: (26)..(26)
<223> OTHER INFORMATION: Isoleucine, valine or serine
<220> FEATURE:
<221> NAME/KEY: MOD_RES
<222> LOCATION: (27)..(27)
<223> OTHER INFORMATION: Methionine, arginine or glutamine
<220> FEATURE:
<221> NAME/KEY: MOD_RES
<222> LOCATION: (29)..(29)
<223> OTHER INFORMATION: Threonine, glycine or alanine
<220> FEATURE:
<221> NAME/KEY: MISC_FEATURE
<222> LOCATION: (30)..(40)
<223> OTHER INFORMATION: This region may encompass 8 to 11 amino acids
      including "KRNRNNIA" or "GPSSGAPPPS" or "GPSSGAPPPSK," wherein
      some positions may be absent
<220> FEATURE:
<223> OTHER INFORMATION: See specification as filed for detailed
      description of substitutions and preferred embodiments

<400> SEQUENCE: 53

Xaa Ser Gln Gly Thr Phe Thr Ser Asp Tyr Ser Lys Tyr Leu Asp Xaa
1               5                   10                  15

Xaa Xaa Xaa Xaa Leu Phe Val Gln Trp Xaa Xaa Asn Xaa Xaa Xaa Xaa
            20                  25                  30

Xaa Xaa Xaa Xaa Xaa Xaa Xaa Xaa
        35                  40

<210> SEQ ID NO 54
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
```

```
<221> NAME/KEY: MOD_RES
<222> LOCATION: (2)..(2)
<223> OTHER INFORMATION: Serine, Aib, Sarcosine, d-alanine or d-serine
<220> FEATURE:
<221> NAME/KEY: MOD_RES
<222> LOCATION: (16)..(16)
<223> OTHER INFORMATION: Serine or glutamic acid
<220> FEATURE:
<221> NAME/KEY: MOD_RES
<222> LOCATION: (17)..(17)
<223> OTHER INFORMATION: Arginine or lysine
<220> FEATURE:
<221> NAME/KEY: MOD_RES
<222> LOCATION: (20)..(20)
<223> OTHER INFORMATION: Glutamine or lysine
<220> FEATURE:
<221> NAME/KEY: MOD_RES
<222> LOCATION: (21)..(21)
<223> OTHER INFORMATION: Aspartic acid or glutamic acid
<220> FEATURE:
<221> NAME/KEY: MOD_RES
<222> LOCATION: (24)..(24)
<223> OTHER INFORMATION: Glutamine, cysteine or lysine
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MISC_FEATURE
<222> LOCATION: (31)..(41)
<223> OTHER INFORMATION: This region may encompass 8 to 11 amino acids
      including "KRNRNNIA" or "GPSSGAPPPS" or "GPSSGAPPPSK," wherein
      some or all positions may be absent
<220> FEATURE:
<223> OTHER INFORMATION: See specification as filed for detailed
      description of substitutions and preferred embodiments

<400> SEQUENCE: 54

Xaa Xaa Gln Gly Thr Phe Thr Ser Asp Tyr Ser Lys Tyr Leu Asp Xaa
1               5                   10                  15

Xaa Arg Ala Xaa Xaa Phe Val Xaa Trp Leu Met Asn Thr Xaa Xaa Xaa
                20                  25                  30

Xaa Xaa Xaa Xaa Xaa Xaa Xaa Xaa Xaa
            35                  40

<210> SEQ ID NO 55
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, 4-imidazoacetyl
      or tyrosine
<220> FEATURE:
<221> NAME/KEY: MOD_RES
<222> LOCATION: (2)..(2)
<223> OTHER INFORMATION: Aib (aminosiobutyric acid), glycine or serine
<220> FEATURE:
<221> NAME/KEY: MOD_RES
<222> LOCATION: (3)..(3)
<223> OTHER INFORMATION: Glutamic acid or glutamine
<220> FEATURE:
<221> NAME/KEY: MOD_RES
<222> LOCATION: (10)..(10)
<223> OTHER INFORMATION: Leucine or tyrosine
<220> FEATURE:
<221> NAME/KEY: MOD_RES
<222> LOCATION: (11)..(11)
<223> OTHER INFORMATION: Serine or alanine
<220> FEATURE:
<221> NAME/KEY: MOD_RES
```

```
<222> LOCATION: (12)..(12)
<223> OTHER INFORMATION: Lysine or arginine
<220> FEATURE:
<221> NAME/KEY: MOD_RES
<222> LOCATION: (13)..(13)
<223> OTHER INFORMATION: Glutamine or tyrosine
<220> FEATURE:
<221> NAME/KEY: MOD_RES
<222> LOCATION: (14)..(14)
<223> OTHER INFORMATION: Leucine or methionine
<220> FEATURE:
<221> NAME/KEY: MOD_RES
<222> LOCATION: (15)..(15)
<223> OTHER INFORMATION: Aspartic acid or glutamic acid
<220> FEATURE:
<221> NAME/KEY: MOD_RES
<222> LOCATION: (16)..(16)
<223> OTHER INFORMATION: Glutamic acid, alpha-methyl-glutamic acid or
      not present
<220> FEATURE:
<221> NAME/KEY: MOD_RES
<222> LOCATION: (17)..(17)
<223> OTHER INFORMATION: Glutamine, glutamic acid, lysine, arginine or
      not present
<220> FEATURE:
<221> NAME/KEY: MOD_RES
<222> LOCATION: (18)..(18)
<223> OTHER INFORMATION: Alanine, arginine or not present
<220> FEATURE:
<221> NAME/KEY: MOD_RES
<222> LOCATION: (19)..(19)
<223> OTHER INFORMATION: Alanine, valine or not present
<220> FEATURE:
<221> NAME/KEY: MOD_RES
<222> LOCATION: (20)..(20)
<223> OTHER INFORMATION: Lysine, glutamine, arginine, alpha-methyl-
      glutamic acid or not present
<220> FEATURE:
<221> NAME/KEY: MOD_RES
<222> LOCATION: (21)..(21)
<223> OTHER INFORMATION: Aspartic acid, glutamic acid, leucine or not
      present
<220> FEATURE:
<221> NAME/KEY: MISC_FEATURE
<222> LOCATION: (22)..(22)
<223> OTHER INFORMATION: May or may not be present
<220> FEATURE:
<221> NAME/KEY: MOD_RES
<222> LOCATION: (23)..(23)
<223> OTHER INFORMATION: Isoleucine, valine or not present
<220> FEATURE:
<221> NAME/KEY: MOD_RES
<222> LOCATION: (24)..(24)
<223> OTHER INFORMATION: Alanine, cysteine, glutamic acid, glutamine,
      alpha-methyl-glutamic acid or not present
<220> FEATURE:
<221> NAME/KEY: MISC_FEATURE
<222> LOCATION: (25)..(25)
<223> OTHER INFORMATION: May or may not be present
<220> FEATURE:
<221> NAME/KEY: MOD_RES
<222> LOCATION: (26)..(26)
<223> OTHER INFORMATION: Alanine, isoleucine, leucine, valine or not
      present
<220> FEATURE:
<221> NAME/KEY: MOD_RES
<222> LOCATION: (27)..(27)
<223> OTHER INFORMATION: Alanine, lysine, methionine, arginine or not
      present
<220> FEATURE:
<221> NAME/KEY: MISC_FEATURE
<222> LOCATION: (28)..(29)
<223> OTHER INFORMATION: May or may not be present
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MISC_FEATURE
```

```
<222> LOCATION: (31)..(40)
<223> OTHER INFORMATION: This region may encompass 2 to 10 residues,
      wherein some positions may not be present
<220> FEATURE:
<221> NAME/KEY: MISC_FEATURE
<222> LOCATION: (41)..(60)
<223> OTHER INFORMATION: This region may encompass 8 to 20 amino acids
      including "KRNRNNIA" or "GPSSGAPPPS" or "GPSSGAPPPSK" or
      "HSQGTFTSDYSKYLD" or "HSQGTFTSDYSRYLDK" or "HGEGTFTSDLSKQMEEEAVK,
      " wherein some or all positions may be absent
<220> FEATURE:
<223> OTHER INFORMATION: See specification as filed for detailed
      description of substitutions and preferred embodiments

<400> SEQUENCE: 55

Xaa Xaa Xaa Gly Thr Phe Thr Ser Asp Xaa Xaa Xaa Xaa Xaa Xaa
1               5                   10                  15

Xaa Xaa Xaa Xaa Xaa Phe Xaa Xaa Trp Xaa Xaa Asn Thr Xaa Gly Gly
            20                  25                  30

Gly Gly Gly Gly Gly Gly Gly Gly Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60
```

LIQUID FORMULATION OF PROTEIN CONJUGATE COMPRISING AN OXYNTOMODULIN DERIVATIVE COVALENTLY LINKED TO A NON-PEPTIDYL POLYMER TO AN IMMUNOGLOBULIN FC REGION

CROSS REFERENCE TO RELATED APPLICATIONS

This application is a National Stage of International Application No. PCT/KR2013/009986, filed Nov. 6, 2013, claiming priority based on Korean Patent Application No. 10-2012-0124725, filed Nov. 6, 2012, the contents of all of which are incorporated herein by reference in their entirety.

SEQUENCE LISTING

The instant application contains a Sequence Listing which has been submitted electronically in ASCII format and is hereby incorporated by reference in its entirety. The ASCII copy, created on Aug. 17, 2016, is named 106132_000151_SL.txt and is 39,505 bytes in size.

TECHNICAL FIELD

The present invention relates to an albumin-free liquid formulation comprising a long-lasting oxyntomodulin conjugate in which an oxyntomodulin peptide comprising a derivative, variant, precursor or fragment of oxyntomodulin is linked to an immunoglobulin Fc region, which can increase the duration of physiological activity of the long-lasting oxyntomodulin conjugate and maintain the in vivo stability thereof for an extended period of time, compared to native oxyntomodulin. The present invention also relates to a method for preparing the liquid formulation.

BACKGROUND ART

Obesity is defined as a condition of abnormal or excessive fat accumulation that may impair health and results from an energy imbalance in which energy intake exceeds energy expenditure. Obesity was not a serious health problem in the past, but with economic growth, the obese population is increasing with increasing economic affluence, and the number of various diseases related to obesity is also increasing. According to the report of the World Health Organization (WHO), over 1.5 billion adults worldwide are overweight, over 500 million of them are obese, and the obesity population increased by about twice between 1980 and 2008 (World Health Organization, Fact sheet on obesity and overweight, 2011). Not only in high-income countries, but also in low-income countries, the percentage of obese people is currently increasing. Overweight and obesity are responsible for increasing blood pressure and cholesterol levels and cause or worsen various diseases. In addition, the obesity problem is more serious in children or teenagers, increases the incidence of diabetes, heart diseases, hypertension or hyperlipidemia, and can also cause deaths or disabilities.

As described above, obesity is a global disease and social problem, but in the past, it was believed that obesity could be overcome by individual efforts, and thus no particular emphasis was placed on the treatment of obesity. However, obesity is not easy to treat, because it is a complex disease associated with the mechanisms of appetite control and energy metabolism. Accordingly, the treatment of obesity requires not only the patient's own efforts, but also a method capable of treating abnormal mechanisms associated with appetite control and energy metabolism. Thus, efforts have been made to develop drugs for treating obesity.

As a result of such efforts, drugs, including Rimonabant (Sanofi-Aventis), Sibutramine (Abbott), Contrave (Takeda), Orlistat (Roche) and the like, were developed, but these drugs have shortcomings in that they show fetal side effects or have an insufficient effect on the treatment of obesity. It was reported that Rimonabant (Sanofi-Aventis) showed disorders of the central nervous system, Sibutramine (Abbott) and Contrave (Takeda) showed cardiovascular side effects, and Orlistat (Roche) showed a weight reduction effect of only about 4 kg when administered for 1 year. Thus, there are currently little or no obesity therapeutic agents that can be safely prescribed for obesity patients.

Recently, glucagon derivatives have received much attention. Glucagon is produced by the pancreas when blood glucose levels start to drop due to medications, diseases, hormone or enzyme deficiencies, or the like. Glucagon functions to stimulate liver cells to break down stored glycogen into glucose which is then released into the blood to raise the blood glucose level to a normal level. In addition to the effect of increasing the blood glucose level, glucagon was reported to suppress appetite and activate hormone-sensitive lipase (HSL) of adipocytes to facilitate lipolysis, thereby showing anti-obesity effects. Among the glucagon derivatives, glucagon-like peptide-1 (GLP-1) is under development as a therapeutic agent for reducing hyperglycemia in diabetic patients and functions to stimulate insulin synthesis and secretion, inhibit glucagon secretion, suppress gastric emptying, increase glucose utilization and inhibit food intake. It is known that exendin-4 that is isolated from lizard venom has an amino acid homology of about 50% with GLP-1 and activates the GLP-1 receptor to reduce hyperglycemia in diabetic patients. However, obesity therapeutic drugs, including GLP-1, were reported to cause side effects such as vomiting and nausea.

Thus, as an alternative to GLP-1, oxyntomodulin capable of binding to both receptors for two peptides (GLP-1 and glucagon) is receiving attention. Oxyntomodulin is a peptide made from pre-glucagon, a precursor of glucagon, and is a potent anti-obesity agent, because it inhibits food intake, like GLP-1, promotes satiety, and shows lipolytic activity, like glucagon.

Based on the dual function of the oxyntomodulin peptide, studies on the development of drugs for the treatment of obesity have been actively conducted. For example, Korean Patent Registration No. 925017 discloses an oral, parenteral, mucosal, rectal, subcutaneous or transdermal pharmaceutical composition for treating human obesity, which comprises oxyntomodulin as an active ingredient. However, it was reported that obesity therapeutic agents comprising oxyntomodulin have a short in vivo half-life and show a low effect on the treatment of obesity, even when these are administered at a high dose three times a day. Thus, efforts have been made to increase the in vivo half-life or obesity-treating effect of oxyntomodulin by modifying oxyntomodulin.

For example, the dual agonist oxyntomodulin (Merck) is obtained by substituting L-serine with D-serine at amino acid 2 of oxyntomodulin to increase resistance to dipeptidyl peptidase-IV (DPP-IV) and by attaching a cholesterol moiety to the C-terminal to increase the blood half-life. ZP2929 (Zealand) is obtained by substituting L-serine with D-serine at amino acid 2 of oxyntomodulin to increase resistance to DPP-IV, substituting arginine with alanine at amino acid 17 to increase resistance to protease, substituting methionine with lysine at amino acid 27 to increase oxidative stability, and substituting glutamines at amino acids 20 and 24 and asparagine at amino acid 28 with aspartic acid, alanine and serine, respectively, to increase deamidation stability. The dual agonist oxyntomodulin (Merck) has an increased in vivo half-life of 1.7 hours, which is longer than the half-life (8-12 minutes) of native oxyntomodulin, but it still has a very short in vivo half-life and is administered at a very high dose of several mg/kg. Thus, oxyntomodulin or derivatives thereof have two big disadvantages, that is, a short half-life and low medicinal effects. Due to these disadvantages, they should be administered daily at high doses. In order to overcome these disadvantages, a method was studied to increase the blood half-life of oxyntomodulin while maintaining the in vivo activity thereof, and as a result, an oxyntomodulin derivative was developed. In addition, using this technology, a non-peptidyl polymer was prepared by conjugating a carrier to the oxyntomodulin derivative, and it was found that the protein conjugate can show a better anti-obesity effect as a result of increasing the blood half-life thereof while maintaining the in vivo activity (Korean Patent Application No. 10-2012-0064110).

Generally, proteins and peptides have a very short half-life, and undergo denaturation such as precipitation by aggregation of monomers, and adsorption on the surfaces of vessels, upon exposure to various factors such as unfavorable temperatures, water-air interface, high pressure, physical/mechanical stress, organic solvents and microbial contamination. This denaturation is irreversible, and thus the denatured proteins and peptides lose intrinsic physicochemical properties and physiologically active effects. In addition, proteins and peptides are unstable and susceptible to extrinsic factors such as temperature, humidity, oxygen, UV rays or the like to undergo physical or chemical changes including association, polymerization or oxidation, resulting in substantial loss of activity (Korean Patent Registration No. 10-0389726).

Furthermore, the adsorbed proteins and peptides are easily aggregated by the denaturation process, and the denatured proteins and peptides, when administered to the human body, act as the cause of antibody formation in the human body, and for this reason, the proteins and peptides should be administered in a sufficiently stable form. Accordingly, various methods for preventing the denaturation of proteins and peptides in solution have been studied (John Geigert, J. Parenteral Sci. Tech., 43, No 5, 220-224, 1989; David Wong, Pharm. Tech. October 34-48, 1997; Wei Wang., Int. J. Pharm., 185, 129-188, 1999; Willem Norde, Adv. Colloid Interface Sci., 25, 267-340, 1986; Michelle et al., Int. J. Pharm. 120, 179-188, 1995).

Lyophilization is applied to some protein and peptide drugs to achieve the goal of stability. However, lyophilized products are inconvenient in that they must be re-dissolved in injection water for use. In addition, in the case of lyophilization, massive investment on large-capacity freeze-driers or the like is required, because the lyophilization process is included in the production processes. Further, a method for producing powdered proteins and peptides using a spray drier is also being used, but in this case, economic efficiency is decreased due to a low yield, and exposure to high temperatures can adversely affect the stability of the proteins.

In order to overcome such limitations, studies have been conducted in which stabilizers were added to proteins and peptides in solution to suppress the physicochemical changes of the proteins and peptides while maintaining the in vivo efficiency thereof even upon long-term storage. Human serum albumin, a kind of protein, has been widely used as a stabilizer for various protein drugs, and the performance thereof has been proven (Edward Tarelli et al., Biologicals (1998) 26, 331-346).

A process for purifying human serum albumin includes inactivating biological contaminants such as mycoplasma, prion, bacteria and virus and screening or examining one or more biological contaminants or pathogens. However, there is always the risk that patients will be exposed to the biological contaminants that are not completely removed or inactivated. For example, the screening process includes examining whether human blood from donators contains a certain virus, but this process is not always reliable. Particularly, a specific virus existing in a very small number of donators cannot be detected.

Different proteins may be gradually inactivated at different rates under different conditions during storage, due to their chemical differences. That is to say, the extension of the storage term by a stabilizer is not identical for different proteins. For this reason, the suitable ratio, concentration and kind of stabilizer that is used to provide storage stability vary depending on the physicochemical properties of the target protein. When stabilizers are used in combination, they may cause adverse effects different from desired effects due to the competition and interaction therebetween. Further, because the nature or concentration of proteins may change during storage, the stabilizers used may show effects different from those intended. Thus, a great amount of effort and precautions are required to stabilize proteins in solution.

Particularly, a conjugate of oxyntomodulin and immunoglobulin Fc is a conjugate in which oxyntomodulin that is a physiologically active peptide is linked to an immunoglobulin Fc region. Thus, because the molecular weight and volume of the conjugate certainly differ from those of native oxyntomodulin, a special composition for stabilizing the protein is required.

Further, because oxyntomodulin (that is a physiologically active peptide) and the immunoglobulin Fc region are peptides or proteins having different physicochemical properties, they should be simultaneously stabilized. However, as described above, different proteins or proteins may be gradually inactivated at different rates under different conditions during storage, due to their chemical differences, and when stabilizers suitable for proteins or peptides are used in combination, they may cause adverse effects different from the desired effects due to the competition and interaction therebetween. Thus, in the case of a long-lasting oxyntomodulin conjugate, there is much difficulty in finding a composition for simultaneously stabilizing oxyntomodulin, which is a physiologically active peptide, and the immunoglobulin Fc region.

Under such circumstances, the present inventors have made extensive efforts to provide a stable liquid formulation that can be stored for a long period of time without concern about viral contamination, and as a result, have found that a stabilizer, which includes a buffer, a sugar alcohol and a nonionic surfactant and may further include an additive, such as an isotonic agent or an amino acid, and a preservative for repeated use, can increase the stability of a long-lasting oxyntomodulin derivative, and a cost-effective and stable liquid formulation can be prepared using the stabilizer, thereby completing the present invention.

DISCLOSURE

Technical Problem

It is an object of the present invention to provide a liquid formulation of a long-lasting oxyntomodulin conjugate, comprising a pharmacologically effective amount of a long-lasting oxyntomodulin conjugate wherein an oxyntomodulin which is a physiologically active peptide is linked to an immunoglobulin Fc region; and an albumin-free stabilizer.

Another object of the present invention is to provide a method for preparing the above liquid formulation.

Still another object of the present invention is to provide a composition for preventing or treating obesity or diabetes, comprising a liquid oxyntomodulin conjugate formulation comprising physiologically active peptide oxyntomodulin linked to an immunoglobulin Fc region.

Still another object of the present invention is to provide a method for preventing or treating obesity or diabetes, comprising administering the above liquid formulation to a subject.

Technical Solution

To achieve the above objects, in one aspect, the present invention provides a liquid formulation of a long-lasting oxyntomodulin conjugate, comprising a pharmacologically effective amount of a long-lasting oxyntomodulin conjugate wherein an oxyntomodulin which is a physiologically active peptide is linked to an immunoglobulin Fc region; and an albumin-free stabilizer, wherein the stabilizer contains a buffer, a sugar alcohol and a nonionic surfactant.

As used herein, the term "liquid formulation" refers to a drug formulation processed into a liquid form and is intended to include all liquid formulations for internal use and formulations for external use. In the prior art, the inventive liquid formulation suitable for a pharmacologically effective amount of the oxyntomodulin conjugate comprising oxyntomodulin linked to the immunoglobulin Fc domain was not reported. Thus, the liquid formulation of the present invention may comprise a pharmacologically effective amount of the oxyntomodulin conjugate comprising oxyntomodulin linked to the immunoglobulin Fc domain, and an albumin-free stabilizer, wherein the stabilizer contains a buffer, a sugar alcohol and a nonionic surfactant. In addition, the liquid formulation of the present invention may further comprise a preservative.

In the present invention, the stabilizer may further comprise one or more components selected from the group consisting of isotonic agents, sugars, polyhydric alcohols, and amino acids. The sugar alcohol may be one or more selected from the group consisting of mannitol, sorbitol and glycerol, and the concentration of the sugar alcohol in the liquid formulation may be 2-15% (w/v). Further, the buffer may be one or more selected from the group consisting of citrate, acetate, histidine and phosphate buffers and may have a pH ranging from 4.5 to 7.0. The isotonic agent may be sodium chloride, and the nonionic surfactant may be polysorbate or poloxamer and be present at a concentration of 0.001-0.1% (w/v). The amino acid may be methionine. Thus, the liquid formulation of the present invention may comprise a stabilizer that contains a buffer having a pH ranging from 4.8 to 6.0, one or more sugar alcohols selected from the group consisting of mannitol and sorbitol, and polysorbate 20.

In addition, the liquid formulation of the present invention may further comprise one or more preservatives selected from the group consisting of m-cresol, phenol and benzyl alcohol. The concentration of the preservative in the liquid formulation may be 0.001-1% (w/v).

Particularly, the liquid formulation of the present invention may comprise a pharmacologically effective amount of the long-lasting oxyntomodulin conjugate, 5-50 mM histidine, 2-15% (w/v) of mannitol, 0.01-1 mg/mL of methionine and 0.001-0.1% (w/v) of polysorbate 20. In addition to these components, the liquid formulation may further comprise 0.001-1% (w/v) of m-cresol.

As used herein, the term "stabilizer" refers to a substance that stably maintains ingredients such as active ingredients for a specific period of time. For the purpose of the present invention, the term refers to a substance that enables the long-lasting oxyntomodulin conjugate to be stably stored. The storage stability of proteins such as the long-lasting oxyntomodulin conjugate is important not only to guarantee a precise dose, but also to inhibit the potential production of an antigenic substance for the oxyntomodulin derivative conjugate.

The stabilizer in the present invention preferably contains a buffer, a sugar alcohol and a nonionic surfactant in order to impart stability to the long-lasting oxyntomodulin conjugate. In addition, the stabilizer may preferably further comprise one or more components selected from the group consisting of isotonic agents, sugars, polyhydric alcohols and amino acids.

The buffer functions to maintain the pH of the liquid formulation so that the pH of the liquid formulation does not rapidly change so as to make the long-lasting oxyntomodulin conjugate stable. Examples of the buffer may include pharmaceutically acceptable pH buffers, including an alkali salt (sodium phosphate, potassium phosphate, or a hydrogen or dihydrogen salt thereof), sodium citrate, citric acid, sodium acetate, acetic acid, and histidine, or a mixture of these buffers may also be used. The buffer is preferably a citrate or histidine buffer, and more preferably a histidine buffer. The concentration of the buffer is preferably 5-100 mM, and more preferably 5-50 mM. The pH of the buffer is preferably 4.0-8.0, more preferably 4.5-7.0, and even more preferably 5.0-6.0.

In an example of the present invention, the stability of the long-lasting oxyntomodulin conjugate according to the pH of the buffer of the liquid formulation was measured. That is, after the long-lasting oxyntomodulin conjugate was stored at 25° C. for 0-4 weeks while changing the pH of the buffer, the remaining amount of the conjugate was analyzed, and as a result, it was shown that the oxyntomodulin conjugate was more stable at pH 5.6, pH 5.8 and pH 6.0 (Example 3, Tables 2 to 5, Example 7, Tables 18 to 21, Example 8 and Tables 22 to 25). Thus, it was found that the pH of the most stable buffer in the present invention ranges from 5.0 to 6.0. In an example of the present invention, the stability of the long-lasting oxyntomodulin conjugate according to the kind of buffer of the liquid formulation was measured. Specifically, after the oxyntomodulin conjugate was stored with 0.02% polysorbate 20, 0.1 mg/mL of methionine and 5% mannitol at 25° C. for 0-4 weeks, the remaining amount of the conjugate was analyzed. The results of SE-HPLC analysis indicated that the remaining amount of the conjugate did not greatly differ between the buffers at the same pH. The results of IE-HPLC or RP-HPLC analysis indicated that histidine was most stable at the same pH (Example 8 and Tables 22 to 25).

The sugar alcohol functions to increase the stability of the long-lasting oxyntomodulin conjugate. In the present invention, the sugar alcohol may be one or more selected from the group consisting of mannitol, sorbitol and glycerol. Preferably, the sugar alcohol may be mannitol. The concentration of the sugar alcohol in the liquid formulation is preferably 1-20% (w/v), and more preferably 2-15% (w/v).

In an example of the present invention, the influence of the kind of sugar alcohol as a stabilizer on the stability of the long-lasting oxyntomodulin conjugate was analyzed. Specifically, the oxyntomodulin conjugate was stored in citrate buffer (pH 5.6) at 25° C. for 0-4 weeks, and then analyzed by IE-HPLC, SE-HPLC and RP-HPLC. As a result, the conjugate was more stable in the presence of mannitol or sorbitol than in the presence of glycerol at the same concentration. The results of RP-HPLC analysis indicated that the conjugate was a little more stable in the presence of mannitol compared to the presence of sorbitol (Example 4 and Tables 6 to 9). In other words, it was shown that the addition of mannitol or sorbitol showed excellent stability, but the conjugate was most stable in the presence of mannitol.

In an example of the present invention, the influence of the concentration of the sugar alcohol as a stabilizer on the stability of the long-lasting oxyntomodulin conjugate was analyzed. Specifically, the oxyntomodulin conjugate was stored at 25° C. for 0-4 weeks, and then analyzed by IE-HPLC, SE-HPLC and RP-HPLC. As a result, in the presence of 2% mannitol or 15% mannitol, a protein precipitate was produced, and in the presence of 5% mannitol or 10% mannitol, the conjugate was stable (Example 5, Tables 10 to 13, Example 7 and Tables 18 to 21).

The nonionic surfactant functions to lower the surface tension of the protein solution to prevent the protein from being adsorbed onto a hydrophobic surface or from aggregating. Preferred examples of a nonionic surfactant that may be used in the present invention include polysorbate-based nonionic surfactants and poloxamer-based nonionic surfactants, which may be used alone or in combination of two or more. It is not proper that the nonionic surfactant is used at high concentrations in the liquid formulation. The liquid formulation of the present invention contains the nonionic surfactant at a concentration of 0.2% (w/v) or less, and preferably 0.001-0.1% (w/v).

The stabilizer of the present invention may contain an amino acid such as methionine. Methionine functions to additionally stabilize the protein by inhibiting the production of impurities that can be caused by, for example, the oxidative reaction of the protein.

In an example of the present invention, the influence of the concentration of the nonionic surfactant as a stabilizer and the presence or absence of an amino acid on the stability of the long-lasting oxyntomodulin conjugate was tested. Specifically, the oxyntomodulin conjugate was stored in citrate buffer (pH 5.6) and 10% mannitol at 25° C. for 0-4 weeks, and then analyzed by IE-HPLC, SE-HPLC and RP-HPLC. As a result, the oxyntomodulin conjugate was most stable in the presence of 0.02% polysorbate 20 and 0.1 mg/mL of methionine (Example 6 and Tables 14 to 17).

The isotonic agent functions to maintain osmotic pressure a suitable level when administering the long-lasting oxyntomodulin conjugate in solution in vivo and may additionally function to further stabilize the long-lasting oxyntomodulin conjugate in solution. Typical examples of the isotonic agent include water-soluble inorganic salts, such as sodium chloride, sodium sulfate, sodium citrate and the like. The concentration of the isotonic agent is preferably 0-200 mM, and the content thereof can be suitably controlled.

The stabilizer of the present invention preferably contains no albumin. Human serum albumin that can be used as a protein stabilizer is prepared from human blood, and thus can be contaminated with human pathogenic virus, and gelatin or bovine serum albumin can cause diseases or can cause allergic reactions in some patients. The albumin-free stabilizer of the present invention does not contain a foreign protein such as human or animal serum albumin or purified gelatin, and thus is not susceptible to viral infection.

Preferred examples of sugars among the sugars and polyhydric alcohols that may additionally be used to increase the storage stability of the long-lasting oxyntomodulin conjugate include monosaccharides such as mannose, glucose, fucose and xylose, and polysaccharides such as lactose, maltose, sucrose, raffinose and dextran, and preferred examples of the polyhydric alcohols include polypropylene, low-molecular-weight polyethylene glycol, glycerol, low-molecular-weight polypropylene glycol and the like. These sugars and polyhydric alcohols may be used alone or in combination of two or more.

In addition to the above-described buffer, isotonic agent, sugar alcohol, amino acid and nonionic surfactant, the liquid formulation of the present invention may further comprise other components or substances known in the art within a range that does not impair the effect of the present invention.

The inventive liquid formulation of a long-lasting oxyntomodulin conjugate comprises a pharmacologically effective amount of the long-lasting oxyntomodulin conjugate comprising physiologically active peptide oxyntomodulin linked to a immunoglobulin Fc region, and an albumin-free stabilizer, wherein the stabilizer may contain a buffer having a pH ranging from 4.8 to 7.0, one or more sugar alcohol selected from the group consisting of mannitol and sorbitol, and polysorbate 20. More specifically, the stabilizer may contain a buffer having a pH ranging from 5.0 to 6.0, mannitol and polysorbate 20. In addition, the stabilizer may further comprise one or more components selected from the group consisting of isotonic agents, sugars, polyhydric alcohols and amino acids.

The inventive albumin-free liquid formulation containing a high concentration of the long-lasting oxyntomodulin conjugate, which imparts stability to the long-lasting oxyntomodulin conjugate, is not susceptible to viral infection, is simple and shows excellent storage stability, and thus can be provided in an economical manner compared to other stabilizers or lyophilized formulations.

In addition, because the liquid formulation of the present invention comprises the long-lasting oxyntomodulin conjugate that has physiological activity for an extended period of time compared to native oxyntomodulin, it can maintain protein activity in the human body for an extended period of time compared to conventional oxyntomodulin formulations, and thus can be used as an efficient drug formulation. In addition, the liquid formulation of the present invention imparts excellent stability even to a high concentration of the long-lasting oxyntomodulin conjugate.

As used herein, the term "oxyntomodulin" refers to a peptide produced from pre-glucagon that is a precursor of glucagon. In the present invention, oxyntomodulin is meant to include native oxyntomodulin and its precursor, derivative, fragment and variant. Preferably, oxyntomodulin has an amino acid sequence of SEQ ID NO: 1 (HSQGTFTSDYSKYLDSRRAQDFVQWLMNTKRNRNNIA).

As used herein, the term "oxyntomodulin derivative" is meant to include a peptide, a peptide derivative or a peptide mimic that is obtained by the addition, deletion or substitution of amino acids in the amino acid sequence of oxyntomodulin and can activate the glucagon and GLP-1 receptors at a higher level than that activated by native oxyntomodulin. In the present invention, the oxyntomodulin derivative may have any one of amino acid sequences of SEQ ID NOS: 2 to 34. Preferably, the oxyntomodulin derivative may have an amino acid sequence of SEQ ID NO:

23 or 25. More preferably, it may have an amino acid sequence of SEQ ID NO: 25.

As used herein, the term "oxyntomodulin fragment" refers to a fragment having one or more amino acids at the amino or carboxyl terminal end of native oxyntomodulin, in which the added amino acids may also be non-naturally occurring amino acids (e.g., D-type amino acid). This oxyntomodulin fragment has a function of regulating blood glucose levels in vivo.

As used herein, the term "oxyntomodulin variant" is a peptide that has one or more amino acid residues different from those of the amino acid sequence of native oxyntomodulin and possesses a function of activating the GLP-1 and glucagon receptors. The oxyntomodulin variant can be prepared by any one of substitution, addition, deletion, modification, or a combination thereof of some amino acids in the amino acid sequence of native oxyntomodulin.

Methods for preparing the oxyntomodulin variant, derivative and fragment may be used alone or in combination. For example, the present invention also includes a peptide, which has one or more amino acids different from those of native oxyntomodulin and deamination of the N-terminal amino acid residues and has a function of activating both GLP-1 receptor and glucagon receptor.

Amino acids mentioned herein are abbreviated according to the nomenclature rules of IUPAC-IUB as follows:

Alanine A;
Arginine R;
Asparagine N;
Aspartic acid D;
Cysteine C;
Glutamic acid E;
Glutamine Q;
Glycine G;
Histidine H;
Isoleucine I;
Leucine L;
Lysine K;
Methionine M;
Phenylalanine F
Proline P;
Serine S;
Threonine T;
Tryptophan W;
Tyrosine Y;
Valine V.

In the present invention, the oxyntomodulin derivative encompasses any peptide, which is prepared by the substitution, addition, deletion or post-translational modification (e.g., methylation, acylation, ubiquitination, or intramolecular covalent bonding) of amino acids in the amino acid sequence of SEQ ID NO: 1 and can activate both the glucagon and GLP-1 receptors. For substitution or addition of the amino acids, not only 20 amino acids commonly found in human proteins, but also atypical or non-naturally occurring amino acids can be used. Commercial sources of atypical amino acids include Sigma-Aldrich, ChemPep Inc., and Genzyme Pharmaceuticals. The peptides, which include these amino acids, and atypical peptide sequences may be synthesized and purchased from commercial suppliers, for example, American Peptide Company or Bachem (USA) or Anygen (Korea).

In a specific embodiment of the present invention, the oxyntomodulin derivative of the present invention is a novel peptide including the amino acid sequence of the following formula 1:

R1-X1-X2-GTFTSD-X3-X4-X5-X6-X7-X8-X9-X10-X11-X12-X13-X14-X15-X16-X17-X18-X19-X20-X21-X22-X23-X24-R2 (SEQ ID NO: 50)   Formula 1 wherein
R1 is histidine, desamino-histidyl, dimethyl-histidyl (N-dimethyl-histidyl), beta-hydroxyimidazopropionyl, 4-imidazoacetyl, beta-carboxy imidazopropionyl or tyrosine;
X1 is Aib (aminosiobutyric acid), d-alanine, glycine, Sar (N-methylglycine), serine or d-serine;
X2 is glutamic acid or glutamine;
X3 is leucine or tyrosine;
X4 is serine or alanine;
X5 is lysine or arginine;
X6 is glutamine or tyrosine;
X7 is leucine or methionine;
X8 is aspartic acid or glutamic acid;
X9 is glutamic acid, serine or alpha-methyl-glutamic acid or is deleted;
X10 is glutamine, glutamic acid, lysine, arginine or serine or is deleted;
X11 is alanine, arginine or valine or is deleted;
X12 is alanine, arginine, serine or valine or is deleted;
X13 is lysine, glutamine, arginine or alpha-methyl-glutamic acid or is deleted;
X14 is aspartic acid, glutamic acid or leucine or is deleted;
X15 is phenylalanine or is deleted;
X16 is isoleucine or valine or is deleted;
X17 is alanine, cysteine, glutamic acid, lysine, glutamine or alpha-methyl-glutamic acid or is deleted;
X18 is tryptophan or is deleted;
X19 is alanine, isoleucine, leucine, serine or valine or is deleted;
X20 is alanine, lysine, methionine, glutamine or arginine or is deleted;
X21 is asparagine or is deleted;
X22 is alanine, glycine or threonine or is deleted;
X23 is cysteine or lysine or is deleted;
X24 is a peptide having 2 to 10 amino acids consisting of a combination of alanine, glycine and serine or is deleted; and
R2 is KRNRNNIA (SEQ ID NO: 35), GPSSGAPPPS (SEQ ID NO: 36), GPSSGAPPPSK (SEQ ID NO: 37), HSQGTFTSDYSKYLD (SEQ ID NO: 38), HSQGTFTSDYSRYLDK (SEQ ID NO: 39), HGEGTFTSDLSKQMEEEAVK (SEQ ID NO: 40) or is deleted (with the exception of the case in which the amino acid sequence of formula 1 is identical to that of SEQ ID NO: 1).

In order to increase the activity of wild-type oxyntomodulin for the glucagon receptor and the GLP-1 receptor, the oxyntomodulin derivative of the present invention may be substituted with 4-imidazoacetyl obtained by deletion of the alpha carbon of histidine at position 1 of the amino acid sequence of SEQ ID NO: 1, desamino-histidyl obtained by deletion of the N-terminal amino group, dimethyl-histidyl (N-dimethyl-histidyl) obtained by modification of the N-terminal amino group with two methyl groups, beta-hydroxy imidazopropionyl obtained by substitution of the N-terminal amino group with a hydroxyl group, or beta-carboxy imidazopropionyl obtained by substitution of the N-terminal amino group with a carboxyl group. In addition, the GLP-1 receptor-binding region may be substituted with amino acids that enhance hydrophobic and ionic bonds or a combination thereof. Further, a portion of the oxyntomodulin sequence may be substituted with the amino acid sequence of GLP-1 or Exendin-4 to increase the activity of the GLP-1 receptor.

Moreover, a portion of the oxyntomodulin sequence may be substituted with a sequence that enhances alpha helix. Preferably, amino acids at positions 10, 14, 16, 20, 24 and 28 of the amino acid sequence of formula 1 may be substituted with amino acids or amino acid derivatives consisting of Tyr(4-Me), Phe, Phe(4-Me), Phe(4-Cl), Phe(4-CN), Phe(4-NO$_2$), Phe(4-NH$_2$), Phg, Pal, Nal, Ala(2-thienyl) and Ala(benzothienyl) that are known to stabilize alpha helix, and the type and number of alpha helix-stabilizing amino acid or amino acid derivatives to be inserted are not limited. Preferably, amino acids at positions 10 and 14, 12 and 16, 16 and 20, 20 and 24, and 24 and 28 of the amino acid sequence may also be substituted with glutamic acid or lysine so as to form rings, and the number of rings to be inserted is not limited. Most preferably, the oxyntomodulin derivative may have an amino acid sequence selected from among the following formulas 2 to 6.

In a specific embodiment, the oxyntomodulin derivative of the present invention is a novel peptide including the amino acid sequence of the following formula 2, obtained by substitution of the amino acid sequence of oxyntomodulin with that of exendin or GLP-1:

R1-A-R3 (SEQ ID NO: 51)    Formula 2

In another specific embodiment, the oxyntomodulin derivative of the present invention is a novel peptide including the amino acid sequence of the following formula 3, which is prepared by linking a portion of the amino acid sequence of oxyntomodulin and a portion of the amino acid sequence of exendin or GLP-1 via a proper amino acid linker:

R1-B-C-R4 (SEQ ID NO: 52)    Formula 3

In still another specific embodiment, the oxyntomodulin derivative of the present invention is a novel peptide including the amino acid sequence of the following formula 4, wherein a portion of the amino acid sequence of oxyntomodulin is substituted with an amino acid that enhances the hydrophobic binding to GLP-1 receptor. For example, it is a peptide wherein Leu at position 26 is substituted with the amino acid Ile or Val that increases hydrophobicity.

R1-SQGTFTSDYSKYLD-D1-D2-D3-D4-D5-LFVQW-D6-D7-N-D8-R3 (SEQ ID NO:    Formula 4

In still another specific embodiment, the oxyntomodulin derivative of the present invention is a novel peptide including the amino acid sequence of the following formula 5, wherein a portion of the amino acid sequence of native oxyntomodulin is deleted, added, or substituted with other amino acids in order to increase the abilities of native oxyntomodulin to activate GLP-1 receptor and glucagon receptor:

R1-E1-QGTFTSDYSKYLD-E2-E3-RA-E4-E5-FV-E6-WLMNT-E7-R5 (SEQ ID NO: 54)    Formula 5

In formulas 2 to 5, R1 is as described in formula 1;
A is selected from the group consisting of

```
                                        (SEQ ID NO: 41)
SQGTFTSDYSKYLDSRRAQDFVQWLMNT, (SEQ ID NO: 42)
SQGTFTSDYSKYLDEEAVRLFIEWLMNT, (SEQ ID NO: 43)
SQGTFTSDYSKYLDERRAQDFVAWLKNT, (SEQ ID NO: 44)
GQGTFTSDYSRYLEEEAVRLFIEWLKNG, (SEQ ID NO: 45)
GQGTFTSDYSRQMEEEAVRLFIEWLKNG, (SEQ ID NO: 46)
GEGTFTSDLSRQMEEEAVRLFIEWAA,
and (SEQ ID NO: 47)
SQGTFTSDYSRQMEEEAVRLFIEWLMNG;
```

B is selected from the group consisting of

```
                                        (SEQ ID NO: 41)
SQGTFTSDYSKYLDSRRAQDFVQWLMNT, (SEQ ID NO: 42)
SQGTFTSDYSKYLDEEAVRLFIEWLMNT, (SEQ ID NO: 43)
SQGTFTSDYSKYLDERRAQDFVAWLKNT, (SEQ ID NO: 44)
GQGTFTSDYSRYLEEEAVRLFIEWLKNG, (SEQ ID NO: 45)
GQGTFTSDYSRQMEEEAVRLFIEWLKNG, (SEQ ID NO: 46)
GEGTFTSDLSRQMEEEAVRLFIEWAA, (SEQ ID NO: 47)
SQGTFTSDYSRQMEEEAVRLFIEWLMNG, (SEQ ID NO: 48)
GEGTFTSDLSRQMEEEAVRLFIEW,
and (SEQ ID NO: 49)
SQGTFTSDYSRYLD;
```

C is a peptide having 2 to 10 amino acids consisting of a combination of alanine, glycine and serine;
D1 is serine, glutamic acid or arginine;
D2 is arginine, glutamic acid or serine;
D3 is arginine, alanine or valine;
D4 is arginine, valine or serine;
D5 is glutamine, arginine or lysine;
D6 is isoleucine, valine or serine;
D7 is methionine, arginine or glutamine;
D8 is threonine, glycine or alanine;
E1 is serine, Aib, Sar, d-alanine or d-serine;
E2 is serine or glutamic acid;
E3 is arginine or lysine;
E4 is glutamine or lysine;
E5 is aspartic acid or glutamic acid;
E6 is glutamine, cysteine or lysine;
E7 is cysteine or lysine or is deleted;
R3 is KRNRNNIA (SEQ ID NO: 35), GPSSGAPPPS (SEQ ID NO: 36) or GPSSGAPPPSK (SEQ ID NO: 37);
R4 is HSQGTFTSDYSKYLD (SEQ ID NO: 38), HSQGTFTSDYSRYLDK (SEQ ID NO: 39) or HGEGTFTSDLSKQMEEEAVK (SEQ ID NO: 40); and,
R5 is KRNRNNIA (SEQ ID NO: 35), GPSSGAPPPS (SEQ ID NO: 36) or GPSSGAPPPSK (SEQ ID NO: 37) or is deleted (with the exception of the case in which the amino acid sequences of formulas 2 to 5 are identical to that of SEQ ID NO: 1).

Preferably, the oxyntomodulin derivative of the present invention may be a novel peptide of the following formula 6:

R1-X1-X2-GTFTSD-X3-X4-X5-X6-X7-X8-X9-X10-X11-X12-X13-X14-X15-X16-X17-X18-X19-X20-X21-X22-X23-X24-R2 (SEQ ID NO: 55)   Formula 6 wherein R1 is histidine, desamino-histidyl, 4-imidazoacetyl or tyrosine;
X1 is Aib(aminosiobutyric acid), glycine or serine;
X2 is glutamic acid or glutamine;
X3 is leucine or tyrosine;
X4 is serine or alanine;
X5 is lysine or arginine;
X6 is glutamine or tyrosine;
X7 is leucine or methionine;
X8 is aspartic acid or glutamic acid;
X9 is glutamic acid or alpha-methyl-glutamic acid or is deleted;
X10 is glutamine, glutamic acid, lysine or arginine or is deleted;
X11 is alanine or arginine or is deleted;
X12 is alanine or valine or is deleted;
X13 is lysine, glutamine, arginine or alpha-methyl-glutamic acid or is deleted;
X14 is aspartic acid, glutamic acid or leucine or is deleted;
X15 is phenylalanine or is deleted;
X16 is isoleucine or valine or is deleted;
X17 is alanine, cysteine, glutamic acid, glutamine or alpha-methyl-glutamic acid or is deleted;
X18 is tryptophan or is deleted;
X19 is alanine, isoleucine, leucine or valine or is deleted;
X20 is alanine, lysine, methionine or arginine or is deleted;
X21 is asparagine or is deleted;
X22 is threonine or is deleted;
X23 is cysteine, lysine or is deleted;
X24 is a peptide having 2 to 10 amino acids consisting of glycine or is deleted; and
R2 is KRNRNNIA (SEQ ID NO: 35), GPSSGAPPPS (SEQ ID NO: 36), GPSSGAPPPSK (SEQ ID NO: 37), HSQGTFTSDYSKYLD (SEQ ID NO: 38), HSQGTFTSDYSRYLDK (SEQ ID NO: 39) or HGEGTFTSDLSKQMEEEAVK (SEQ ID NO: 40) or is deleted (with the exception of the case in which the amino acid sequence of formula 6 is identical to that of SEQ ID NO: 1).

More preferably, the oxyntomodulin derivative of the present invention may be selected from the group consisting of the peptides of SEQ ID NOs: 2 to 34. Even more preferably, the oxyntomodulin derivative of the present invention may be an oxyntomodulin derivative described in Table 1 of Example 1.

Oxyntomodulin has the activities of two peptides, GLP-1 and glucagon. GLP-1 has the effect of lowering blood glucose levels by insulin secretion, but glucagon has the effect of increasing blood glucose levels. Further, GLP-1 inhibits food intake and suppresses gastric emptying, and glucagon has the effect of reducing bodyweight by facilitating lipolysis and increasing energy metabolisms. Thus, GLP-1 and glucagon have different biological effects. Thus, in the case in which the two peptides present as a conjugate, if the effect of any one of the two peptides is greater than that of the other, an adverse effect can occur. For example, if the effect of glucagon is greater than that of GLP-1, blood glucose levels can rise, and if the effect of GLP-1 is greater than that of glucagon, side effects such as nausea and vomiting can occur. In addition, the effect of the two peptides may vary depending on the ratio of the activities of the two peptides. Thus, the oxyntomodulin derivatives and their conjugates are not limited only to derivatives having increased activities.

As used herein, the term "oxyntomodulin conjugate" refers to a conjugate comprising oxyntomodulin and another element. The other element may be any substance having beneficial functions, including increasing the blood half-life of oxyntomodulin or delaying the release of oxyntomodulin into the kidneys. The conjugate of the present invention can bind covalently to oxyntomodulin or form microspheres to increase the serum stability of oxyntomodulin or to delay the release of oxyntomodulin into the kidneys or to change the binding activity of oxyntomodulin to its receptor. The carrier that can form a conjugate comprising oxyntomodulin may be selected from the group consisting of albumin, transferrin, antibodies, antibody fragments, elastin, heparin, polysaccharide such as chitin, fibronectin, and the like, which can bind to oxyntomodulin to increase the serum stability of oxyntomodulin. Preferably, the carrier is an immunoglobulin Fc region.

The immunoglobulin Fc that may be used in the present invention may be a human immunoglobulin Fc, an immunoglobulin Fc having the sequence of an analogue thereof, or an immunoglobulin Fc derived from animals, including cows, goats, pigs, mice, rabbits, hamsters, rats and guinea pigs. Further, the immunoglobulin Fc region may be derived from IgG, IgA, IgD, IgE, IgM, or a combination or hybrid thereof. Further, each domain of the immunoglobulin Fc region of the present invention may be a hybrid of domains originated from different immunoglobulins selected from the group consisting of IgG, IgA, IgD, IgE, and IgM. Alternatively, the immunoglobulin Fc region is a dimer or multimer consisting of single-chain immunoglobulins composed of domains of the sane origin. Preferably, the immunoglobulin Fc region is one derived from IgG or IgM, which is most rich in human blood. Most preferably, it is an immunoglobulin Fc derived from IgG known to increase the half-life of ligand-binding proteins. The immunoglobulin Fc may be prepared either by treating native IgG with a specific protease or from transformed cells using recombination technique. Preferably, it is a recombinant human immunoglobulin Fc prepared in E. coli.

Meanwhile, IgG can also be sub-classified into IgG1, IgG2, IgG3 and IgG4, and in the present invention, a combination or hybrid of these subclasses is also possible. Preferably, IgG is the IgG2 ad IgG4 subclass, and most preferably, it is the Fc region of IgG4 that substantially lacks effector functions such as complement-dependent cytotoxicity (CDC). In other words, the most preferred immunoglobulin Fc region that is used as a drug carrier in the present invention is a non-glycosylated Fc region derived from human IgG4. A human-derived Fc region is more preferable than a non-human-derived Fc region, which may act as an antigen in the human body and cause undesirable immune responses such as the production of a new antibody against the antigen.

In the present invention, the oxyntomodulin conjugate may be prepared by using a non-peptidyl polymer or by gene recombination technique. Preferably, the conjugate may be prepared by linking oxyntomodulin to the immunoglobulin Fc region by a non-peptidyl polymer.

The non-peptidyl polymer may be linked to each of oxyntomodulin and the immunoglobulin Fc region. Each end of the non-peptidyl polymer may be linked to the immunoglobulin Fc region and the amine or thiol group of the oxyntomodulin derivative, respectively.

As used herein, the term "oxyntomodulin conjugate" refers to one having an increased long-lasting effect compared to native oxyntomodulin. Examples of the long-lasting conjugate include, but are not limited to, a conjugate in which a oxyntomodulin derivative resulting from the modification, substitution, addition or deletion of amino acids in the amino acid sequence of native oxyntomodulin is linked to a biodegradable polymer such as polyethylene glycol (PEG), a conjugate in which a protein having excellent long-lasting properties, such as albumin or immunoglobulin, is linked to oxyntomodulin, a conjugate in which a fatty acid having ability to bind to albumin in vivo is linked to oxyntomodulin, or a conjugate in which oxyntomodulin is encapsulated in biodegradable nanoparticles.

As used herein, the term "non-peptidyl polymer" refers to a biocompatible polymer including two or more repeating units linked to each other by any covalent bond in place of a peptide bond. In the present invention, the non-peptidyl polymer may be used interchangeably with the non-peptidyl linker.

A peptide linker that is used in a fusion protein obtained by a conventional inframe fusion method has drawbacks in that it is easily cleaved by proteinase in vivo, and thus the desired effect of increasing the serum half-life of the active drug by a carrier cannot be obtained. However, in the present invention, the polymer having resistance to proteinase can be used to maintain the serum half-life of the peptide, similar to the carrier. Therefore, any non-peptidyl polymer can be used without limitation in the present invention, as long as it is a polymer having the aforementioned function, that is, a polymer having resistance to proteinase in vivo. The non-peptidyl polymer has a molecular weight in the range of 1 to 100 kDa, and preferably 1 to 20 kDa. The non-peptidyl polymer of the present invention, which is linked to the immunoglobulin Fc region, may be one kind of polymer or a combination of different polymers.

The non-peptidyl polymer that is used in the present invention may have a reactive group capable of binding to the immunoglobulin Fc region and the protein drug. The reactive group at both ends of the non-peptidyl polymer is preferably selected from the group consisting of a reactive aldehyde group, a propionaldehyde group, a butyraldehyde group, a maleimide group and a succinimide derivative.

The succinimide derivative may be succinimidyl propionate, hydroxy succinimidyl, succinimidyl carboxymethyl, or succinimidyl carbonate. In particular, when the non-peptidyl polymer has a reactive aldehyde group at both ends thereof, non-specific reactions can be minimized, and a physiologically active polypeptide and an immunoglobulin can be effectively bound to both ends of the non-peptidyl polymer, respectively. A final product generated by reductive alkylation with an aldehyde bond is much more stable than that linked by an amide bond. The aldehyde reactive group selectively binds to an N-terminus at a low pH and can form a covalent bond with a lysine residue at a high pH such as pH 9.0.

The reactive groups at both ends of the non-peptidyl polymer may be the same or different. For example, the non-peptidyl polymer may possess a maleimide group at one end, and an aldehyde group, a propionaldehyde group or a butyraldehyde group at the other end. When a polyethylene glycol having a reactive hydroxy group at both ends thereof is used as the non-peptidyl polymer, the hydroxy group may be activated to various reactive groups by known chemical reactions, or a polyethylene glycol having a commercially available modified reactive group may be used so as to prepare the long acting conjugate of the present invention.

The conjugate of the present invention may be one in which each end of the non-peptidyl polymer is linked to the immunoglobulin Fc region and the amine or thiol group of the oxyntomodulin derivative, respectively.

Meanwhile, in the present invention, both ends of the non-peptidyl polymer include reactive groups to which an immunoglobulin Fc region and a protein drug can bind. Examples of the reactive groups include, but are not limited to, an aldehyde group, a propionaldehyde group or a butyraldehyde group, a maleimide group, a succinimide derivative (succinimidyl propionate, hydroxyl succinimidyl, succinimidyl carboxymethyl or succinimidyl carbonate) and the like.

The reactive groups at both ends of the linker that is the non-peptidyl polymer may be the same or different. For example, the non-peptidyl polymer may have a maleimide group at one end and an aldehyde group, a propionaldehyde group or a butyraldehyde group at the other end. For example, when the non-peptidyl polymer has a reactive aldehyde group at one end and a reactive maleimide group at the other end, non-specific reactions can be minimized, and a physiologically active polypeptide and an immunoglobulin can be effectively bound to both ends of the non-peptidyl polymer. The non-peptidyl polymer that may be used in the present invention may be selected from the group consisting of polyethylene glycol, polypropylene glycol, an ethylene glycol/propylene glycol copolymer, polyoxyethylated polyol, polyvinyl alcohol, polysaccharides, dextran, polyvinyl ethyl ether, biodegradable polymers such as PLA (poly(lactic acid)) and PLGA (polylactic-glycolic acid), lipid polymers, chitins, hyaluronic acid, and combinations thereof. Preferably, the non-peptidyl polymer is polyethylene glycol. In addition, derivatives thereof known in the art and derivatives that may be easily prepared by a method known in the art are included in scope of the present invention.

In an example of the present invention, a conjugate was synthesized by linking oxyntomodulin or its derivative to the immunoglobulin Fc region via a covalent bond using the non-peptidyl polymer PEG including a propionaldehyde group alone or both a maleimide group and an aldehyde group.

The conjugate of the present invention has excellent GLP-1 receptor and glucagon receptor activities compared to native oxyntomodulin. Also, it has bound thereto an Fc region that increase the in vivo blood half-life thereof to maintain the activity thereof in vivo for an extended period of time.

As used herein, term "preservative" refers to a substance that is used to prevent abnormal reactions or decomposition from being caused by microbial contamination. The liquid formulation of the present invention may further comprise a preservative. A preservative is generally used in multiple-dosage formulations that are most likely contaminated with microorganisms, but is not limited thereto and may also be used in lyophilized formulations or single-dosage formulations to prevent microbial contamination. The liquid formulation of the present invention may comprise one or more preservatives selected from m-cresol, phenol and benzyl alcohol. The concentration of the preservative in the liquid formulation may be 0.001-1% (w/v). Particularly, the preservative that is included in the liquid formulation of the present invention is preferably m-cresol. The liquid formulation of the present invention may be a multiple-dosage formulation.

In another aspect, the present invention provides a method for preparing a liquid formulation of a long-lasting oxyntomodulin conjugate.

Specifically, in one embodiment of the present invention, the method for preparing the liquid formulation may comprise the steps of: a) preparing a long-lasting oxyntomodulin conjugate; and b) mixing the prepared long-lasting oxyntomodulin conjugate with a stabilizer containing a buffer, a sugar alcohol and a non-ionic surfactant.

In another embodiment of the present invention, the method for preparing the liquid formulation may comprise the steps of: a) preparing a long-lasting oxyntomodulin conjugate; and b) mixing the prepared long-lasting oxyntomodulin conjugate with a stabilizer, which contains a buffer, a sugar alcohol and a non-ionic surfactant, and a preservative.

Preferably, the stabilizer in step b) may further comprise one or more selected from the group consisting of isotonic agents, sugars, polyhydric alcohols and amino acids.

In still another aspect, the present invention provides a pharmaceutical composition for preventing or treating obesity or diabetes, comprising the above liquid formulation.

As used herein, the term "preventing" refers to all actions that inhibit or delay the development of a target disease. As used herein, the term "preventing" means administering the conjugate of the present invention to inhibit or delay the development of diabetic conditions, such as abnormal blood glucose levels or abnormal insulation secretion, or obesity conditions such as an increase in body weight or body fat.

As used herein, the term "treating" refers to all actions that alleviate, ameliorate or relieve the symptoms of the disease developed. As used herein, the term "treating" means administering the conjugate of the present invention to alleviate, ameliorate or relieve the above diabetic conditions or obesity conditions to normalize blood glucose levels and insulin secretion and reduce body weight or body fat.

As used herein, the term "obesity" refers to an excessive amount of body fat. A body mass index (=weight (kg) divided by height (m)) of 25 or more is defined as obesity. Obesity generally results from an energy imbalance in which energy intake exceeds energy expenditure. Obesity is a metabolic disease that affects the entire body and highly likely to lead to diabetes and hyperlipidemia. In addition, obesity is related to sexual dysfunction, arthritis, and an increased risk of the development of cardiovascular diseases, and is also related to the development of cancer in some cases.

As used herein the term "diabetes" is a kind of metabolic disease in which insulin secretion is insufficient or normal functions are not made. Diabetes is characterized by increased blood glucose levels and causes various health problems. In the case of diabetes, glucose is excreted with urine.

The pharmaceutical composition of the present invention may further comprise a pharmaceutically acceptable carrier, excipient or diluent. As used herein, the term "pharmaceutically acceptable" means an amount that is sufficient to exhibit therapeutic effects and causes no side effects. The dose of the active ingredient of the pharmaceutical composition of the present invention may be readily determined by those skilled in the art depending on the type of disease, the patient's age, weight, health condition, sex, and drug sensitivity, the route of administration, the mode of administration, the frequency of administration, the duration of treatment, drugs used in combination or coincident with the composition of this invention, and other factors known in the medical field.

In still another aspect, the present invention provides a method for preventing or treating obesity or diabetes, comprising administering the liquid formulation to a subject.

Herein, the liquid formulation, obesity and diabetes are as described above.

As used herein, the term "subject" refers to a subject suspected of having obesity or diabetes. Specifically, the term means mammals, including humans, rats and domestic animals, which have or are at the risk of developing the above disease. In addition, the subject may be any subject that can be treated by the liquid formulation derivative of the present invention.

The therapeutic method of the present invention may comprise administering a pharmaceutically effective amount of the pharmaceutical composition comprising the liquid formulation. The total daily dose of the composition can be determined through appropriate medical judgment by a physician, and the composition may be administered once or several times. However, in view of the purpose of the present invention, the specific therapeutically effective dose of the composition for any particular patient may vary depending on various factors well known in the medical field, including the kind and degree of response to be achieved, concrete compositions according to whether other agents are used therewith or not, the patient's age, body weight, health condition, sex and diet, the time and route of administration, the secretion rate of the composition, the duration of treatment, other drugs used in combination or coincident with the composition of the present invention, and other factors known in the medical field.

Advantageous Effects

The inventive liquid formulation comprising the long-lasting oxyntomodulin conjugate comprises a buffer, a sugar alcohol and a nonionic surfactant and does not contain a human serum albumin and factors that are potentially harmful to the human body, and thus is not susceptible to viral infection. In addition, the oxyntomodulin conjugate of the present invention comprises oxyntomodulin linked to an immunoglobulin Fc region, and thus has a great molecular weight, prolonged physiological activity, and excellent storage stability, compared to native oxyntomodulin.

DESCRIPTION OF DRAWINGS

FIG. 5b is a graphic diagram showing the results obtained by evaluating the stability of a long-lasting oxyntomodulin conjugate according to the concentration of a surfactant and the presence or absence of an amino acid by SE-HPLC in Example 6 after 0-4 weeks of storage at 25° C. Each graph in FIG. 5b shows the percent retention of the long-lasting oxyntomodulin conjugate relative to the start value.

FIG. 5c is a graphic diagram showing the results obtained by evaluating the stability of a long-lasting oxyntomodulin conjugate according to the concentration of a surfactant and the presence or absence of an amino acid by RP-HPLC in Example 6 after 0-4 weeks of storage at 25° C. Each graph in FIG. 5c shows the percent retention of the long-lasting oxyntomodulin conjugate relative to the start value.

FIG. 7b is a graphic diagram showing the results obtained by evaluating the stability of a long-lasting oxyntomodulin conjugate according to pH and the kind of buffer alcohol by SE-HPLC in Example 8 after 0-4 weeks of storage at 25° C. Each graph in FIG. 7b shows the percent retention of the long-lasting oxyntomodulin conjugate relative to the start value.

FIG. 8c is a graphic diagram showing the results obtained by evaluating the stability of a long-lasting oxyntomodulin conjugate according to the presence or absence of a preservative and the concentration of long-lasting oxyntomodulin by RP-HPLC in Example 9 after 0-4 weeks of storage at 25° C. Each graph in FIG. 8c shows the percent retention of the long-lasting oxyntomodulin conjugate relative to the start value.

MODE FOR INVENTION

Figure 1A:
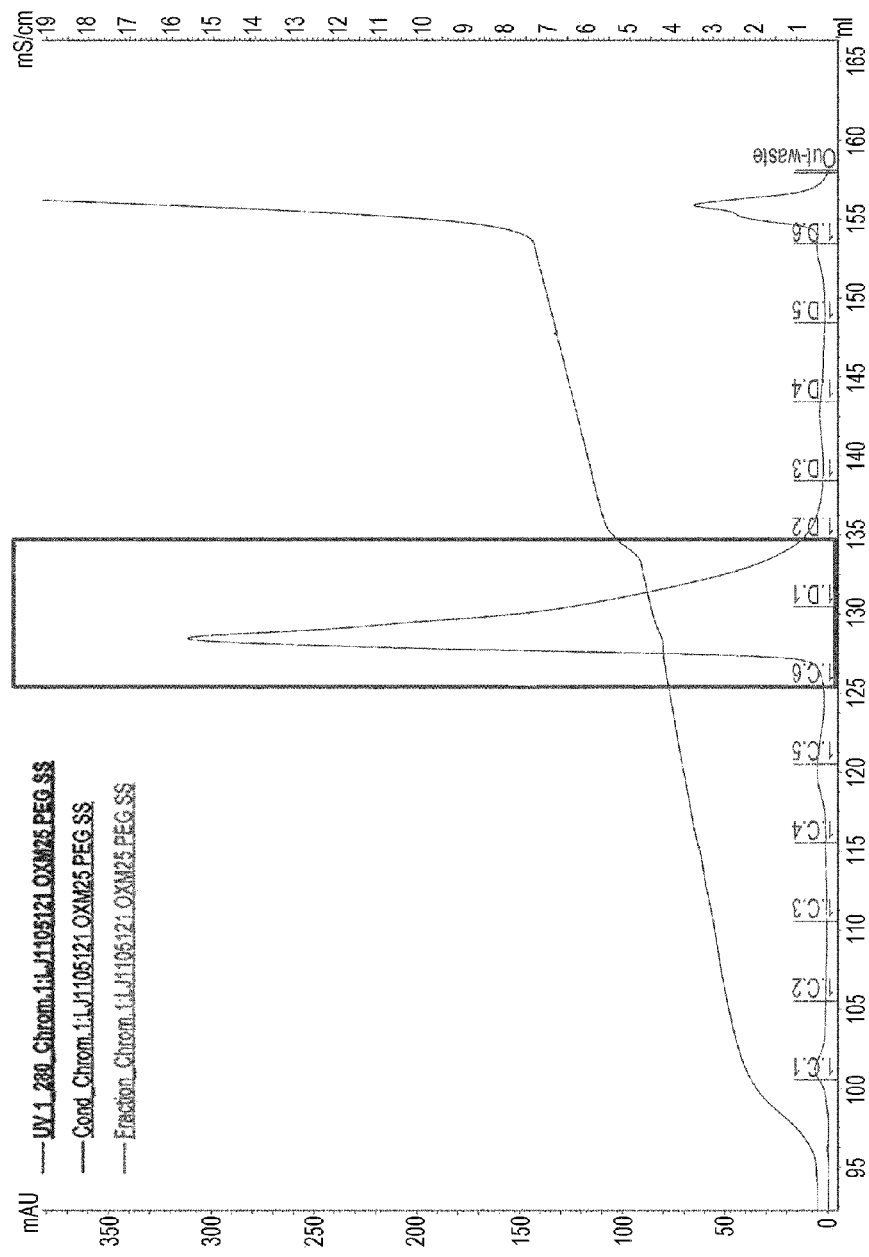
FIG. 1a is a graph showing the results obtained by purifying a mono-PEGylated oxyntomodulin derivative (SEQ ID NO: 25) through a SOURCE S purification column.

Hereinafter, the present invention will be described in further detail with reference to examples. It is to be understood, however, that these examples are for illustrative purposes only and are not intended to limit the scope of the present invention.

EXAMPLE 1

Synthesis of Oxyntomodulin and Oxyntomodulin Derivatives

In order to measure the stabilities of oxyntomodulin and oxyntomodulin derivatives in the liquid formulation of the present invention, oxyntomodulin derivatives having the amino acid sequences shown in Table 1 below were synthesized.

TABLE 1

| Oxyntomodulin and oxyntomodulin derivatives | |
|---|---|
| SEQ ID NO | Sequence |
| SEQ ID NO: 1 | HSQGTFTSDYSKYLDSRRAQDFVQWLMNTKRNRNNIA |
| SEQ ID NO: 2 | CA-SQGTFTSDYSKYLDEEAVRLFIEWLMNTKRNRNNIA |
| SEQ ID NO: 3 | CA-SQGTFTSDYSKYLDERRAQDFVAWLKNTGPSSGAPPPS |
| SEQ ID NO: 4 | CA-GQGTFTSDYSRYLEEEAVRLFIEWLKNGGPSSGAPPPS |
| SEQ ID NO: 5 | CA-GQGTFTSDYSRQMEEEAVRLFIEWLKNGGPSSGAPPPS |
| SEQ ID NO: 6 | CA-GEGTFTSDLSRQMEEEAVRLFIEWAAHSQGTFTSDYSKYLD |
| SEQ ID NO: 7 | CA-SQGTFTSDYSRYLDEEAVRLFIEWLMNTK |
| SEQ ID NO: 8 | CA-SQGTFTSDLSRQLEEEAVRLFIEWLMNK |
| SEQ ID NO: 9 | CA-GQGTFTSDYSRYLDEEAVXLFIEWLMNTKRNRNNIA |
| SEQ ID NO: 10 | CA-SQGTFTSDYSRQMEEEAVRLFIEWLMNGGPSSGAPPPSK |
| SEQ ID NO: 11 | CA-GEGTFTSDLSRQMEEEAVRLFIEWAAHSQGTFTSDYSRYLDK |
| SEQ ID NO: 12 | CA-SQGTFTSDYSRYLDGGGHGEGTFTSDLSKQMEEEAVK |
| SEQ ID NO: 13 | CA-SQGTFTSDYSRYLDXEAVXLFIEWLMNTK |
| SEQ ID NO: 14 | CA-GQGTFTSDYSRYLDEEAVXLFIXWLMNTKRNRNNIA |
| SEQ ID NO: 15 | CA-GQGTFTSDYSRYLDEEAVXLFIXWLMNTKRNRNNIA |
| SEQ ID NO: 16 | CA-SQGTFTSDLSRQLEGGGHSQGTFTSDLSRQLEK |
| SEQ ID NO: 17 | CA-SQGTFTSDYSRYLDEEAVRLFIEWIRNTKRNRNNIA |
| SEQ ID NO: 18 | CA-SQGTFTSDYSRYLDEEAVRLFIEWIRNGGPSSGAPPPSK |
| SEQ ID NO: 19 | CA-SQGTFTSDYSRYLDEEAVKLFIEWIRNTKRNRNNIA |
| SEQ ID NO: 20 | CA-SQGTFTSDYSRYLDEEAVKLFIEWIRNGGPSSGAPPPSK |
| SEQ ID NO: 21 | CA-SQGTFTSDYSRQLEEEAVRLFIEWVRNTKRNRNNIA |
| SEQ ID NO: 22 | DA-SQGTFTSDYSKYLDEKRAKEFVQWLMNTK |
| SEQ ID NO: 23 | HAibQGTFTSDYSKYLDEKRAKEFVCWLMNT |
| SEQ ID NO: 24 | HAibQGTFTSDY SKYLDEKRAK EFVQWLMNTC |
| SEQ ID NO: 25 | HAibQGTFTSDYSKYLDEKRAKEFVQWLMNIC |
| SEQ ID NO: 26 | HAibQGTFTSDYSKYLDEKRAKEFVQWLMNTC |
| SEQ ID NO: 27 | HAibQGTFTSDYSKYLDEQAAKEFICWLMNT |
| SEQ ID NO: 28 | HAibQGTFTSDY SKYLDEK RAKEFVQWLMNT |
| SEQ ID NO: 29 | H(d)SQGTFTSDYSKYLDSRRAQDFVQWLMNTKRNRNNIA |
| SEQ ID NO: 30 | CA-SQGTFTSDYSKYLDSRRAQDFVQWLMNTKRNRNNIA |
| SEQ ID NO: 31 | CA-(d)SQGTFTSDYSKYLDSRRAQDFVQWLMNTKRNRNNIA |
| SEQ ID NO: 32 | CA-AibQGTFTSDYSKYLDEKRAKEFVQWLMNTC |
| SEQ ID NO: 33 | HAibQGTFTSDYAKYLDEKRAKEFVQWLMNTC |
| SEQ ID NO: 34 | YAibQGTFTSDYSKYLDEKRAKEFVQWLMNTC |

In Table a above, the amino acid residues indicated by bold letters mean amino acids that form rings, and the amino acid residues indicated by X mean alpha-methyl-glutamic acid that is a non-native amino acid. In addition, CA indicates 4-imidazoacetyl, DA indicates desamino-histidyl, and (d)S indicates d-serine.

EXAMPLE 2

Preparation of Conjugate Comprising Oxyntomodulin Derivative (SEQ ID NO: 25) and Immunoglobulin Fc (Oxyntomodulin Derivative (SEQ ID NO: 25) Linked to Immunoglobulin Fc Region)

First, in order to PEGylate MAL-10K-ALD PEG at a cysteine residue at amino acid position 30 of an oxyntomodulin derivative (SEQ ID NO: 25), the oxyntomodulin derivative (SEQ ID NO: 25) and MAL-10K-ALD PEG were allowed to react with each other at a molar ratio of 1:3 and a protein concentration of 3 mg/ml at room temperature for 3 hours. Herein, the reaction was performed in 50 mM Tris buffer (pH 8.0) in the presence of 1M guanidine. After completion of the reaction, the reaction solution was applied to a SOURCE S column to purify an oxyntomodulin derivative mono-PEGylated at the cysteine (column: SOURCE S, flow rate: 2.0 ml/min, gradient: A 0→100% 50 min B (A: 20 mM Na-citrate, pH 3.0+45% ethanol, B: A+1M KCl)) (FIG. 1a). FIG. 1a is a graph showing the results obtained by purifying the mono-PEGylated oxyntomodulin derivative (SEQ ID NO: 25) through the SOURCE S purification column.

Figure 1B:
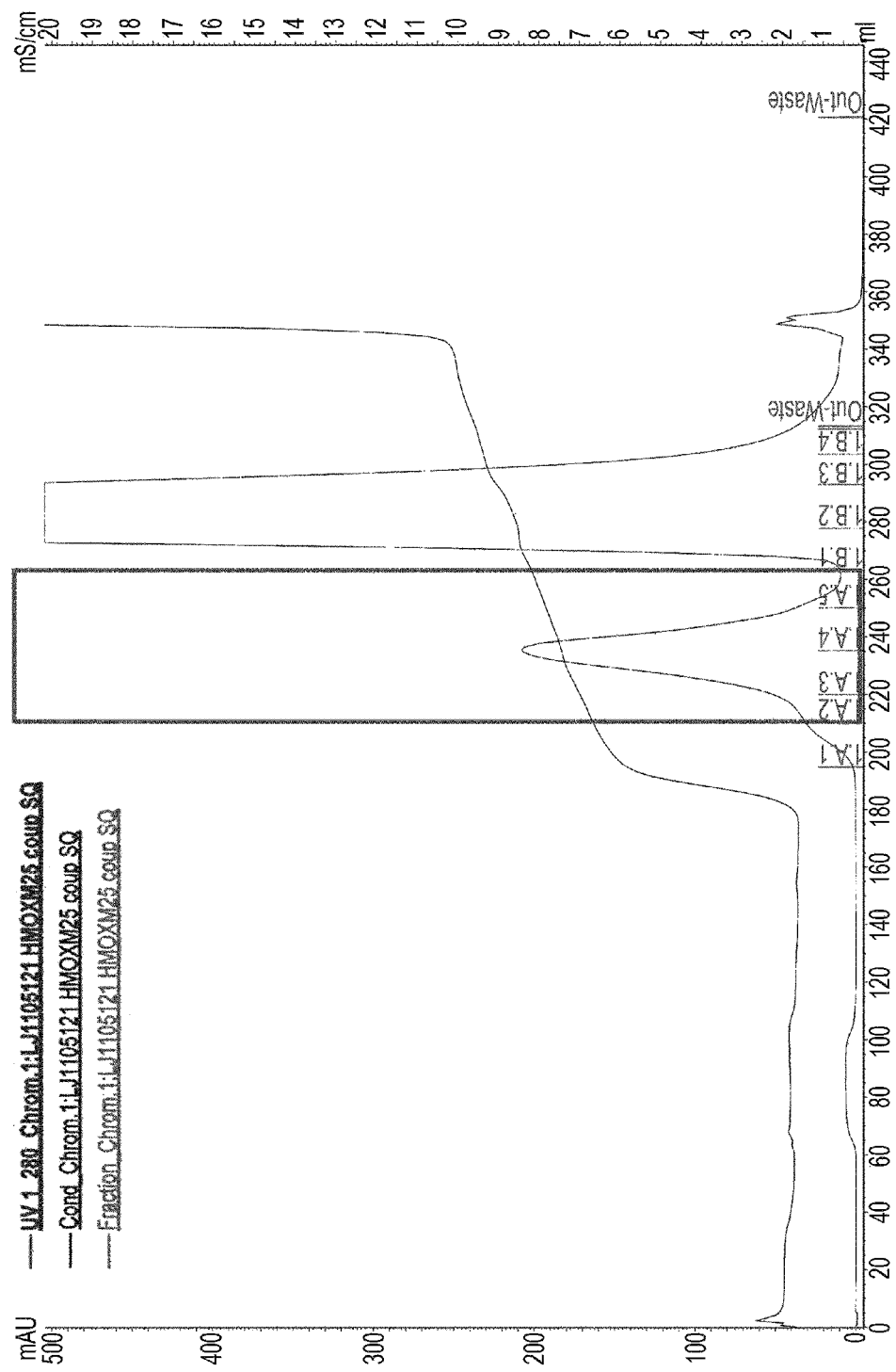
FIG. 1b is a graph showing the results obtained by purifying a conjugate of a mono-PEGylated oxyntomodulin derivative (SEQ ID NO: 25) and an immunoglobulin Fc through a SOURCE 15Q purification column.
Figure 1C:
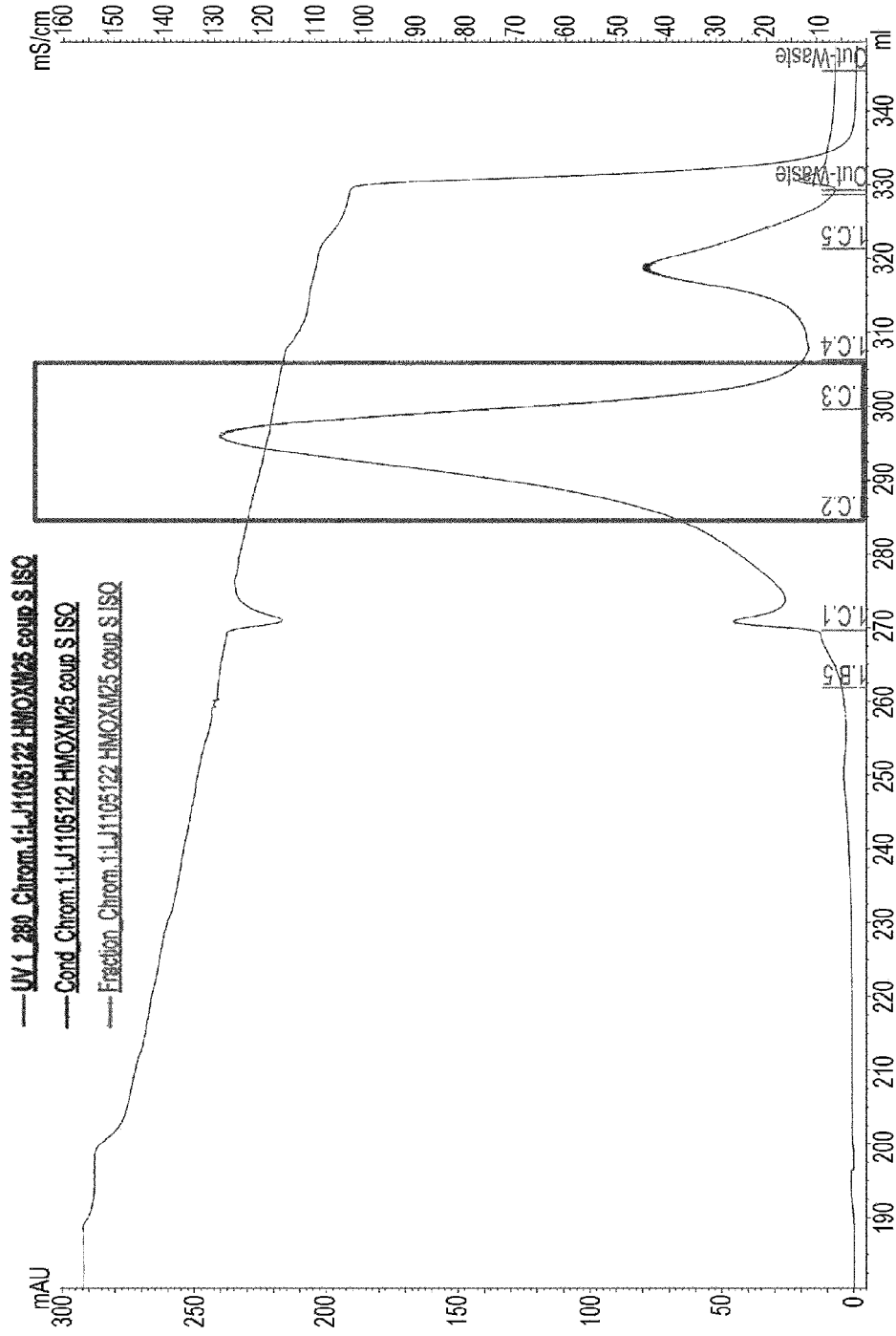
FIG. 1c is a graph showing the results obtained by purifying a conjugate of a mono-PEGylated oxyntomodulin derivative (SEQ ID NO: 25) and an immunoglobulin Fc through a SOURCE ISO purification column.
Figure 2A:
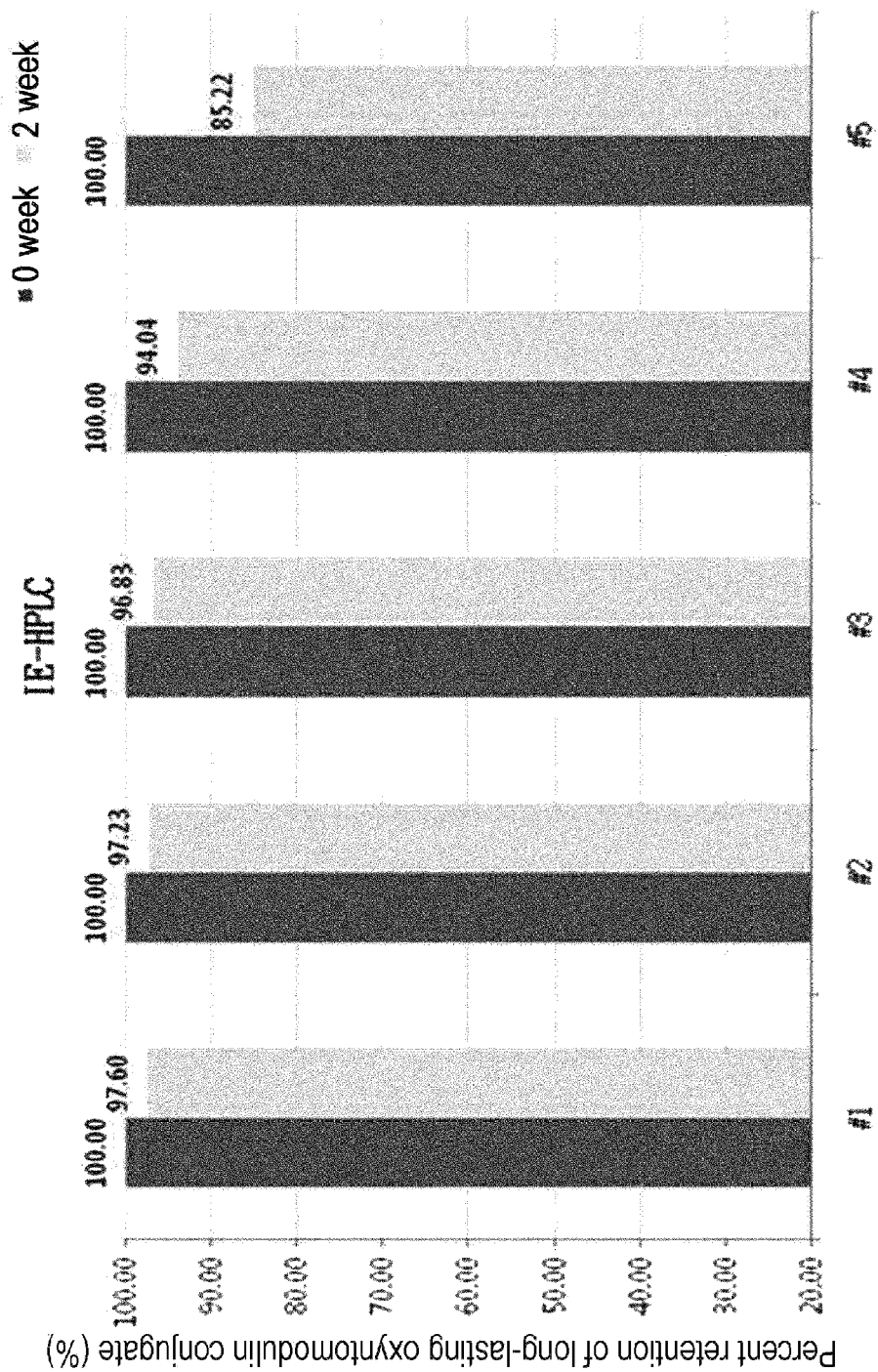
FIG. 2a is a graphic diagram showing the results obtained by evaluating the stability of a long-lasting oxyntomodulin conjugate according to pH by IE-HPLC in Example 3 after 0-2 weeks of storage at 25° C. Each graph in FIG. 2a shows the percent retention of the long-lasting oxyntomodulin conjugate relative to the start value.
Figure 2B:
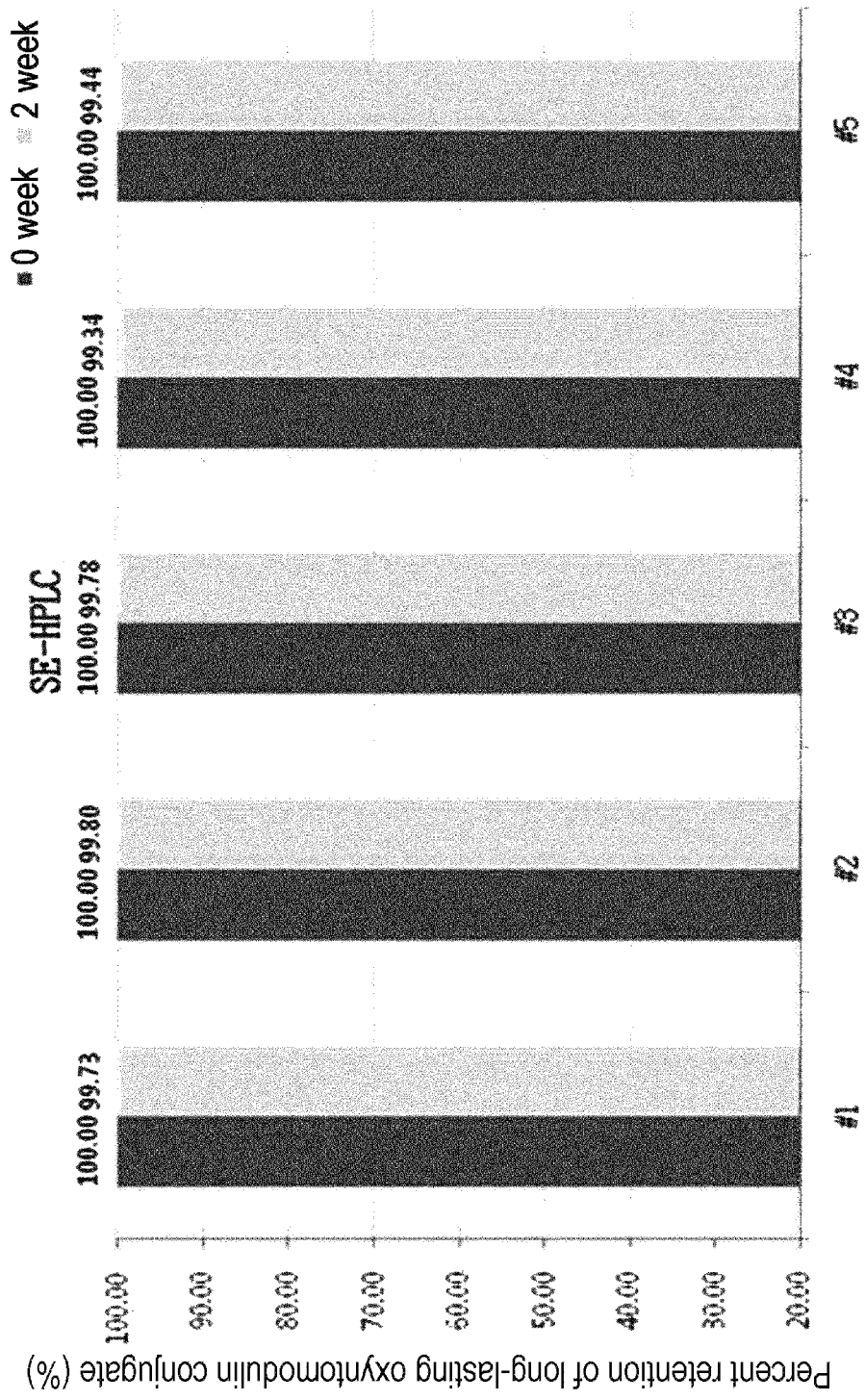
FIG. 2b is a graphic diagram showing the results obtained by evaluating the stability of a long-lasting oxyntomodulin conjugate according to pH by SE-HPLC in Example 3 after 0-2 weeks of storage at 25° C. Each graph in FIG. 2b shows the percent retention of the long-lasting oxyntomodulin conjugate relative to the start value.
Figure 2C:
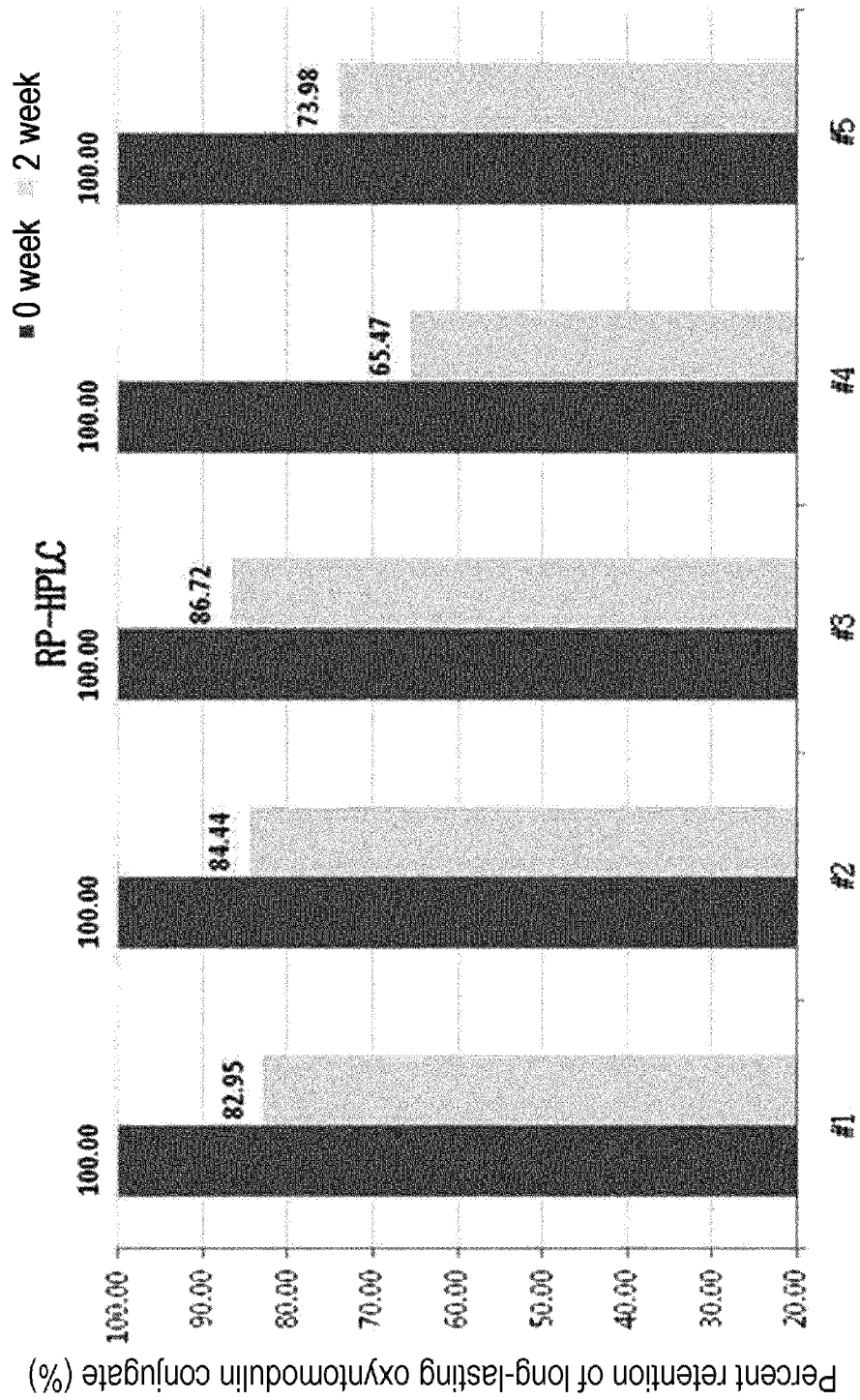
FIG. 2c is a graphic diagram showing the results obtained by evaluating the stability of a long-lasting oxyntomodulin conjugate according to pH by RP-HPLC in Example 3 after 0-2 weeks of storage at 25° C. Each graph in FIG. 2c shows the percent retention of the long-lasting oxyntomodulin conjugate relative to the start value.
Figure 3A:
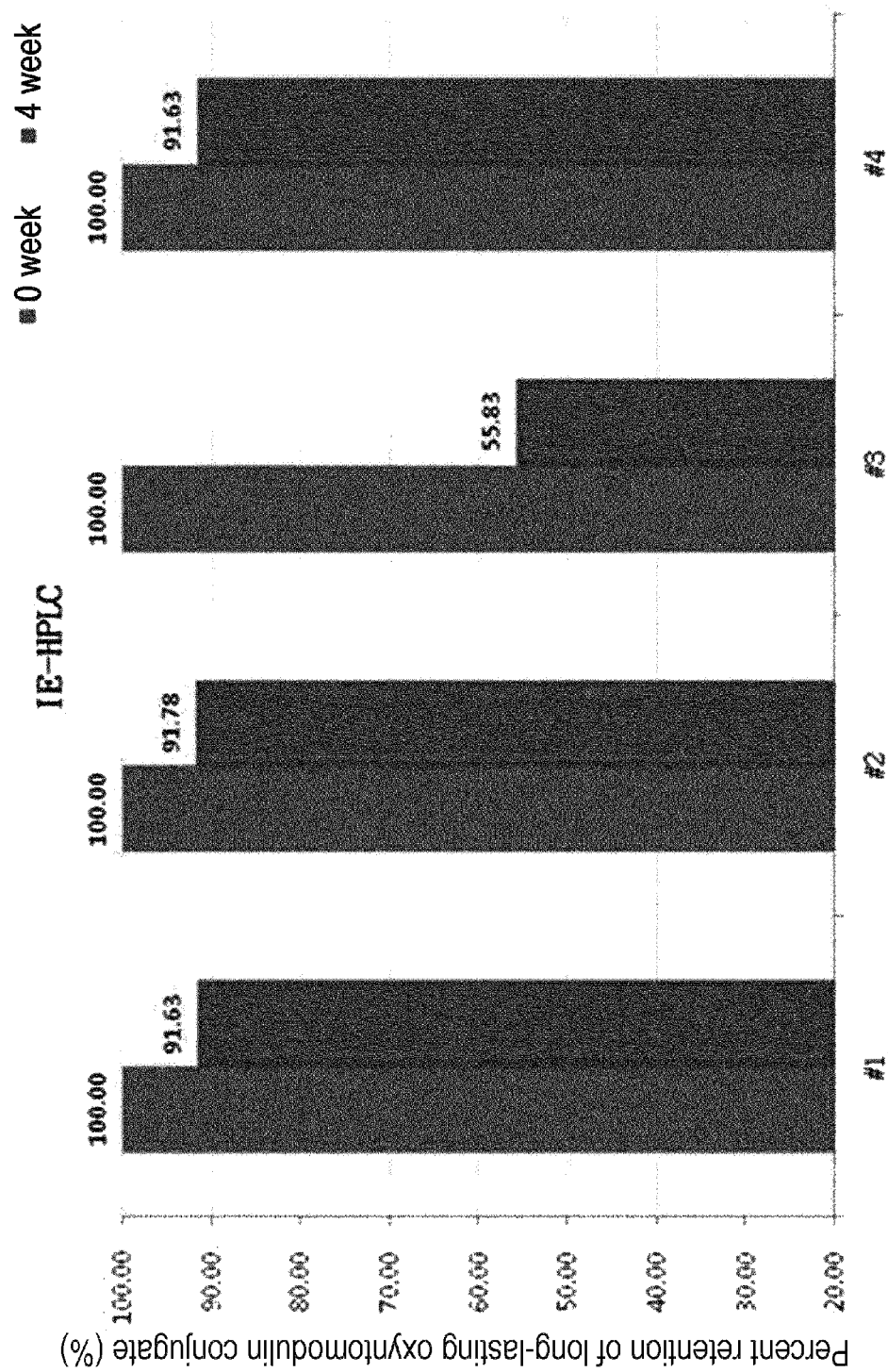
FIG. 3a is a graphic diagram showing the results obtained by evaluating the stability of a long-lasting oxyntomodulin conjugate according to the kind of sugar alcohol and the presence or absence of an isotonic agent by IE-HPLC in Example 4 after 0-4 weeks of storage at 25° C. Each graph in FIG. 3a shows the percent retention of the long-lasting oxyntomodulin conjugate relative to the start value.
Figure 3B:
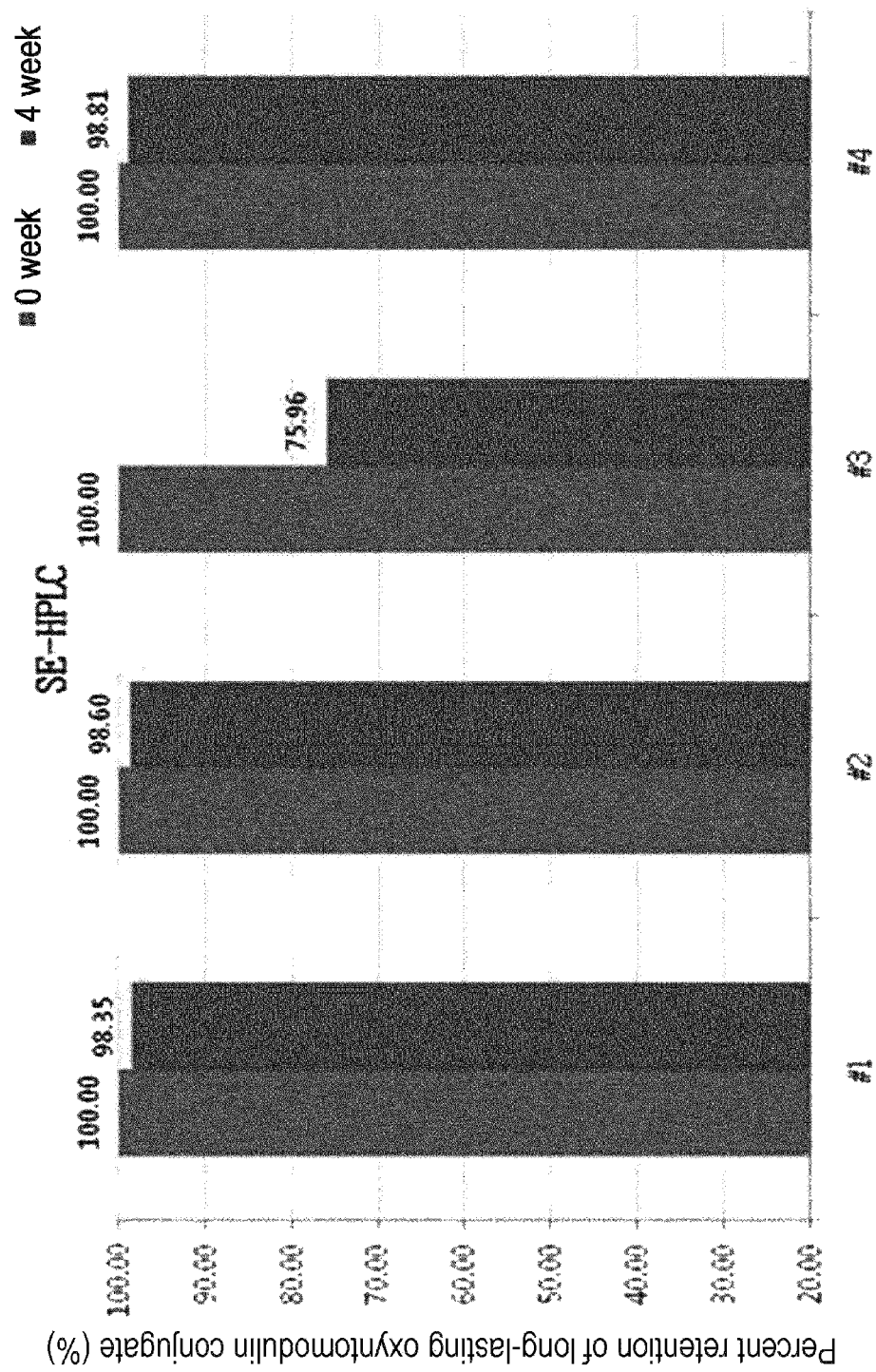
FIG. 3b is a graphic diagram showing the results obtained by evaluating the stability of a long-lasting oxyntomodulin conjugate according to the kind of sugar alcohol and the presence or absence of an isotonic agent by SE-HPLC in Example 4 after 0-4 weeks of storage at 25° C. Each graph in FIG. 3b shows the percent retention of the long-lasting oxyntomodulin conjugate relative to the start value.
Figure 3C:
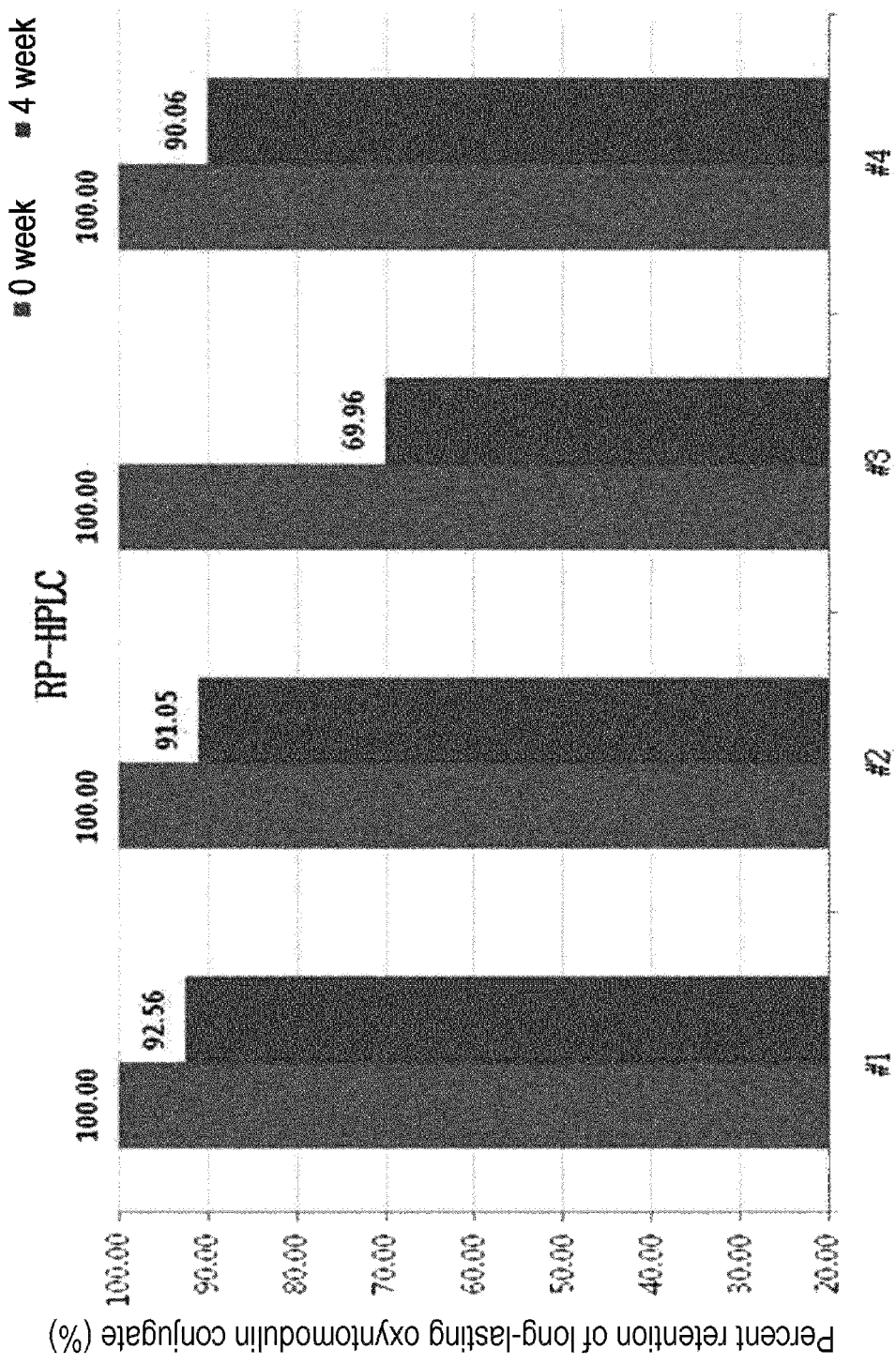
FIG. 3c is a graphic diagram showing the results obtained by evaluating the stability of a long-lasting oxyntomodulin conjugate according to the kind of sugar alcohol and the presence or absence of an isotonic agent by RP-HPLC in Example 4 after 0-4 weeks of storage at 25° C. Each graph in FIG. 3c shows the percent retention of the long-lasting oxyntomodulin conjugate relative to the start value.
Figure 4A:
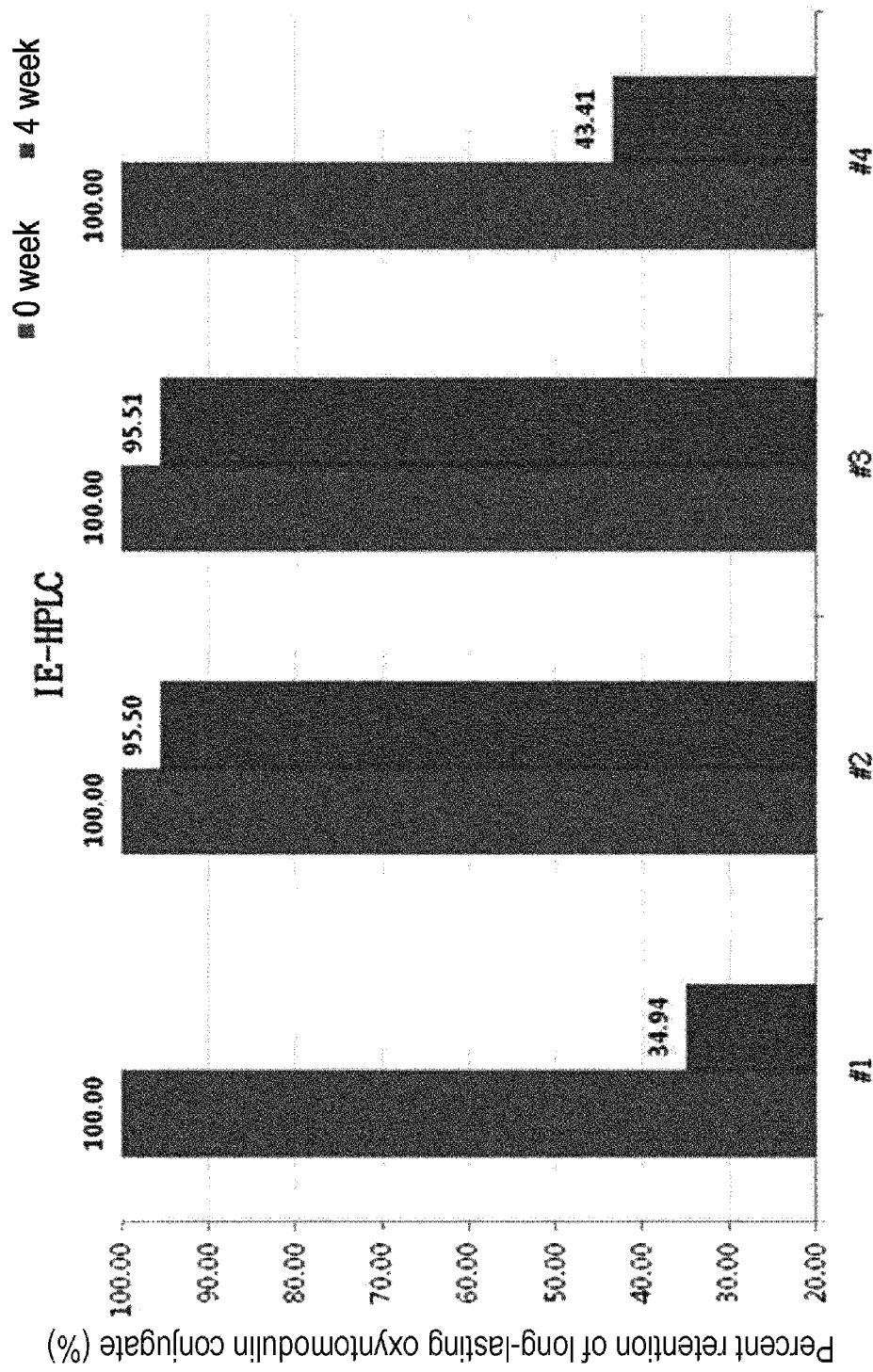
FIG. 4a is a graphic diagram showing the results obtained by evaluating the stability of a long-lasting oxyntomodulin conjugate according to the concentration of sugar alcohol by IE-HPLC in Example 5 after 0-4 weeks of storage at 25° C. Each graph in FIG. 4a shows the percent retention of the long-lasting oxyntomodulin conjugate relative to the start value.
Figure 4B:
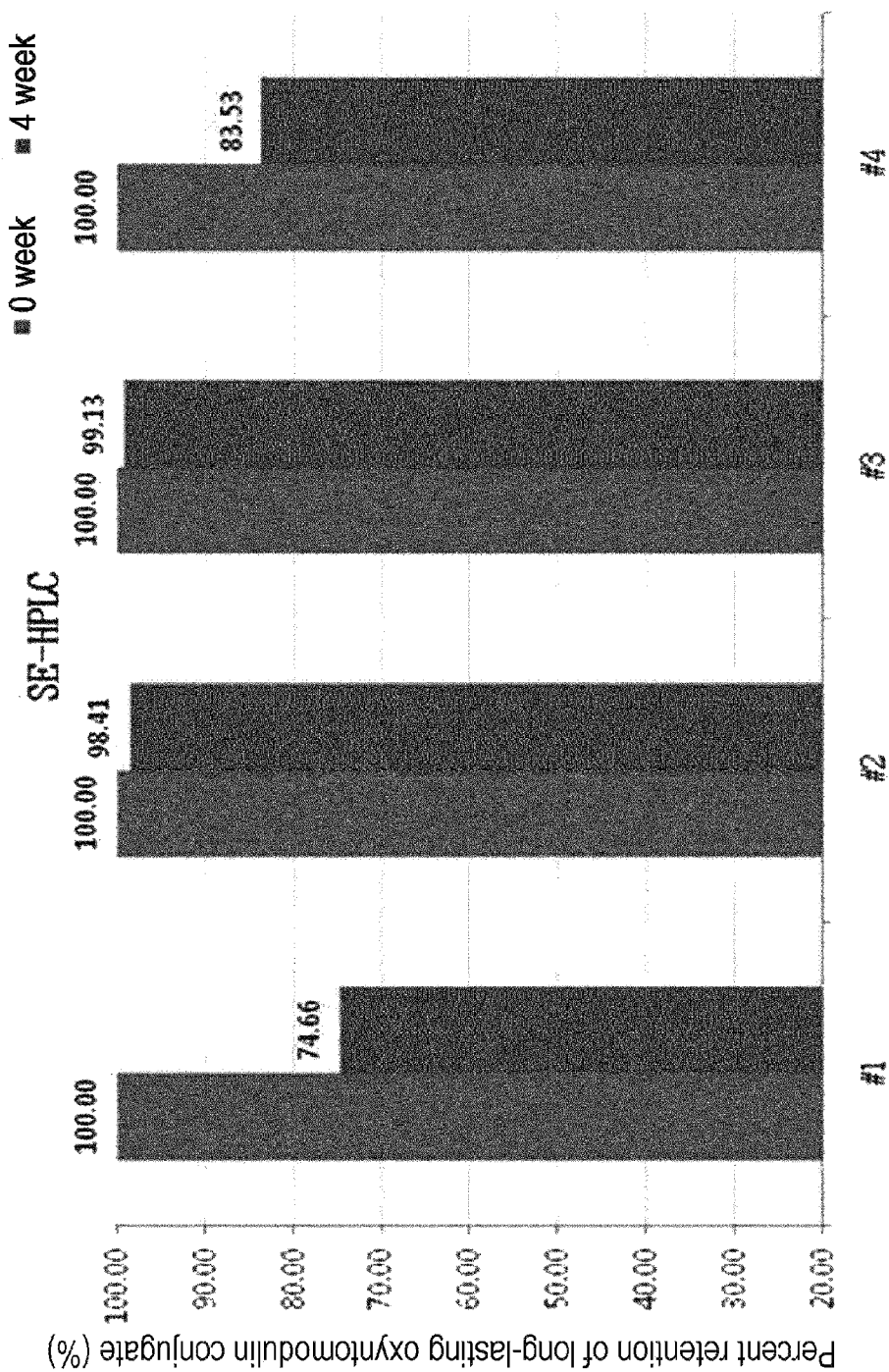
FIG. 4b is a graphic diagram showing the results obtained by evaluating the stability of a long-lasting oxyntomodulin conjugate according to the concentration of sugar alcohol by SE-HPLC in Example 5 after 0-4 weeks of storage at 25° C. Each graph in FIG. 4b shows the percent retention of the long-lasting oxyntomodulin conjugate relative to the start value.
Figure 4C:
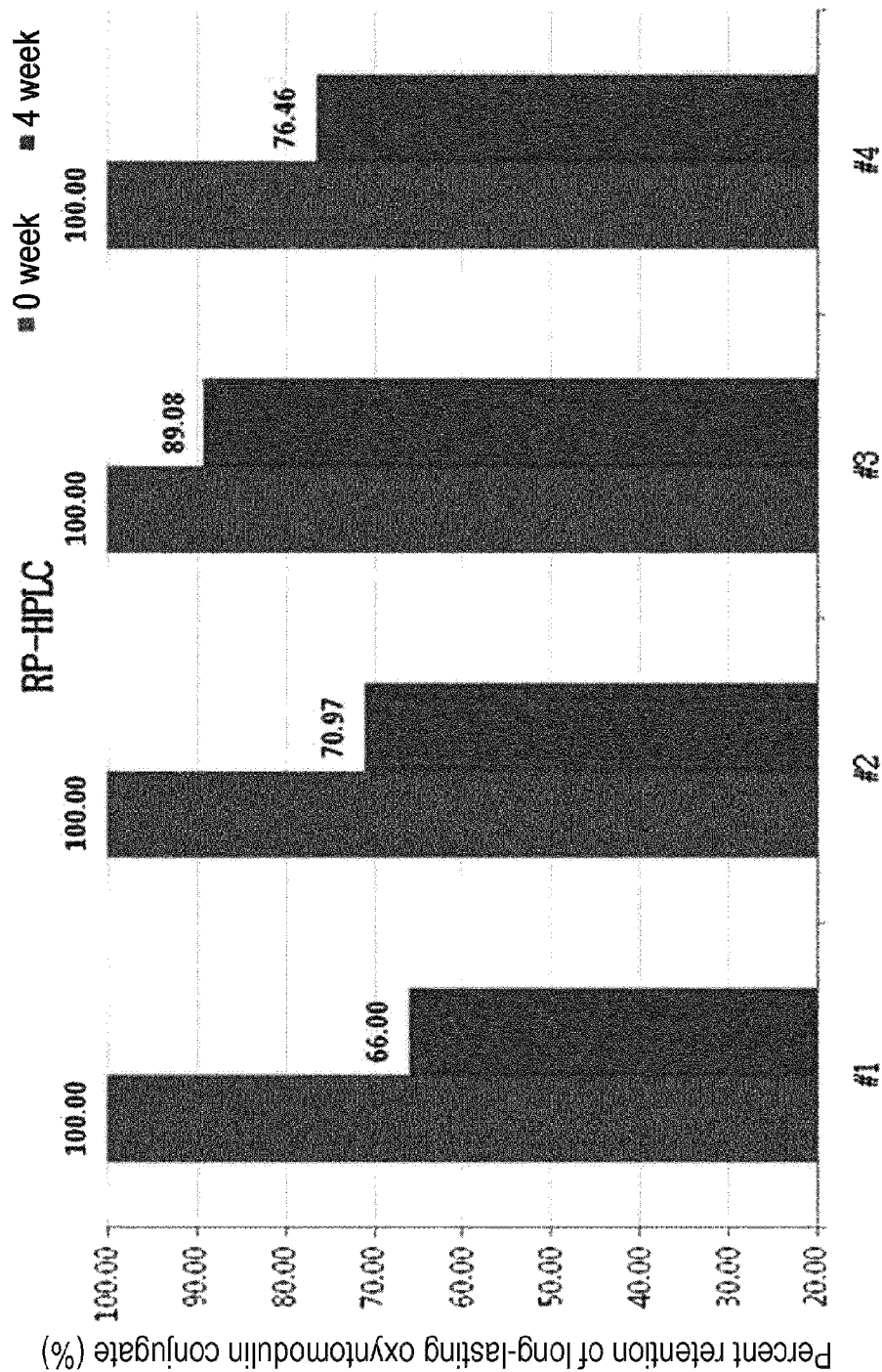
FIG. 4c is a graphic diagram showing the results obtained by evaluating the stability of a long-lasting oxyntomodulin conjugate according to concentration of sugar alcohol by RP-HPLC in Example 5 after 0-4 weeks of storage at 25° C. Each graph in FIG. 4c shows the percent retention of the long-lasting oxyntomodulin conjugate relative to the start value.
Figure 5A:
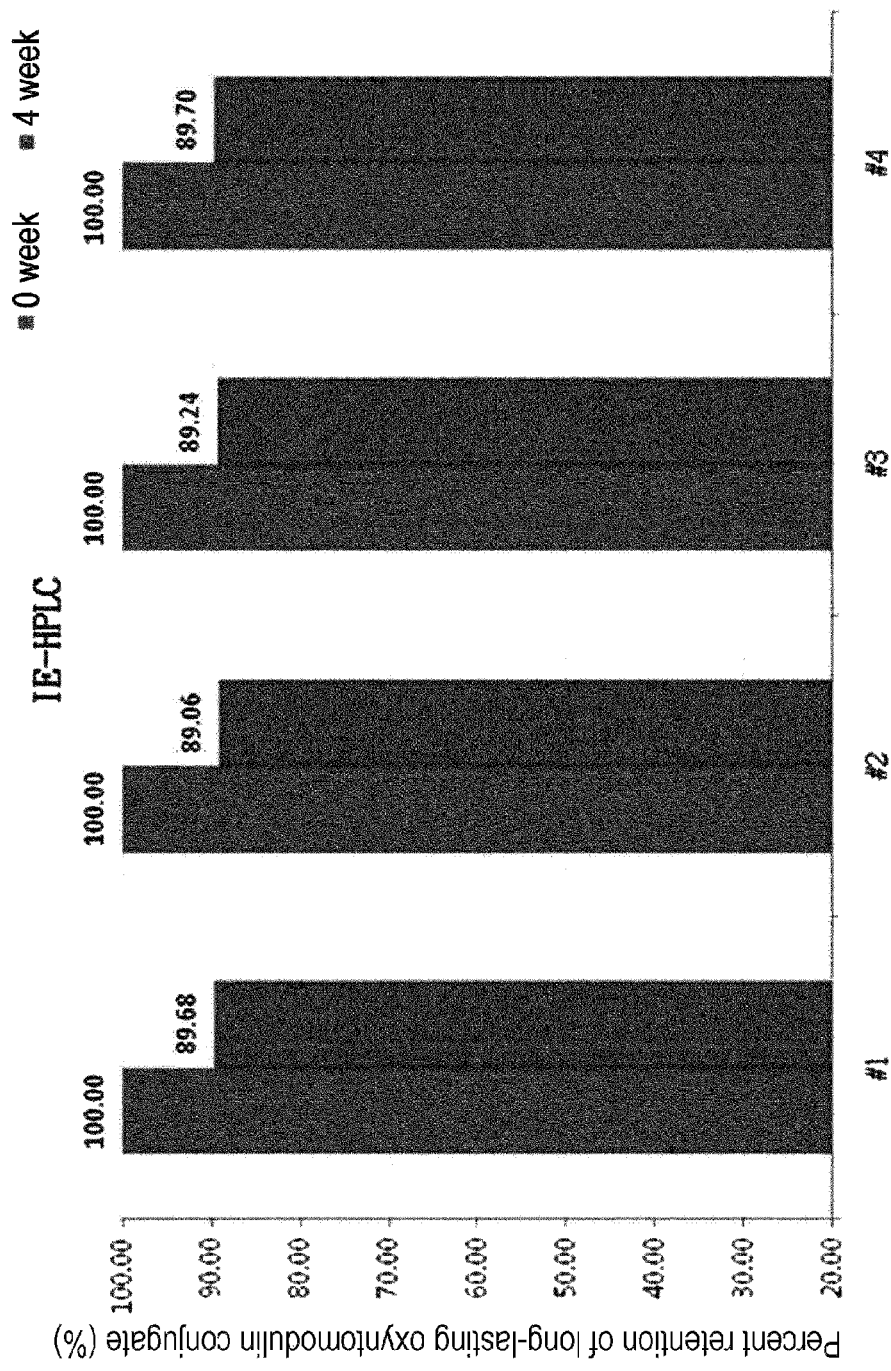
FIG. 5a is a graphic diagram showing the results obtained by evaluating the stability of a long-lasting oxyntomodulin conjugate according to the concentration of a surfactant and the presence or absence of an amino acid by IE-HPLC in Example 6 after 0-4 weeks of storage at 25° C. Each graph in FIG. 5a shows the percent retention of the long-lasting oxyntomodulin conjugate relative to the start value.
Figure 6A:
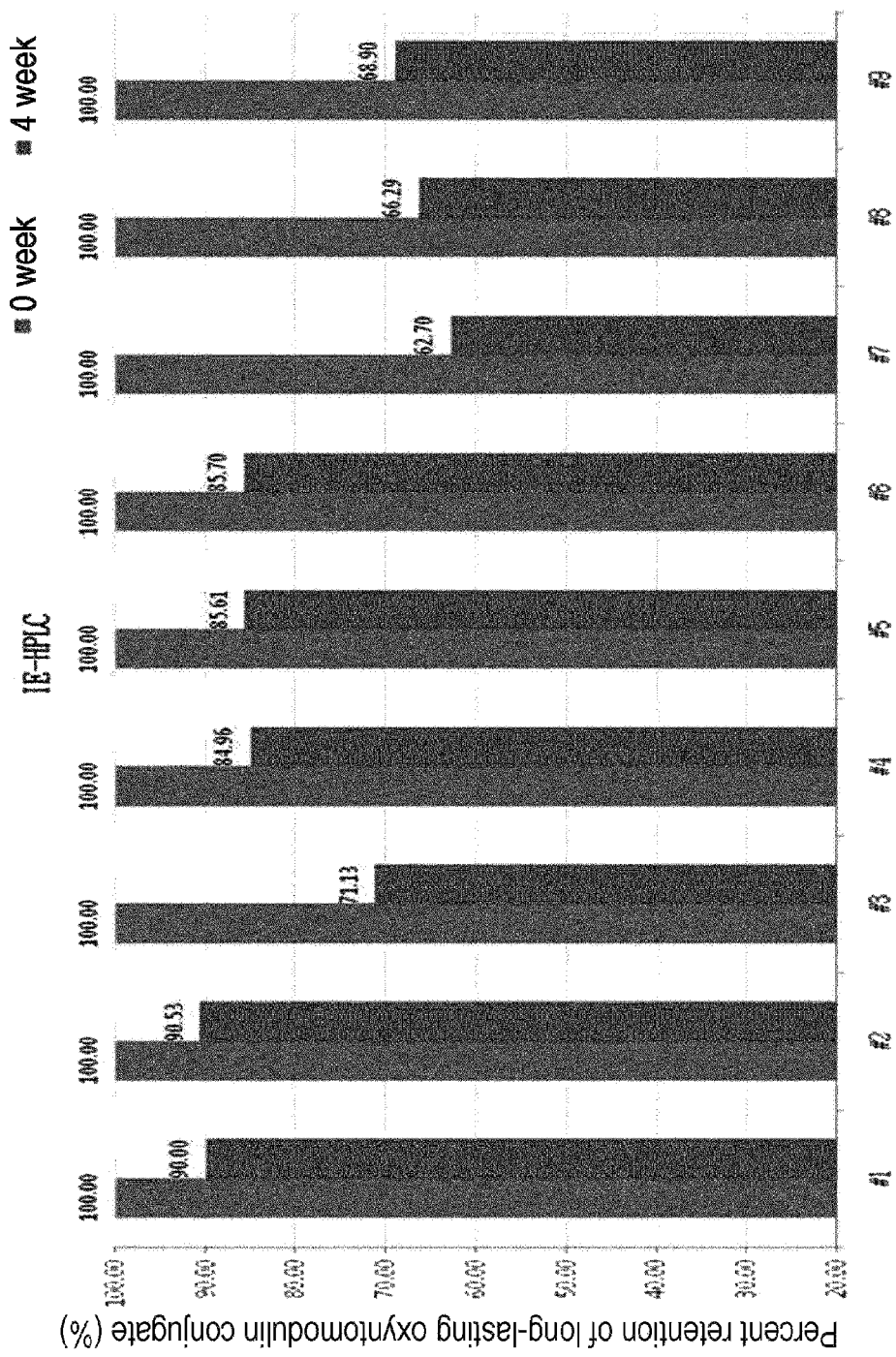
FIG. 6a is a graphic diagram showing the results obtained by evaluating the stability of a long-lasting oxyntomodulin conjugate according to pH and the concentration of sugar alcohol by IE-HPLC in Example 7 after 0-4 weeks of storage at 25° C. Each graph in FIG. 6a shows the percent retention of the long-lasting oxyntomodulin conjugate relative to the start value.
Figure 6B:
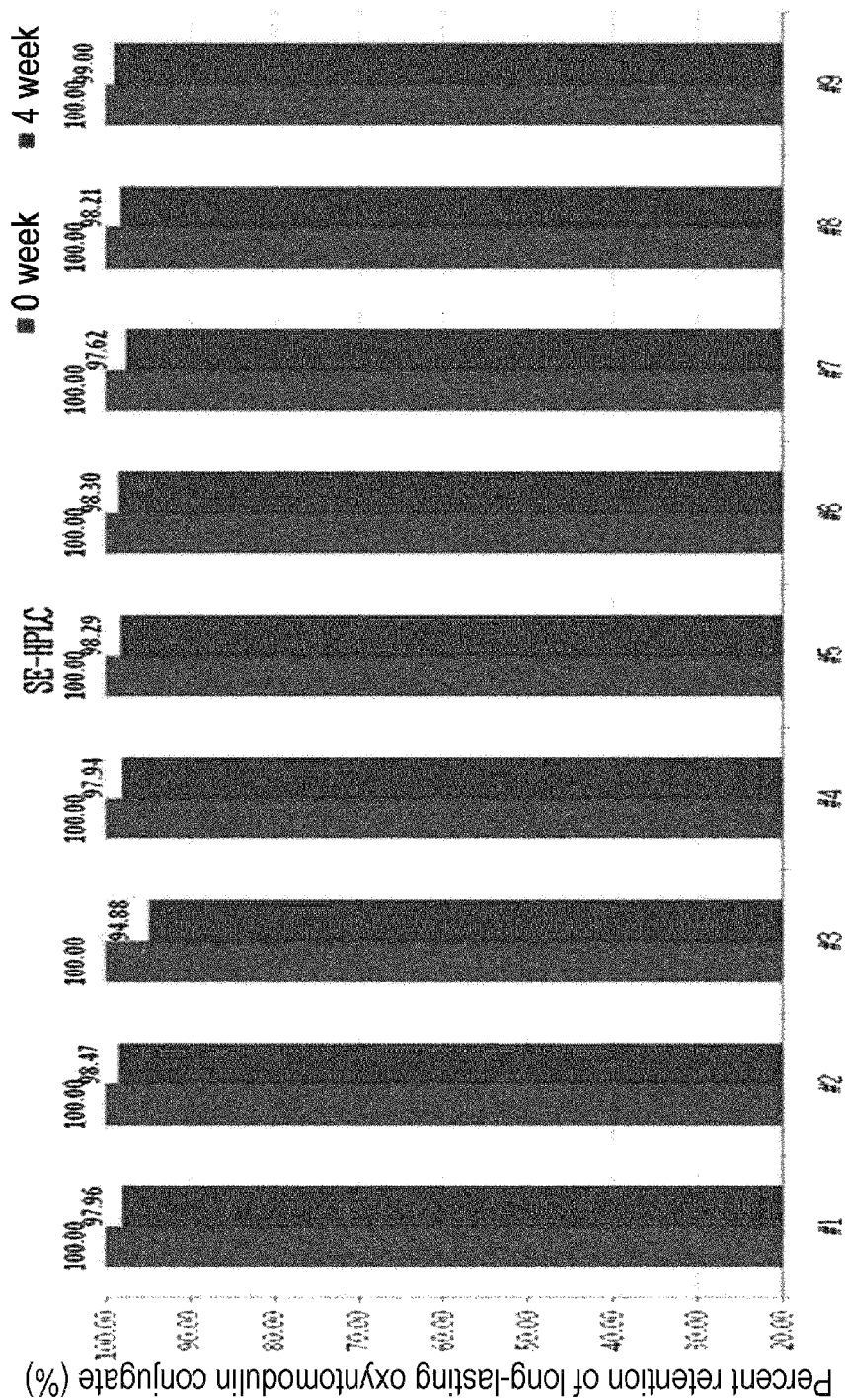
FIG. 6b is a graphic diagram showing the results obtained by evaluating the stability of a long-lasting oxyntomodulin conjugate according to pH and the concentration of sugar alcohol by SE-HPLC in Example 7 after 0-4 weeks of storage at 25° C. Each graph in FIG. 6b shows the percent retention of the long-lasting oxyntomodulin conjugate relative to the start value.
Figure 6C:
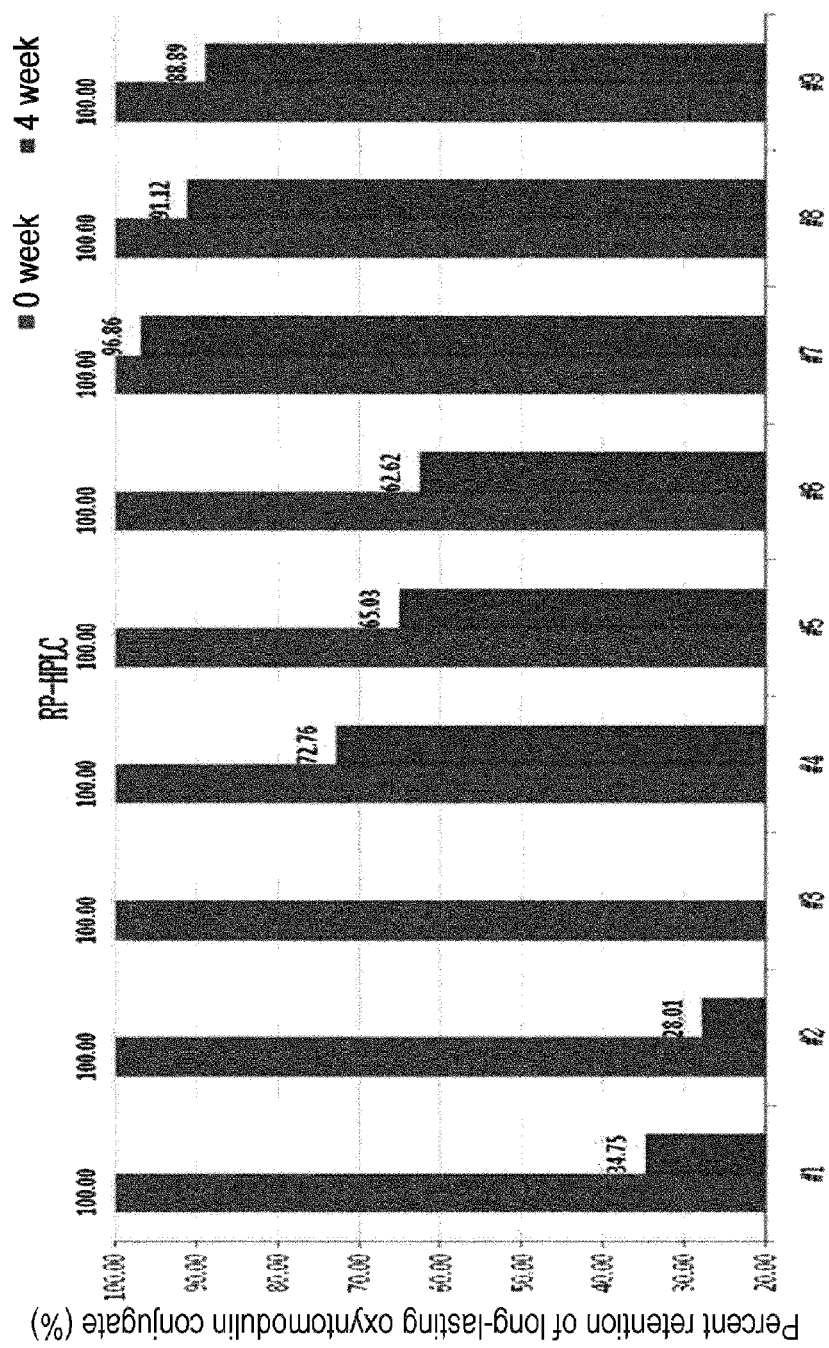
FIG. 6c is a graphic diagram showing the results obtained by evaluating the stability of a long-lasting oxyntomodulin conjugate according to pH and the concentration of sugar alcohol by RP-HPLC in Example 7 after 0-4 weeks of storage at 25° C. Each graph in FIG. 6c shows the percent retention of the long-lasting oxyntomodulin conjugate relative to the start value.
Figure 7A:
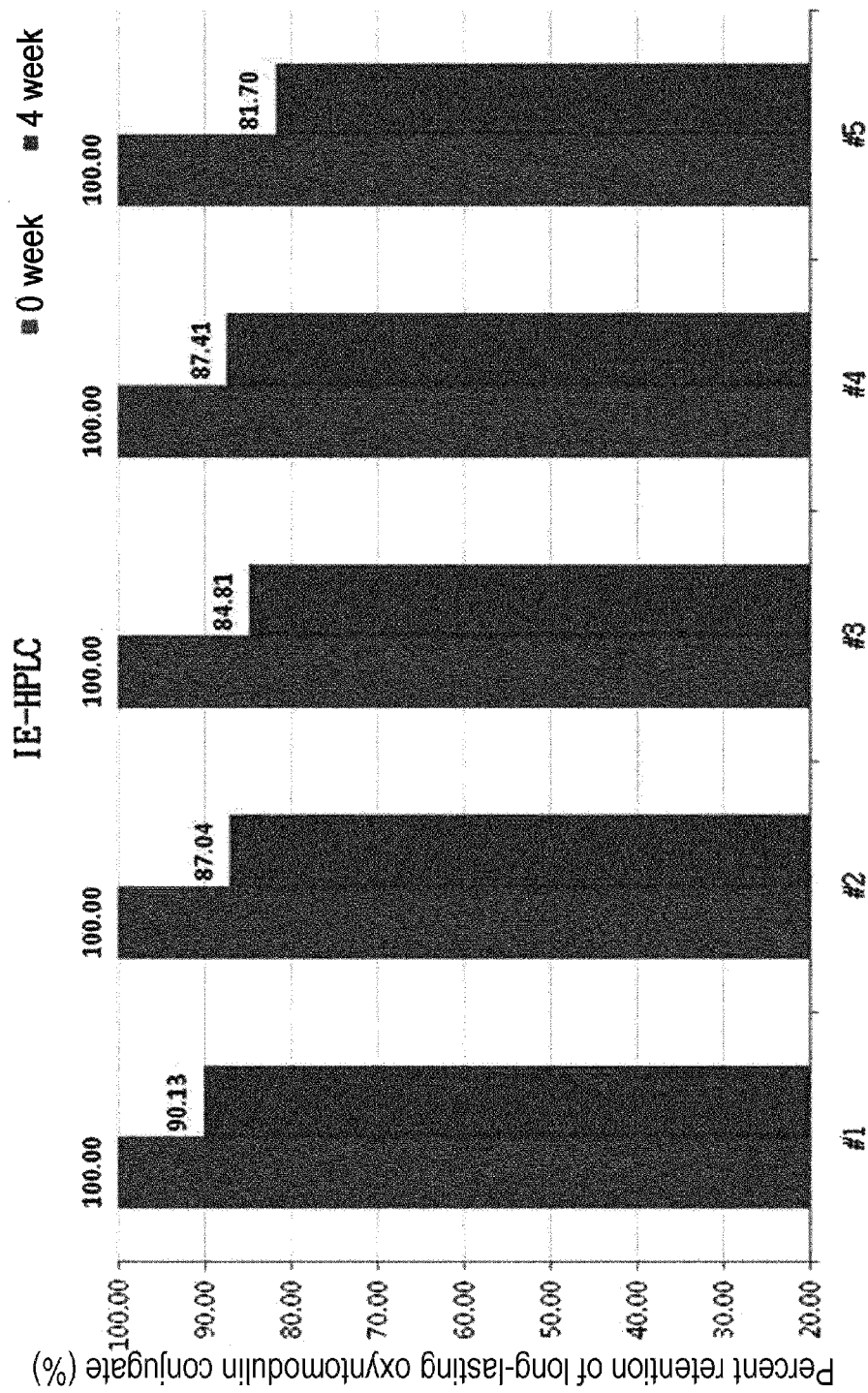
FIG. 7a is a graphic diagram showing the results obtained by evaluating the stability of a long-lasting oxyntomodulin conjugate according to pH and the kind of buffer alcohol by IE-HPLC in Example 8 after 0-4 weeks of storage at 25° C. Each graph in FIG. 7a shows the percent retention of the long-lasting oxyntomodulin conjugate relative to the start value.
Figure 7C:
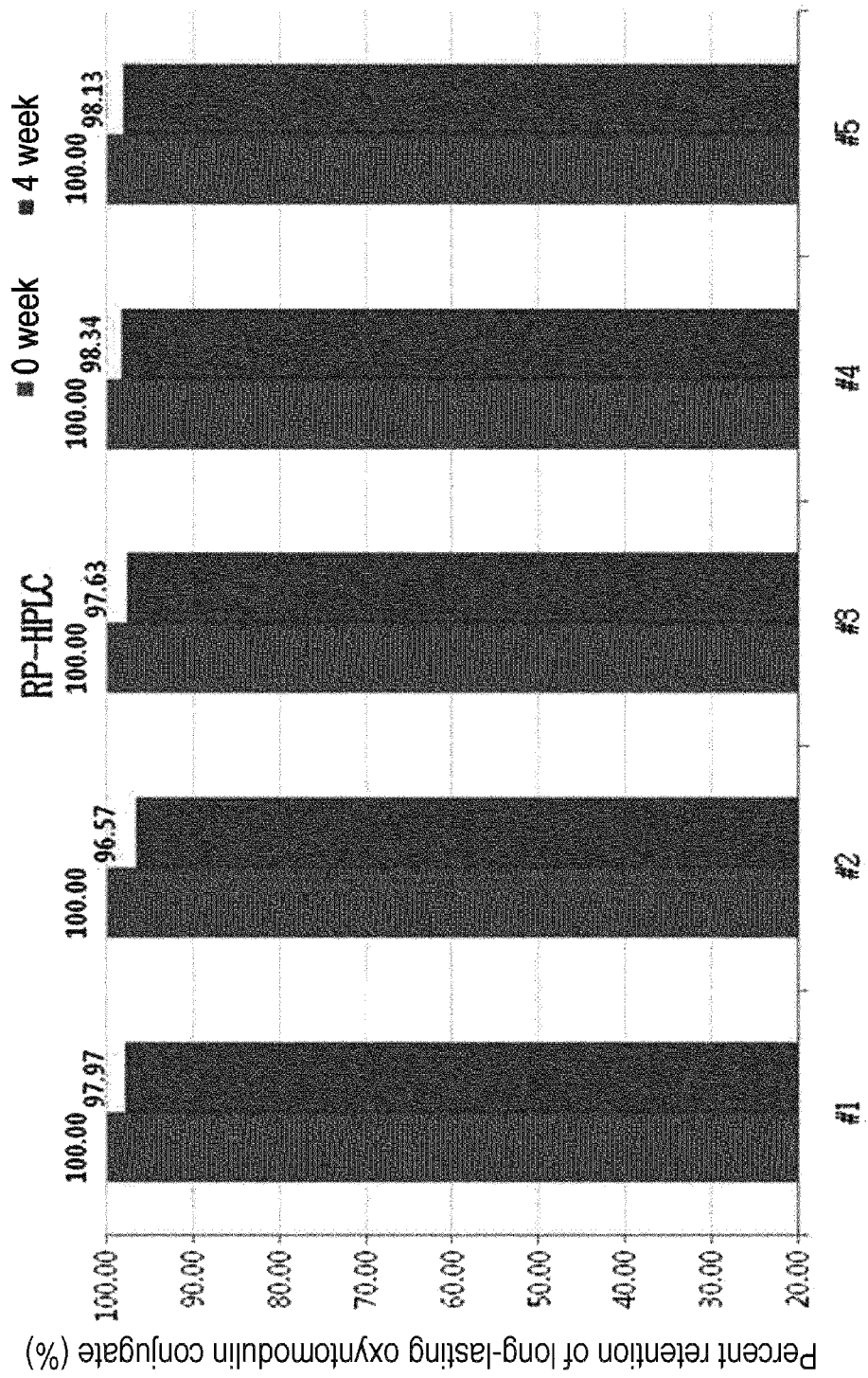
FIG. 7c is a graphic diagram showing the results obtained by evaluating the stability of a long-lasting oxyntomodulin conjugate according to pH and the kind of buffer alcohol by RP-HPLC in Example 8 after 0-4 weeks of storage at 25° C. Each graph in FIG. 7c shows the percent retention of the long-lasting oxyntomodulin conjugate relative to the start value.
Figure 8A:
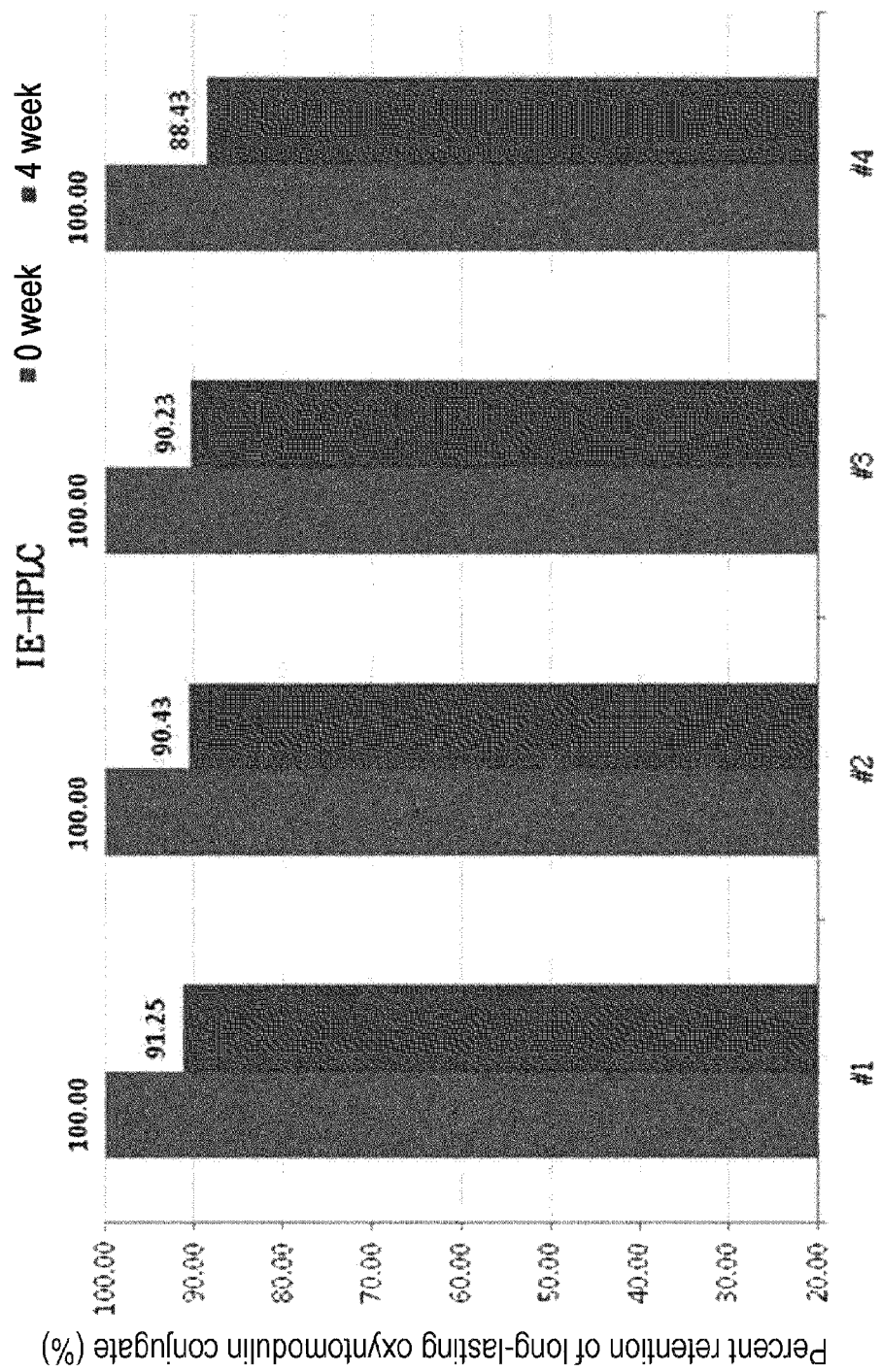
FIG. 8a is a graphic diagram showing the results obtained by evaluating the stability of a long-lasting oxyntomodulin conjugate according to the presence or absence of a preservative and the concentration of long-lasting oxyntomodulin by IE-HPLC in Example 9 after 0-4 weeks of storage at 25° C. Each graph in FIG. 8a shows the percent retention of the long-lasting oxyntomodulin conjugate relative to the start value.
Figure 8B:
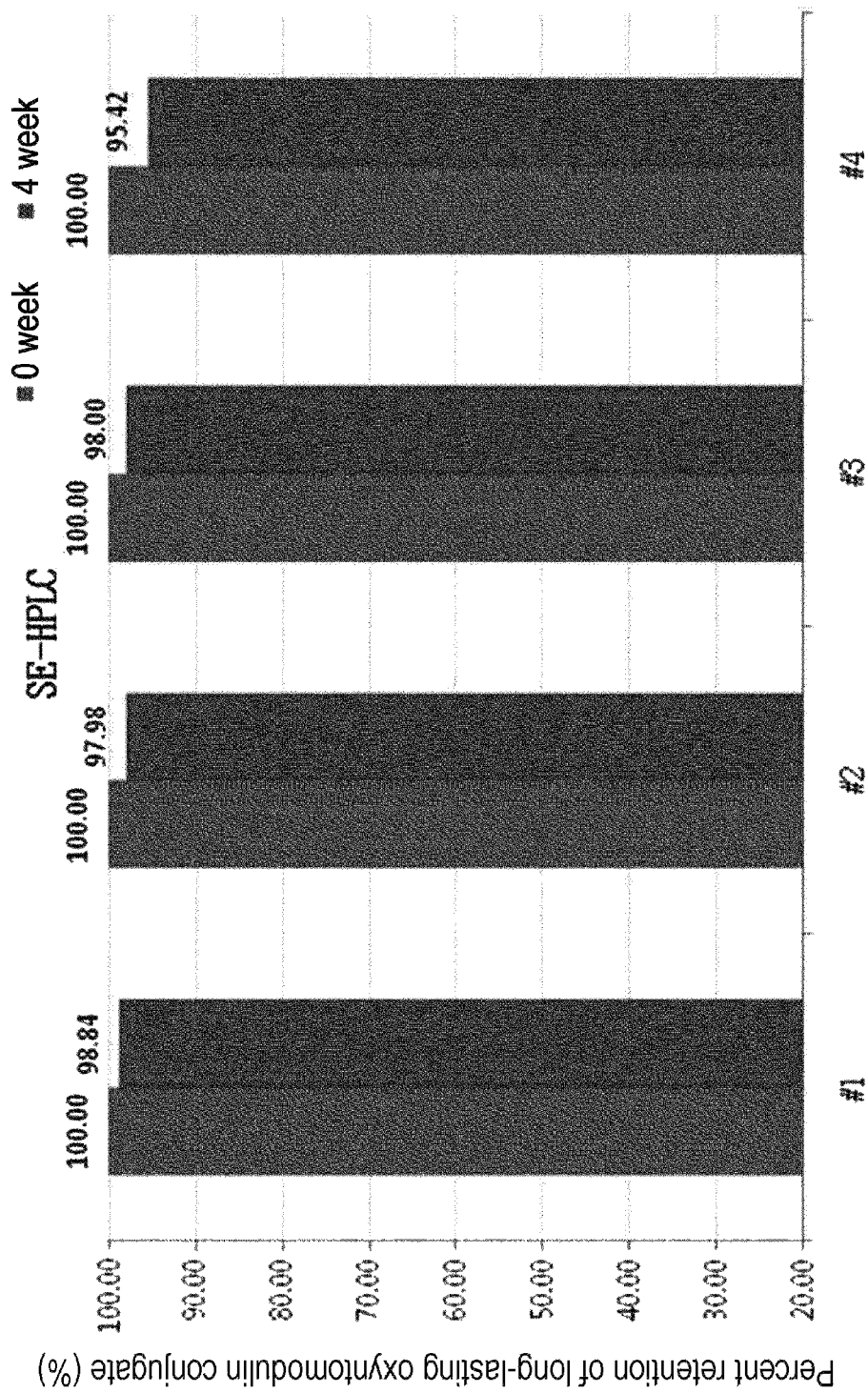
FIG. 8b is a graphic diagram showing the results obtained by evaluating the stability of a long-lasting oxyntomodulin conjugate according to the presence or absence of a preservative and the concentration of long-lasting oxyntomodulin by SE-HPLC in Example 9 after 0-4 weeks of storage at 25° C. Each graph in FIG. 8b shows the percent retention of the long-lasting oxyntomodulin conjugate relative to the start value.

Then, the purified mono-PEGylated oxyntomodulin derivative (SEQ ID NO: 25) and an immunoglobulin Fc were reacted with each other at a molar ratio of 1:5 and a protein concentration of 20 mg/ml at 4° C. for 16 hours. The reaction was performed in 100 mM potassium phosphate buffer (pH 6.0) in the presence of 20 mM SCB as a reducing agent. After completion of the reaction, the reaction was applied to a SOURCE 15Q purification column (column: SOURCE 15Q, flow rate: 2.0 ml/min, gradient: A 0→4% 1 min B→20% 80 min B (A: 20 mM Tris-HCl, pH 7.5, B: A+1M NaCl)) (FIG. 1b) and a source ISO purification column (column: SOURCE ISO, flow rate: 2.0 ml/min, gradient: B 0→100% 100 min A (A: 20 mM Tris-HCl, pH 7.5, B: A+1.1M AS)) (FIG. 1c) to purify a conjugate comprising the oxyntomodulin derivative (SEQ ID NO: 25) and the immunoglobulin Fc. FIG. 1b is a graph showing the results obtained by purifying the conjugate, comprising the oxyntomodulin derivative (SEQ ID NO: 25) and the immunoglobulin Fc, through the SOURCE 15Q purification column, and FIG. 1c is a graph showing the results obtained by purifying the conjugate, comprising the oxyntomodulin derivative (SEQ ID NO: 25) and the immunoglobulin Fc, through the Source ISO purification column.

The oxyntomodulin conjugate prepared as described above was developed to increase the blood half-life of oxyntomodulin. It comprises the immunoglobulin Fc region, the non-peptidyl polymer and the oxyntomodulin, linked covalently to each other in a site-specific manner, and has a significantly increased blood half-life.

EXAMPLE 3

Evaluation of Stability of Long-Lasting Oxyntomodulin Conjugate According to pH

In order to evaluate the stability of the long-lasting oxyntomodulin conjugate (prepared in Example 2) in liquid formulations, the long-lasting oxyntomodulin conjugate was stored in the compositions shown in Table 2 at 25° C. for 0-2 weeks, and then was analyzed by ion exchange-high performance liquid chromatography (IE-HPLC), size exclusion-high performance liquid chromatography (SE-HPLC) and reverse phase-high performance liquid chromatography (RP-HPLC). For storage of the oxyntomodulin conjugate, citrate buffer as buffer, mannitol as sugar alcohol, and polysorbate 20 as a nonionic surfactant were used. In Tables 3, 4 and 5 below, IE-HPLC (%), SE-HPLC (%) and RP-HPLC (%) indicate area %/start area %, which indicates the percent retention of the long-lasting oxyntomodulin conjugate relative to the start value. Table 3 shows the IE-HPLC area (%) of the long-lasting oxyntomodulin conjugate after storage, Table 4 shows the SE-HPLC area (%) of the long-lasting oxyntomodulin conjugate after storage, and Table 5 shows the RP-HPLC area (%) of the long-lasting oxyntomodulin conjugate after storage.

TABLE 2

| | pH | Buffer | Isotonic agent | Sugar alcohol | Surfactant | Others | Long-lasting oxyntomodulin |
|---|---|---|---|---|---|---|---|
| #1 | 4.8 | 20 mM Na-Citrate | — | 10% Mannitol | 0.005% Polysorbate 20 | 0.1 mg/mL Methionine | 10 mg/mL |
| #2 | 5.2 | 20 mM Na-Citrate | — | 10% Mannitol | 0.005% Polysorbate 20 | 0.1 mg/mL Methionine | 10 mg/mL |
| #3 | 5.6 | 20 mM Na-Citrate | — | 10% Mannitol | 0.005% Polysorbate 20 | 0.1 mg/mL Methionine | 10 mg/mL |
| #4 | 6.0 | 20 mM Na-Citrate | — | 10% Mannitol | 0.005% Polysorbate 20 | 0.1 mg/mL Methionine | 10 mg/mL |
| #5 | 6.4 | 20 mM Na-Citrate | — | 10% Mannitol | 0.005% Polysorbate 20 | 0.1 mg/mL Methionine | 10 mg/mL |

TABLE 3

| IE-HPLC (%) | | | | | |
|---|---|---|---|---|---|
| | #1 | #2 | #3 | #4 | #5 |
| 0 week | 100.0 | 100.0 | 100.0 | 100.0 | 100.0 |
| 2 weeks | 97.6 | 97.2 | 96.8 | 94.0 | 85.2 |

TABLE 4

| SE-HPLC (%) | | | | | |
|---|---|---|---|---|---|
| | #1 | #2 | #3 | #4 | #5 |
| 0 week | 100.0 | 100.0 | 100.0 | 100.0 | 100.0 |
| 2 weeks | 99.7 | 99.8 | 99.8 | 99.3 | 99.4 |

TABLE 5

| RP-HPLC (%) | | | | | |
|---|---|---|---|---|---|
| | #1 | #2 | #3 | #4 | #5 |
| 0 week | 100.0 | 100.0 | 100.0 | 100.0 | 100.0 |
| 2 weeks | 83.0 | 84.4 | 86.7 | 65.5 | 74.0 |

As can be seen from the results of IE-HPLC (%) in Table 3 above, the oxyntomodulin conjugate was more stable at lower pH. In the results of SE-HPLC in Table 4, the oxyntomodulin conjugate was most stable at a pH of 5.2, and in the results of RP-HPLC in Table 5, the oxyntomodulin conjugate was most stable at a pH of 5.6. Although the stability at pH did differ between the analysis methods, the difference in retention between pHs was the greatest in the RP-HPLC analysis method. This suggests that the oxyntomodulin conjugate was most stable at a pH of 5.6.

EXAMPLE 4

Evaluation of Stability of Long-Lasting Oxyntomodulin Conjugate According to the Kind of Sugar Alcohol and the Presence or Absence of Isotonic Agent The present inventors tested the influences of the kind of sugar alcohol as a stabilizer and the presence or absence of sodium chloride as an isotonic agent on the stability of the long-lasting oxyntomodulin conjugate. Specifically, using the citrate buffer (pH 5.6) selected in Example 3, the long-lasting oxyntomodulin conjugate was stored in the compositions shown in Table 6 below at 25° C. for 0-4 weeks, and then was analyzed by IE-HPLC, SE-HPLC and RP-HPLC. In Tables 7, 8 and 9 below, IE-HPLC (%), SE-HPLC (%) and RP-HPLC (%) indicate area %/start area %, which indicates the percent retention of the long-lasting oxyntomodulin conjugate relative to the start value. Table 7 shows the IE-HPLC area (%) of the long-lasting oxyntomodulin conjugate after storage, Table 8 shows the SE-HPLC area (%) of the long-lasting oxyntomodulin conjugate after storage, and Table 9 shows the RP-HPLC area (%) of the long-lasting oxyntomodulin conjugate after storage.

TABLE 6

| | pH | Buffer | Isotonic agent | Sugar alcohol | Surfactant | Others | Long-lasting oxyntomodulin |
|---|---|---|---|---|---|---|---|
| #1 | 5.6 | 20 mM Na-Citrate | — | 10% Mannitol | 0.005% Polysorbate 20 | — | 10 mg/mL |
| #2 | 5.6 | 20 mM Na-Citrate | — | 10% Sorbitol | 0.005% Polysorbate 20 | — | 10 mg/mL |
| #3 | 5.6 | 20 mM Na-Citrate | — | 10% Glycerol | 0.005% Polysorbate 20 | — | 10 mg/mL |
| #4 | 5.6 | 20 mM Na-Citrate | 150 mM NaCl | 10% Mannitol | 0.005% Polysorbate 20 | — | 10 mg/mL |

TABLE 7

| | IE-HPLC (%) | | | |
|---|---|---|---|---|
| | #1 | #2 | #3 | #4 |
| 0 week | 100.0 | 100.0 | 100.0 | 100.0 |
| 1 week | 98.8 | 98.8 | 88.3 | 98.3 |
| 2 weeks | 97.2 | 96.9 | 79.0 | 95.0 |
| 3 weeks | 94.4 | 94.5 | 63.0 | 93.8 |
| 4 weeks | 91.6 | 91.8 | 55.8 | 91.6 |

TABLE 8

| | SE-HPLC (%) | | | |
|---|---|---|---|---|
| | #1 | #2 | #3 | #4 |
| 0 week | 100.0 | 100.0 | 100.0 | 100.0 |
| 1 week | 99.9 | 100.0 | 92.0 | 100.0 |
| 2 weeks | 99.7 | 99.8 | 84.7 | 99.9 |
| 3 weeks | 99.2 | 99.4 | 79.2 | 99.5 |
| 4 weeks | 98.4 | 98.6 | 76.0 | 98.8 |

TABLE 9

| | RP-HPLC (%) | | | |
|---|---|---|---|---|
| | #1 | #2 | #3 | #4 |
| 0 week | 100.0 | 100.0 | 100.0 | 100.0 |
| 1 week | 98.9 | 98.7 | 90.0 | 98.4 |
| 2 weeks | 96.0 | 95.6 | 80.6 | 95.0 |
| 3 weeks | 94.0 | 93.6 | 75.2 | 92.9 |
| 4 weeks | 92.6 | 91.1 | 70.0 | 90.1 |

As can be seen in Tables 6 to 9 above, the long-lasting oxyntomodulin conjugate was more stable in mannitol or sorbitol than in glycerol at the same concentration. The results of RP-HPLC indicated that the long-lasting oxyntomodulin conjugate was a little stable in mannitol than in sorbitol. In addition, the stability of the long-lasting oxyntomodulin conjugate did not significantly differ between the presence and absence of sodium chloride as an isotonic agent.

EXAMPLE 5

Evaluation of Stability of Long-Lasting Oxyntomodulin Conjugate According to Concentration of Sugar Alcohol The present inventors tested the influence of the concentration of sugar alcohol as a stabilizer on the stability of the long-lasting oxyntomodulin conjugate. Specifically, using the citrate buffer (pH 5.6 and mannitol selected in the above Examples, the long-lasting oxyntomodulin conjugate was stored in the compositions shown in Table 10 below at 25° C. for 0-4 weeks, and then was analyzed by IE-HPLC, SE-HPLC and RP-HPLC. In Tables 11, 12 and 13 below, IE-HPLC (%), SE-HPLC (%) and RP-HPLC (%) indicate area %/start area %, which indicates the percent retention of the long-lasting oxyntomodulin conjugate relative to the start value. Table 11 shows the IE-HPLC area (%) of the long-lasting oxyntomodulin conjugate after storage, Table 12 shows the SE-HPLC area (%) of the long-lasting oxyntomodulin conjugate after storage, and Table 13 shows the RP-HPLC area (%) of the long-lasting oxyntomodulin conjugate after storage.

TABLE 10

|    | pH  | Buffer | Isotonic agent | Sugar alcohol | Surfactant | Others | Long-lasting oxyntomodulin |
|----|-----|--------|----------------|---------------|------------|--------|----------------------------|
| #1 | 5.6 | 20 mM Na-Citrate | — | 2% Mannitol | 0.005% Polysorbate 20 | — | 10 mg/mL |
| #2 | 5.6 | 20 mM Na-Citrate | — | 5% Mannitol | 0.005% Polysorbate 20 | — | 10 mg/mL |
| #3 | 5.6 | 20 mM Na-Citrate | — | 10% Mannitol | 0.005% Polysorbate 20 | — | 10 mg/mL |
| #4 | 5.6 | 20 mM Na-Citrate | — | 15% Mannitol | 0.005% Polysorbate 20 | — | 10 mg/mL |

TABLE 11

| | IE-HPLC (%) | | | |
|---|---|---|---|---|
| | #1 | #2 | #3 | #4 |
| 0 week | 100.0 | 100.0 | 100.0 | 100.0 |
| 1 week | 79.7 | 98.7 | 98.8 | 79.0 |
| 2 weeks | 57.6 | 97.6 | 97.9 | 61.0 |
| 3 weeks | 39.8 | 97.1 | 97.2 | 49.2 |
| 4 weeks | 34.9 | 95.5 | 95.5 | 43.4 |

TABLE 12

| | SE-HPLC (%) | | | |
|---|---|---|---|---|
| | #1 | #2 | #3 | #4 |
| 0 week | 100.0 | 100.0 | 100.0 | 100.0 |
| 1 week | 97.3 | 99.4 | 100.0 | 99.5 |
| 2 weeks | 89.0 | 99.4 | 99.8 | 95.4 |
| 3 weeks | 79.4 | 99.3 | 99.4 | 90.5 |
| 4 weeks | 74.7 | 98.4 | 99.1 | 83.5 |

TABLE 13

| | RP-HPLC (%) | | | |
|---|---|---|---|---|
| | #1 | #2 | #3 | #4 |
| 0 week | 100.0 | 100.0 | 100.0 | 100.0 |
| 1 week | 89.8 | 93.2 | 98.2 | 95.2 |
| 2 weeks | 80.3 | 85.3 | 94.7 | 90.9 |
| 3 weeks | 71.9 | 78.5 | 91.1 | 84.1 |
| 4 weeks | 66.0 | 71.0 | 89.1 | 76.5 |

As can be seen in Tables 10 to 13, the long-lasting oxyntomodulin conjugate was stable in the presence of 5% mannitol or 10% mannitol. However, a protein precipitate was formed in the presence of 2% mannitol or 15% mannitol. The results of IE-HPLC or SE-HPLC indicated that the stability of the long-lasting oxyntomodulin conjugate was similar between 10% mannitol and 5% mannitol. The results of RP-HPLC indicated that the stability of the long-lasting oxyntomodulin conjugate was more stable in 10% mannitol than in 5% mannitol.

EXAMPLE 6

Evaluation of Stability of Long-Lasting Oxyntomodulin Conjugate According to the Concentration of Surfactant and the Presence or Absence of Amino Acid The present inventors tested the influences of the concentration of a surfactant as a stabilizer and the presence or absence of an amino acid on the stability of the long-lasting oxyntomodulin conjugate. Using the citrate buffer (pH 5.6) and citrate buffer and 10% mannitol selected in the above Examples, the long-lasting oxyntomodulin conjugate was stored in the compositions shown in Table 14 below at 25° C. for 0-4 weeks, and then was analyzed by IE-HPLC, SE-HPLC and RP-HPLC. In Tables 15, 16 and 17 below, IE-HPLC (%), SE-HPLC (%) and RP-HPLC (%) indicate area %/start area %, which indicates the percent retention of the long-lasting oxyntomodulin conjugate relative to the start value. Table 15 shows the IE-HPLC area (%) of the long-lasting oxyntomodulin conjugate after storage, Table 16 shows the SE-HPLC area (%) of the long-lasting oxyntomodulin conjugate after storage, and Table 17 shows the RP-HPLC area (%) of the long-lasting oxyntomodulin conjugate after storage.

TABLE 14

|    | pH  | Buffer | Isotonic agent | Sugar alcohol | Surfactant | Others | Long-lasting oxyntomodulin |
|----|-----|--------|----------------|---------------|------------|--------|----------------------------|
| #1 | 5.6 | 20 mM Na-Citrate | — | 10% Mannitol | 0.005% Polysorbate 20 | — | 10 mg/mL |
| #2 | 5.6 | 20 mM Na-Citrate | — | 10% Mannitol | 0.02% Polysorbate 20 | — | 10 mg/mL |
| #3 | 5.6 | 20 mM Na-Citrate | — | 10% Mannitol | 0.05% Polysorbate 20 | — | 10 mg/mL |
| #4 | 5.6 | 20 mM Na-Citrate | — | 10% Mannitol | 0.02% Polysorbate 20 | 0.1 mg/ml Methionine | 10 mg/mL |

TABLE 15

| | IE-HPLC (%) | | | |
|---|---|---|---|---|
| | #1 | #2 | #3 | #4 |
| 0 week | 100.0 | 100.0 | 100.0 | 100.0 |
| 1 week | 96.0 | 96.5 | 96.4 | 96.2 |
| 2 weeks | 95.1 | 94.7 | 95.1 | 95.3 |
| 3 weeks | 92.7 | 92.0 | 92.2 | 92.7 |
| 4 weeks | 89.7 | 89.1 | 89.2 | 89.7 |

TABLE 16

| | SE-HPLC (%) | | | |
|---|---|---|---|---|
| | #1 | #2 | #3 | #4 |
| 0 week | 100.0 | 100.0 | 100.0 | 100.0 |
| 1 week | 99.4 | 99.7 | 99.7 | 99.6 |
| 2 weeks | 99.3 | 99.5 | 99.2 | 99.3 |
| 3 weeks | 98.3 | 98.1 | 98.3 | 99.1 |
| 4 weeks | 97.3 | 97.1 | 97.3 | 97.9 |

TABLE 17

| | RP-HPLC (%) | | | |
|---|---|---|---|---|
| | #1 | #2 | #3 | #4 |
| 0 week | 100.0 | 100.0 | 100.0 | 100.0 |
| 1 week | 97.3 | 97.8 | 98.1 | 97.4 |
| 2 weeks | 79.2 | 79.2 | 77.5 | 79.7 |
| 3 weeks | 71.5 | 71.6 | 69.5 | 73.3 |
| 4 weeks | 65.1 | 65.0 | 65.0 | 67.8 |

As can be seen from the results in Tables 14 to 17, the long-lasting oxyntomodulin conjugate was most stable in the composition containing 0.02% polysorbate 20 and 0.1 mg/mL methionine.

EXAMPLE 7

Evaluation of Stability of Long-Lasting Oxyntomodulin Conjugate According to pH and the Concentration of Sugar Alcohol The present inventors tested the influences of pH and the concentration of sugar alcohol as a stabilizer on the stability of the long-lasting oxyntomodulin conjugate. Specifically, using the 0.02% polysorbate 20 and 0.1 mg/mL methionine selected in the above Examples, the long-lasting oxyntomodulin conjugate was stored in the compositions shown in Table 18 below at 25° C. for 0-4 weeks, and then was analyzed by IE-HPLC, SE-HPLC and RP-HPLC. In Tables 19, 20 and 21 below, IE-HPLC (%), SE-HPLC (%) and RP-HPLC (%) indicate area %/start area %, which indicates the percent retention of the long-lasting oxyntomodulin conjugate relative to the start value. Table 19 shows the IE-HPLC area (%) of the long-lasting oxyntomodulin conjugate after storage, Table 20 shows the SE-HPLC area (%) of the long-lasting oxyntomodulin conjugate after storage, and Table 21 shows the RP-HPLC area (%) of the long-lasting oxyntomodulin conjugate after storage.

TABLE 18

| | pH | Buffer | Isotonic agent | Sugar alcohol | Surfactant | Others | Long-lasting oxyntomodulin |
|---|---|---|---|---|---|---|---|
| #1 | 5.2 | 20 mM Na-Citrate | — | 5% Mannitol | 0.02% Polysorbate 20 | 0.1 mg/ml Methionine | 10 mg/mL |
| #2 | 5.2 | 20 mM Na-Citrate | — | 10% Mannitol | 0.02% Polysorbate 20 | 0.1 mg/ml Methionine | 10 mg/mL |
| #3 | 5.2 | 20 mM Na-Citrate | — | 15% Mannitol | 0.02% Polysorbate 20 | 0.1 mg/ml Methionine | 10 mg/mL |
| #4 | 5.6 | 20 mM Na-Citrate | — | 5% Mannitol | 0.02% Polysorbate 20 | 0.1 mg/ml Methionine | 10 mg/mL |
| #5 | 5.6 | 20 mM Na-Citrate | — | 10% Mannitol | 0.02% Polysorbate 20 | 0.1 mg/ml Methionine | 10 mg/mL |
| #6 | 5.6 | 20 mM Na-Citrate | — | 15% Mannitol | 0.02% Polysorbate 20 | 0.1 mg/ml Methionine | 10 mg/mL |
| #7 | 6.0 | 20 mM Na-Citrate | — | 5% Mannitol | 0.02% Polysorbate 20 | 0.1 mg/ml Methionine | 10 mg/mL |
| #8 | 6.0 | 20 mM Na-Citrate | — | 10% Mannitol | 0.02% Polysorbate 20 | 0.1 mg/ml Methionine | 10 mg/mL |
| #9 | 6.0 | 20 mM Na-Citrate | — | 15% Mannitol | 0.02% Polysorbate 20 | 0.1 mg/ml Methionine | 10 mg/mL |

TABLE 19

| | IE-HPLC (%) | | | | | | | | |
|---|---|---|---|---|---|---|---|---|---|
| | #1 | #2 | #3 | #4 | #5 | #6 | #7 | #8 | #9 |
| 0 week | 100.0 | 100.0 | 100.0 | 100.0 | 100.0 | 100.0 | 100.0 | 100.0 | 100.0 |
| 1 week | 99.4 | 99.6 | 97.1 | 97.2 | 97.6 | 98.0 | 90.6 | 92.9 | 93.4 |
| 2 weeks | 97.5 | 97.8 | 90.5 | 93.8 | 94.1 | 93.2 | 81.5 | 83.6 | 85.6 |
| 3 weeks | 93.0 | 93.6 | 82.6 | 86.0 | 86.9 | 87.1 | 71.2 | 74.6 | 77.0 |
| 4 weeks | 90.0 | 90.5 | 71.1 | 85.0 | 85.6 | 85.7 | 62.7 | 66.3 | 68.9 |

TABLE 20

| | SE-HPLC (%) | | | | | | | | |
|---|---|---|---|---|---|---|---|---|---|
| | #1 | #2 | #3 | #4 | #5 | #6 | #7 | #8 | #9 |
| 0 week | 100.0 | 100.0 | 100.0 | 100.0 | 100.0 | 100.0 | 100.0 | 100.0 | 100.0 |
| 1 week | 98.8 | 99.5 | 98.8 | 99.5 | 99.3 | 98.5 | 99.6 | 100.0 | 100.7 |
| 2 weeks | 98.8 | 99.1 | 91.1 | 98.4 | 97.1 | 96.9 | 97.3 | 98.3 | 97.9 |
| 3 weeks | 97.7 | 98.3 | 96.4 | 98.1 | 98.4 | 98.2 | 98.1 | 99.1 | 100.8 |
| 4 weeks | 98.0 | 98.5 | 94.9 | 97.9 | 98.3 | 98.3 | 97.6 | 98.2 | 99.0 |

TABLE 21

| | RP-HPLC (%) | | | | | | | | |
|---|---|---|---|---|---|---|---|---|---|
| | #1 | #2 | #3 | #4 | #5 | #6 | #7 | #8 | #9 |
| 0 week | 100.0 | 100.0 | 100.0 | 100.0 | 100.0 | 100.0 | 100.0 | 100.0 | 100.0 |
| 1 week | 78.2 | 78.2 | 42.1 | 88.2 | 90.7 | 89.4 | 99.9 | 99.1 | 100.7 |
| 2 weeks | 60.7 | 58.6 | — | 80.4 | 80.2 | 80.6 | 96.8 | 93.4 | 92.0 |
| 3 weeks | 47.5 | 41.9 | — | 79.4 | 77.3 | 69.8 | 97.6 | 92.8 | 93.6 |
| 4 weeks | 34.8 | 28.0 | — | 72.8 | 65.0 | 62.6 | 96.9 | 91.1 | 88.9 |

As can be seen from the results in Tables above, the results of IE-HPLC indicated that the stability of the long-lasting oxyntomodulin conjugate was higher in the order of pH 5.2, pH 5.6 and pH 6.0. The results of RP-HPLC indicated that the stability of the long-lasting oxyntomodulin conjugate was higher in the order of pH 6.0, pH 5.6 and pH 5.2. The results of SE-HPLC indicated that the stability of the long-lasting oxyntomodulin conjugate did not significantly differ between pH 5.2, pH 5.6 and pH 6.0. In other words, the results of IE-HPLC, RP-HPLC and SE-HPLC indicated that the long-lasting oxyntomodulin conjugate was stable at pH 5.6.

Meanwhile, the results of IE-HPLC and SE-HPLC indicated that the long-lasting oxyntomodulin conjugate did not significantly differ between mannitol concentrations at pH 5.6. However, in the results of RP-HPLC, the long-lasting oxyntomodulin conjugate was more stable in 5% mannitol than in 10% or 15% mannitol at pH 5.6.

EXAMPLE 8

Evaluation of Stability of Long-Lasting Oxyntomodulin Conjugate According to pH and the Kind of Buffer The present inventors tested the influences of pH and the kind of buffer as a stabilizer on the stability of the long-lasting oxyntomodulin conjugate. Specifically, using the 0.02% polysorbate 20, 0.1 mg/mL methionine and 5% mannitol selected in the above Examples, the long-lasting oxyntomodulin conjugate was stored in the compositions shown in Table 22 below at 25° C. for 0-4 weeks, and then was analyzed by IE-HPLC, SE-HPLC and RP-HPLC.

In Tables 23, 24 and 25 below, IE-HPLC (%), SE-HPLC (%) and RP-HPLC (%) indicate area %/start area %, which indicates the percent retention of the long-lasting oxyntomodulin conjugate relative to the start value. Table 23 shows the IE-HPLC area (%) of the long-lasting oxyntomodulin conjugate after storage, Table 24 shows the SE-HPLC area (%) of the long-lasting oxyntomodulin conjugate after storage, and Table 25 shows the RP-HPLC area (%) of the long-lasting oxyntomodulin conjugate after storage.

TABLE 22

| | pH | Buffer | Isotonic agent | Sugar alcohol | Surfactant | Others | Long-lasting oxyntomodulin |
|---|---|---|---|---|---|---|---|
| #1 | 5.6 | 20 mM Na-Citrate | — | 5% Mannitol | 0.02% Polysorbate 20 | 0.1 mg/ml Methionine | 10 mg/ml |
| #2 | 5.8 | 20 mM Na-Citrate | — | 5% Mannitol | 0.02% Polysorbate 20 | 0.1 mg/ml Methionine | 10 mg/mL |
| #3 | 5.8 | 20 mM Na-Acetate | — | 5% Mannitol | 0.02% Polysorbate 20 | 0.1 mg/ml Methionine | 10 mg/mL |
| #4 | 5.8 | 10 mM Histidine | — | 5% Mannitol | 0.02% Polysorbate 20 | 0.1 mg/ml Methionine | 10 mg/mL |
| #5 | 5.8 | 10 mM Na-Phosphate | — | 5% Mannitol | 0.02% Polysorbate 20 | 0.1 mg/ml Methionine | 10 mg/mL |

TABLE 23

| | IE-HPLC (%) | | | | |
|---|---|---|---|---|---|
| | #1 | #2 | #3 | #4 | #5 |
| 0 week | 100.0 | 100.0 | 100.0 | 100.0 | 100.0 |
| 1 week | 97.6 | 96.8 | 96.5 | 97.2 | 96.1 |
| 2 weeks | 93.9 | 91.4 | 90.6 | 92.6 | 89.6 |
| 3 weeks | 90.4 | 88.1 | 86.9 | 89.2 | 84.4 |
| 4 weeks | 90.1 | 87.0 | 84.8 | 87.4 | 81.7 |

TABLE 24

| | SE-HPLC (%) | | | | |
|---|---|---|---|---|---|
| | #1 | #2 | #3 | #4 | #5 |
| 0 week | 100.0 | 100.0 | 100.0 | 100.0 | 100.0 |
| 1 week | 99.4 | 99.8 | 99.8 | 99.7 | 99.7 |
| 2 weeks | 100.5 | 100.2 | 100.0 | 100.0 | 99.3 |
| 3 weeks | 100.4 | 100.2 | 99.1 | 99.6 | 98.2 |
| 4 weeks | 100.1 | 99.2 | 99.0 | 98.8 | 97.7 |

TABLE 25

| | RP-HPLC (%) | | | | |
|---|---|---|---|---|---|
| | #1 | #2 | #3 | #4 | #5 |
| 0 week | 100.0 | 100.0 | 100.0 | 100.0 | 100.0 |
| 1 week | 99.1 | 97.2 | 99.4 | 99.5 | 99.0 |

TABLE 25-continued

| | RP-HPLC (%) | | | | |
|---|---|---|---|---|---|
| | #1 | #2 | #3 | #4 | #5 |
| 2 weeks | 97.6 | 97.7 | 99.4 | 99.8 | 99.3 |
| 3 weeks | 96.1 | 98.7 | 97.2 | 98.9 | 97.4 |
| 4 weeks | 98.0 | 96.6 | 97.6 | 98.3 | 98.1 |

As can be seen from the results in Tables 23 to 25, the results of SE-HPLC or RP-HPLC indicated that the stability of the long-lasting oxyntomodulin conjugate did not significantly differ between pH 5.6 and pH 5.8. The results of IE-HPLC indicated that the long-lasting oxyntomodulin conjugate was more stable at pH 5.6 than at pH 5.8. The results of SE-HPLC showed that the stability of the long-lasting oxyntomodulin conjugate did not significantly differ between the buffers at the same pH. In addition, the results of IE-HPLC or RP-HPLC indicated that the long-lasting oxyntomodulin conjugate was most stable in histidine at the same pH.

EXAMPLE 9

Evaluation of Influences of the Presence or Absence of Preservative and the Concentration of Long-Lasting Oxyntomodulin Conjugate on the Stability of Long-Lasting Oxyntomodulin Conjugate The present inventors tested the influences of the presence or absence of a preservative as a stabilizer and the concentration of the long-lasting oxyntomodulin conjugate on the stability of the long-lasting oxyntomodulin conjugate. Specifically, using histidine buffer (pH 5.6), 0.02% polysorbate 20, 0.1 mg/mL methionine and 5% mannitol, selected in the above Examples, the long-lasting oxyntomodulin conjugate was stored in the compositions shown in Table 26 below at 25° C. for 0-4 weeks, and then was analyzed by IE-HPLC, SE-HPLC and RP-HPLC. In Tables 27, 28 and 29 below, IE-HPLC (%), SE-HPLC (%) and RP-HPLC (%) indicate area %/start area %, which indicates the percent retention of the long-lasting oxyntomodulin conjugate relative to the start value. Table 27 shows the IE-HPLC area (%) of the long-lasting oxyntomodulin conjugate after storage, Table 28 shows the SE-HPLC area (%) of the long-lasting oxyntomodulin conjugate after storage, and Table 29 shows the RP-HPLC area (%) of the long-lasting oxyntomodulin conjugate after storage.

TABLE 26

| | pH | Buffer | Isotonic agent | Sugar alcohol | Surfactant | Others | Long-lasting oxyntomodulin |
|---|---|---|---|---|---|---|---|
| #1 | 5.6 | 10 mM Histidine | — | 5% Mannitol | 0.02% Polysorbate 20 | 0.1 mg/ml Methionine | 10 mg/mL |
| #2 | 5.6 | 10 mM Histidine | — | 5% Mannitol | 0.02% Polysorbate 20 | 0.1 mg/ml Methionine 0.27% m-cresol | 10 mg/mL |
| #3 | 5.6 | 10 mM Histidine | — | 5% Mannitol | 0.02% Polysorbate 20 | 0.1 mg/ml Methionine | 40 mg/mL |
| #4 | 5.6 | 10 mM Histidine | — | 5% Mannitol | 0.02% Polysorbate 20 | 0.1 mg/ml Methionine 0.27% m-cresol | 40 mg/mL |

TABLE 27

| | IE-HPLC (%) | | | |
|---|---|---|---|---|
| | #1 | #2 | #3 | #4 |
| 0 week | 100.0 | 100.0 | 100.0 | 100.0 |
| 1 week | 97.9 | 98.2 | 97.7 | 97.1 |
| 2 weeks | 95.3 | 95.7 | 95.1 | 94.3 |
| 3 weeks | 93.6 | 92.9 | 93.4 | 91.8 |
| 4 weeks | 91.3 | 90.4 | 90.2 | 88.4 |

TABLE 28

| | SE-HPLC (%) | | | |
|---|---|---|---|---|
| | #1 | #2 | #3 | #4 |
| 0 week | 100.0 | 100.0 | 100.0 | 100.0 |
| 1 week | 99.7 | 99.6 | 99.5 | 99.4 |
| 2 weeks | 99.3 | 99.1 | 99.0 | 97.9 |
| 3 weeks | 99.1 | 98.9 | 98.7 | 97.0 |
| 4 weeks | 98.8 | 98.0 | 98.0 | 95.4 |

TABLE 29

| | RP-HPLC (%) | | | |
|---|---|---|---|---|
| | #1 | #2 | #3 | #4 |
| 0 week | 100.0 | 100.0 | 100.0 | 100.0 |
| 1 week | 100.1 | 100.0 | 99.8 | 99.7 |
| 2 weeks | 99.4 | 99.5 | 99.2 | 99.1 |
| 3 weeks | 98.3 | 98.3 | 98.8 | 98.5 |
| 4 weeks | 98.8 | 97.9 | 97.7 | 97.4 |

As can be seen in Tables 26 to 29, the results of IE-HPLC, SE-HPLC or RP-HPLC indicated that the stability of long-lasting oxyntomodulin conjugate did not change even in the presence of the preservative and did not differ according to the concentration thereof.

Although the preferred embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A liquid formulation of a long-lasting oxyntomodulin derivative conjugate, comprising:
   a pharmacologically active amount of a long-lasting oxyntomodulin derivative conjugate wherein the oxyntomodulin derivative conjugate comprises
   an oxyntomodulin derivative, which is a physiologically active peptide, comprising the amino acid sequence of SEQ ID NO: 24, 25, or 26,
   an immunoglobulin Fc region; and
   a non-peptidyl polymer, wherein the non-peptidyl polymer covalently links the oxyntomodulin derivative and the immunoglobulin Fc region;
   and an albumin-free stabilizer, wherein the stabilizer contains a buffer, a sugar alcohol and a nonionic surfactant.

2. The liquid formulation of a long-lasting oxyntomodulin derivative conjugate according to claim 1, wherein the stabilizer further contains one or more selected from the group consisting of isotonic agents, sugars, polyhydric alcohols and amino acids.

3. The liquid formulation of a long-lasting oxyntomodulin derivative conjugate according to claim 1, wherein the non-peptidyl polymer is selected from the group consisting of polypropylene glycol, an ethylene glycol/propylene glycol copolymer, polyoxyethylated polyol, polyvinyl alcohol, polysaccharides, dextran, polyvinyl ethyl ether, biodegradable polymers, including polylactic acid (PLA) and poly-lactic-glycolic acid (PLGA); lipid polymers; chitins; hyaluronic acid; and combinations thereof.

4. The liquid formulation of a long-lasting oxyntomodulin derivative conjugate according to claim 1, wherein the non-peptidyl polymer is polyethylene glycol.

5. The liquid formulation of a long-lasting oxyntomodulin derivative conjugate according to claim 1, wherein the sugar alcohol is one or more selected from the group consisting of mannitol, sorbitol and glycerol.

6. The liquid formulation of a long-lasting oxyntomodulin derivative conjugate according to claim 5, wherein the concentration of the sugar alcohol in the liquid formulation is 2-15% (w/v).

7. The liquid formulation of a long-lasting oxyntomodulin derivative conjugate according to claim 1, wherein the buffer is one or more selected from the group consisting of citrate, acetate, histidine and phosphate buffer.

8. The liquid formulation of a long-lasting oxyntomodulin derivative conjugate according to claim 1, wherein the buffer has a pH ranging from 4.5 to 7.0.

9. The liquid formulation of a long-lasting oxyntomodulin derivative conjugate according to claim 2, wherein the isotonic agent is sodium chloride.

10. The liquid formulation of a long-lasting oxyntomodulin derivative conjugate according to claim 1, wherein the nonionic surfactant is polysorbate or poloxamer.

11. The liquid formulation of a long-lasting oxyntomodulin derivative conjugate according to claim 10, wherein the concentration of the nonionic surfactant in the liquid formulation is 0.001-0.1% (w/v).

12. The liquid formulation of a long-lasting oxyntomodulin derivative conjugate according to claim 2, wherein the amino acid is methionine.

13. The liquid formulation of a long-lasting oxyntomodulin derivative conjugate according to claim 1, wherein the stabilizer contains a buffer having a pH ranging from 4.8 to 6.0, one or more sugar alcohols selected from the group consisting of mannitol and sorbitol, and polysorbate 20.

14. The liquid formulation of a long-lasting oxyntomodulin derivative conjugate according to claim 1, further comprising one or more preservatives selected from the group consisting of m-cresol, phenol and benzyl alcohol.

15. The liquid formulation of a long-lasting oxyntomodulin derivative conjugate according to claim 14, wherein the concentration of the preservative in the liquid formulation is 0.001-1% (w/v).

16. A liquid formulation of a long-lasting oxyntomodulin derivative conjugate, comprising:
   a pharmacologically effective amount of a long-lasting oxyntomodulin derivative conjugate wherein the oxyntomodulin derivative conjugate comprises
   an oxyntomodulin derivative, which is a physiologically active peptide, comprising the amino acid sequence of SEQ ID NO: 24, 25, or 26, an immunoglobulin Fc region, and
a non-peptidyl polymer, wherein the non-peptidyl polymer covalently links the oxyntomodulin derivative and the immunoglobulin Fc region;
and 5-50 mM histidine; 2-15% (w/v) of mannitol; 0.01-1 mg/mL of methionine; and 0.001-0.1% (w/v) of polysorbate 20.

17. A method for preparing the liquid formulation of claim 1, the method comprising the steps of:
a) preparing a long-lasting oxyntomodulin derivative conjugate, wherein the oxyntomodulin derivative conjugate comprises
an oxyntomodulin derivative, which is a physiologically active peptide, comprising the amino acid sequence of SEQ ID NO: 24, 25, or 26,
an immunoglobulin Fc region; and
a non-peptidyl polymer, wherein the non-peptidyl polymer covalently links the oxyntomodulin derivative and the immunoglobulin Fc region; and
b) mixing the long-lasting oxyntomodulin derivative conjugate, prepared in step a), with an albumin-free stabilizer, wherein the stabilizer contains a buffer, a sugar alcohol and a nonionic surfactant.

18. A method for preparing the liquid formulation of claim 14, the method comprising the steps of:
a) preparing a long-lasting oxyntomodulin derivative conjugate, wherein the oxyntomodulin derivative conjugate comprises
an oxyntomodulin derivative, which is a physiologically active peptide, comprising the amino acid sequence of SEQ ID NO: 24, 25, or 26,
an immunoglobulin Fc region; and
a non-peptidyl polymer, wherein the non-peptidyl polymer covalently links the oxyntomodulin derivative and the immunoglobulin Fc region; and
b) mixing the long-lasting oxyntomodulin derivative conjugate, prepared in step a), with an albumin-free stabilizer, wherein the stabilizer contains a buffer, a sugar alcohol, a nonionic surfactant, and one or more preservatives selected from the group consisting of m-cresol, phenol and benzyl alcohol.

19. The method of claim 17, wherein the stabilizer further contains one or more selected from the group consisting of isotonic agents, sugars, polyhydric alcohols and amino acids.

20. The method of claim 18, wherein the stabilizer further contains one or more selected from the group consisting of isotonic agents, sugars, polyhydric alcohols and amino acids.

21. The liquid formulation of a long-lasting oxyntomodulin derivative conjugate according to claim 1, wherein the immunoglobulin Fc region is a human aglycosylated IgG4 Fc region.

22. The liquid formulation of a long-lasting oxyntomodulin derivative conjugate according to claim 1, wherein the oxyntomodulin derivative comprises the amino acid sequence of SEQ ID NO: 24.

23. The liquid formulation of a long-lasting oxyntomodulin derivative conjugate according to claim 1, wherein the oxyntomodulin derivative comprises the amino acid sequence of SEQ ID NO: 25.

24. The liquid formulation of a long-lasting oxyntomodulin derivative conjugate according to claim 1, wherein the oxyntomodulin derivative comprises the amino acid sequence of SEQ ID NO: 26.

25. The liquid formulation of a long-lasting oxyntomodulin derivative conjugate according to claim 16, wherein the oxyntomodulin derivative comprises the amino acid sequence of SEQ ID NO: 24.

26. The liquid formulation of a long-lasting oxyntomodulin derivative conjugate according to claim 16, wherein the oxyntomodulin derivative comprises the amino acid sequence of SEQ ID NO: 25.

27. The liquid formulation of a long-lasting oxyntomodulin derivative conjugate according to claim 16, wherein the oxyntomodulin derivative comprises the amino acid sequence of SEQ ID NO: 26.

* * * * *